US011932898B2

United States Patent
Rao et al.

(10) Patent No.: US 11,932,898 B2
(45) Date of Patent: Mar. 19, 2024

(54) PRECISION THERAPEUTIC BIOMARKER SCREENING FOR CANCER

(71) Applicant: UNIVERSITY OF MIAMI, Miami, FL (US)

(72) Inventors: Jonnagadda Sunil Rao, Miami, FL (US); Hongmei Liu, Miami, FL (US)

(73) Assignee: UNIVERSITY OF MIAMI, Miami, FL (US)

( * ) Notice: Subject to any disclaimer, the term of this patent is extended or adjusted under 35 U.S.C. 154(b) by 1421 days.

(21) Appl. No.: 16/321,755

(22) PCT Filed: Jul. 31, 2017

(86) PCT No.: PCT/US2017/044712
§ 371 (c)(1),
(2) Date: Jan. 29, 2019

(87) PCT Pub. No.: WO2018/023120
PCT Pub. Date: Feb. 1, 2018

(65) Prior Publication Data
US 2019/0161784 A1      May 30, 2019

Related U.S. Application Data

(60) Provisional application No. 62/368,997, filed on Jul. 29, 2016.

(51) Int. Cl.
*C12Q 1/02* (2006.01)
*G01N 33/50* (2006.01)
(Continued)

(52) U.S. Cl.
CPC ......... *C12Q 1/025* (2013.01); *G01N 33/5044* (2013.01); *G16B 5/20* (2019.02);
(Continued)

(58) Field of Classification Search
CPC .............. C12Q 2600/106; C12Q 1/025; G01N 33/5044; G16B 5/20; G16B 15/30;
(Continued)

(56) References Cited

U.S. PATENT DOCUMENTS

2008/0118576 A1    5/2008  Theodorescu et al.
2010/0042563 A1*   2/2010  Livingston .......... G06F 18/2321
                                                                    703/2

(Continued)

OTHER PUBLICATIONS

Monga, Manish, and Edward A. Sausville. "Developmental therapeutics program at the NCI: molecular target and drug discovery process." Leukemia 16.4 (2002): 520-526. (Year: 2002).*

(Continued)

*Primary Examiner* — Jesse P Frumkin

(57) ABSTRACT

Computer-implemented processes for precision therapeutic biomarker screening for cancer include using a model-based overlapping clustering framework to assess large numbers of possible drugs and drug combinations against patient data, including cell line responsiveness. A multivariate regression model has been developed, along with a latent overlapping cluster indicator variable. The techniques employ a new finite mixture of multivariate regression (FMMR) model and expectation-maximization (EM) algorithm for modeling. The techniques can analyze large amounts of drug data and identify complex overlapping drug clusters, as well as cluster-wise drivers that facilitate identification of new drugs for treating pathologies, such as cancer, in patients.

14 Claims, 41 Drawing Sheets

(51) Int. Cl.

| | | |
|---|---|---|
| G16B 5/20 | (2019.01) | |
| G16B 15/30 | (2019.01) | |
| G16B 40/20 | (2019.01) | |
| G16H 10/20 | (2018.01) | |
| G16H 10/40 | (2018.01) | |
| G16H 50/50 | (2018.01) | |
| G16H 50/70 | (2018.01) | |

(52) U.S. Cl.
CPC .............. *G16B 15/30* (2019.02); *G16B 40/20* (2019.02); *G16H 10/20* (2018.01); *G16H 10/40* (2018.01); *G16H 50/50* (2018.01); *G16H 50/70* (2018.01)

(58) Field of Classification Search
CPC ........ G16B 40/20; G16H 10/20; G16H 10/40; G16H 50/50; G16H 50/70
See application file for complete search history.

(56) References Cited

U.S. PATENT DOCUMENTS

| | | |
|---|---|---|
| 2010/0144554 A1 | 6/2010 | Semizarov et al. |
| 2010/0198900 A1 | 8/2010 | Gifford |
| 2015/0072878 A1* | 3/2015 | Buechler .............. C12Q 1/6886 702/19 |
| 2016/0102365 A1 | 4/2016 | Ince |

OTHER PUBLICATIONS

Akaike, A new look at the statistical model identification, IEEE transactions on automatic control, 19(6):716-723 (1974).
Anderson, Avoiding pitfalls when using informationtheoretic methods, The Journal of Wildlife Management, 912-918 (2002).
Azzalini, The skew-normal distribution and related multivariate families, Scandinavian Journal of Statistics, 32(2):159-188 (2005).
Bailey et al., Implementation of biomarker-driven cancer therapy: existing tools and remaining gaps, Discovery medicine, 17(92):101-114 (2014).
Banerjee et al., Model-based overlapping clustering, Proceedings of the eleventh ACM SIGKDD international conference on Knowledge discovery in data mining, ACM, 532-537 (2005).
Barretina et al., The Cancer Cell Line Encyclopedia enables predictive modelling of anticancer drug sensitivity, Nature, 483(7391):603-607 (2012).
Basu et al., An Interactive Resource to Identify Cancer Genetic and Lineage Dependencies Targeted by Small Molecules, Cell, 154(5):1151-1161 (2013).
Branco et al., A general class of multivariate skew-elliptical distributions, Journal of Multivariate Analysis, 79(1):99-113 (2001).
Breiman et al., Predicting multivariate responses in multiple linear regression, Journal of the Royal Statistical Society: Series B (Statistical Methodology), 59(1):3-54 (1997).
Chen et al., Regularized multivariate regression models with skew-t error distributions, Journal of Statistical Planning and Inference, 149:125-139 (2014).
Dempster et al., Maximum likelihood from incomplete data via the EM algorithm, Journal of the royal statistical society: Series B (methodological), 39(1):1-38 (1977).
Desarbo et al., A maximum likelihood methodology for clusterwise linear regression, Journal of classification, 5(2):249-282 (1988).
Druker et al., Five-year follow-up of patients receiving imatinib for chronic myeloid leukemia, New England Journal of Medicine, 355(23):2408-2417 (2006).
Estivill-Castro, Why so many clustering algorithms: a position paper, ACM SIGKDD explorations newsletter, 4(1):65-75 (2002).
Fan et al., A selective overview of variable selection in high dimensional feature space, Statistica Sinica, 20(1):101-148 (2010).

Fan et al., Statistical challenges with high dimensionality: Feature selection in knowledge discovery, arXiv preprint math/0602133, (2006).
Fraley et al., How many clusters? Which clustering method? Answers via model-based cluster analysis, The computer journal, 41(8):578-588 (1998).
Frey et al., Clustering by passing messages between data points, science, 315(5814):972-976 (2007).
Fu et al., Multiplicative mixture models for overlapping clustering, in 2008 Eighth IEEE International Conference on Data Mining, IEEE, 791-796 (2008).
Galimberti et al., A multivariate linear regression analysis using finite mixtures of t distributions, Computational Statistics & Data Analysis, 71:138-150 (2014).
Garnett et al., Systematic identification of genomic markers of drug sensitivity in cancer cells, Nature, 483(7391):570-575 (2012).
Grun et al., FlexMix version 2: finite mixtures with concomitant variables and varying and constant parameters, (2008).
Heller et al., A Nonparametric Bayesian Approach to Modeling Overlapping Clusters, in AISTATS, 187-194 (2007).
International Application No. PCT/US17/44712, International Preliminary Report on Patentability, dated Feb. 7, 2019.
International Application No. PCT/US17/44712, International Search Report and Written Opinion, dated Oct. 6, 2017.
Ishwaran et al., Random survival forests, Ann. App. Stat., 2(3):841-860 (2008).
Jain et al., Data clustering: a review, ACM computing surveys (CSUR), 31(3):264-323 (1999).
Jedidi et al., On estimating finite mixtures of multivariate regression and simultaneous equation models, Structural Equation Modeling: A Multidisciplinary Journal, 3(3):266-289 (1996).
Jiang et al., The E-MS algorithm: model selection with incomplete data, Journal of the American Statistical Association, 110(511):1136-1147 (2015).
Keribin, Consistent estimation of the order of mixture models, Sankhy a: The Indian Journal of Statistics, Series, 62:49-66 (2000).
Khalili et al., Regularization in finite mixture of regression models with diverging No. of parameters, Biometrics, 69(2):436-446 (2013).
Khalili et al., Variable selection in finite mixture of regression models, Journal of the American Statistical Association 102(479):1025-1038 (2012).
Lazzeroni et al., Plaid models for gene expression data, Statistica sinica, 12(1):61-86 (2002).
Leisch, Flexmix: A general framework for finite mixture models and latent glass regression in R, (2004).
Liu et al., Precision therapeutic biomarker identification with application to the cancer genome project, arXiv preprint arXiv:1702.02264, (2017).
Martins et al., Linking Tumor Mutations to Drug Responses via a Quantitative Chemical-Genetic Interaction Map, Cancer discovery, 5(2):154-167 (2015).
Merimsky et al., Gemcitabine in soft tissue or bone sarcoma resistant to standard chemotherapy: a phase II study, Cancer chemotherapy and pharmacology, 45(2):177-181 (2000).
Peng et al., Regularized multivariate regression for identifying master predictors with application to integrative genomics study of breast cancer, Ann. Appl. Stat., 4(1):53-77 (2010).
Rothman et al., Sparse multivariate regression with covariance estimation, Journal of Computational and Graphical Statistics, 19(4):947-962 (2010).
Schwarz, Estimating the dimension of a model, The annals of statistics, 6(2):461-464 (1978).
Segal et al., Decomposing gene expression into cellular processes, Biocomputing, 8:89-100 (2002).
Simila et al., Input selection and shrinkage in multiresponse linear regression, Computational Statistics & Data Analysis, 52(1):406-422 (2007).
Soffritti et al., Multivariate linear regression with non-normal errors: a solution based on mixture models, Statistics and Computing, 21(4):523-536 (2011).
Stekhoven et al., MissForestnon-parametric missing value imputation for mixed-type data, Bioinformatics, 28(1):112-118 (2012).

(56) References Cited

OTHER PUBLICATIONS

Stone, An asymptotic equivalence o f choice of model by cross-validation and Akaike's criterion, Journal of the Royal Statistical Society: Series B (Methodological), 39(1):44-47 (1977).

Tibshirani, Regression shrinkage and selection via the lasso, Journal of the Royal Statistical Society: Series B (Methodological), 58(1):267-288 (1996).

Turlach et al., Simultaneous variable selection, Technometrics, 47(3):349-363 (2005).

Turner et al., Biclustering models for structured microarray data, IEEE/ACM Transactions on Computational Biology and Bioinformatics (TCBB), 2(4):316-329 (2005).

Turner et al., Improved biclustering of microarray data demonstrated through systematic performance tests, Computational statistics & data analysis, 48(2):235-254 (2005).

Wildey et al., Pharmacogenomic approach to identify drug sensitivity in small-cell lung cancer, PloS one, 9(9):e106784 (2014).

Zhang, A Bayesian model for biclustering with applications, Journal of the Royal Statistical Society: Series C (Applied Statistics), 59(4):635-656 (2010).

Zou et al., Regularization and variable selection via the elastic net, Journal of the Royal Statistical Society: Series B (Statistical Methodology), 67(2):301-320 (2005).

\* cited by examiner

| Sensitive drug names | Resistant drug names |
|---|---|
| Vinorelbine | BMS.708163 |
| Docetaxel | Nutlin.3a |
| Gemcitabine* | AZD6482 |
| JW.7.52.1 | ZM.447439 |
|  | PAC.1 |
|  | OSU.03012 |

Table 1: Sensitive versus resistant drugs for soft tissue cancer.

FIG. 16 for $k = 1 : K$ do

At this point, we have already found $k - 1$ layers and are searching for the $k$th layer.

Calculate the residuals from previous $k - 1$ layers by $$z_i = y_i - \sum_{l=1}^{k-1} x_i^T B_l P_{li}, \quad i = 1, \ldots, n.$$

Initialize $P_k^0$.

for $s = 1 : S$ do

Given $P_k^{s-1}$, compute $$B_k^s = \arg\min_{B_k} \frac{1}{2} \sum_{i=1}^{n} \|z_i - x_i^T B_k P_{ki}^{s-1}\|_2^2 + \sum_{j=1}^{q} \lambda_{jk} \|b_{jk}\|_1,$$

where $B_k = (b_{1k}, \ldots, b_{qk})$.

Given $B_k^s$, compute $$P_{ik}^s = \begin{cases} 0.5 + \min\{0.5, \frac{S}{2(S-T)}\}, & \|z_i - x_i^T B_k^s\|_2^2 \leq \|z_i\|_2^2 \\ 0.5 - \min\{0.5, \frac{S}{2(S-T)}\}, & \text{otherwise}, \end{cases}$$

where $T$ was taken as $0.25$ for $i = 1, \ldots, n$.

end

Given $P_k^S$, update $B_k^{S+1}$.

Given $B_k^{S+1}$, prune layer memberships by $$P_{ik}^{S+1} = \begin{cases} 1, & \|z_i - x_i^T B_k\|_2^2 \leq \tau \|z_i\|_2^2, \\ 0, & \text{otherwise}, \end{cases}$$

where $\tau \in (0, 1)$ for $i = 1, \ldots, n$.

Given $P_k^{S+1}$, update $B_k^{S+2}$.

Given $P_1^{S+1}, \ldots, P_k^{S+1}$, back fit the layers $R$ times. We set $R = 2$.

end

Algorithm 1: Plaid

FIG. 17

Initialize $B_1^0, \ldots, B_K^0$ and $P_1^0, \ldots, P_K^0$.

for $s = 1 : S$ do for $k = 1 : K$ do

Given $(B_1^s, \ldots, B_{k-1}^s, B_{k+1}^{s-1}, \ldots, B_K^{s-1})$ and $(P_1^s, \ldots, P_{k-1}^s, P_k^{s-1}, \ldots, P_K^{s-1})$, compute $$z_i = y_i - \sum_{l=1}^{k-1} x_i^T B_l^s P_{il}^s - \sum_{l=k+1}^{K} x_i^T B_l^{s-1} P_{il}^{s-1}, \quad i = 1, \ldots, n,$$

$$B_k^s = \arg\min_{B_k} \frac{1}{2} \sum_{i=1}^{n} \|z_i - x_i^T B_k P_{ik}^{s-1}\|_2^2 + \sum_{j=1}^{q} \lambda_{jk} \|b_{jk}\|_1,$$

where $B_k = (b_{1k}, \ldots, b_{qk})$.

Given $B_k^s$, compute $$P_{ik}^s = \begin{cases} 0.5 + \min\{0.5, \frac{s}{T(S-T)}\}, & \|z_i - x_i^T B_k\|_2^2 \leq \tau \|z_i\|_2^2 \\ 0.5 - \min\{0.5, \frac{s}{T(S-T)}\}, & \text{otherwise}, \end{cases}$$

where $T$ was taken as $0.2S$ and $\tau \in (0, 1)$ for $i = 1, \ldots, n$.

end end

Algorithm 2: All-plaid

FIG. 18

PRECISION THERAPEUTIC BIOMARKER SCREENING FOR CANCER

CROSS REFERENCE TO RELATED APPLICATION

This application claims priority to U.S. Provisional Application No. 62/368,997, entitled Precision Therapeutic Biomarker Screening for Cancer, and filed Jul. 29, 2016, which is incorporated herein by reference in its entirety.

FIELD OF THE DISCLOSURE

The present disclosure relates generally to precision treatment of cancer tissue and therapeutic biomarker screening, and, more particularly, to techniques screening biomarkers based on an overlapping cluster grouping technique.

BACKGROUND

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

The use of drugs to selectively target specific genetic alterations in defined patient subpopulations has seen significant successes. One example can be found in the treatment of chronic myeloid leukemia (CML) where the first consistent chromosomal abnormality associated with a human cancer was identified back in the 1960s. Fast forward to the 1980s where the consequence of this abnormality was discovered to be the production of an abnormal gene called BCR-ABL. Intense drug discovery programs were initiated to shut down the activity of BCR-ABL, and in 1992, imatinib (Gleevec) was developed. In 1998, the drug was tested in CML patients who had exhausted standard treatment options and whose life expectancy was limited, with remarkable results in their blood counts returning to normal. In 2001, the FDA approved imatinib. The result, a once commonly fatal cancer now has a five-year survival rate of 95% (Druker, Guilhot, O'Brien, Gathmann, Kantarjian, Gattermann, Deininger, Silver, Goldman, Stone et al. 2006).

Achievements like this largely inspire today's high throughput studies of linking cancer drugs (known or in development) to specific genomic changes which could be used as therapeutic biomarkers. The hope is that such analyses will shed light on biological mechanisms underlying drug sensitivity, tumor resistance and potential drug combination synergies. Such discoveries not only motivate development of precision cancer therapies, improvements of current therapies, and explorations of new therapeutic avenues, they also guide early developments of new cancer drugs (Garnett, Edelman, Heidorn, Greenman, Dastur, Lau, Greninger, Thompson, Luo, Soares et al. 2012; Barretina, Caponigro, Stransky, Venkatesan, Margolin, Kim, Wilson, Lehar, Kryukov, Sonkin et al. 2012).

Cancer cell lines have frequently been used as a convenient way of conducting such studies. For a systematic search of therapeutic biomarkers to a variety of cancer drugs, Garnett et al. (2012) screened 639 human tumor cell lines which represent much of the tissue-type and genetic diversity of human cancers with 130 drugs. These drugs, including approved drugs, drugs in development as well as experimental tool compounds, cover a wide range of targets and processes involved in cancer biology. In the Garnett et al. work, a range of 275-507 cell lines were screened for each drug. The effect of a 72 h drug treatment on cell viability was used to derive measures of drug sensitivity, including the half-maximal inhibitory concentration ($IC_{50}$). In addition, the cell lines underwent sequencing of 64 known cancer genes, genome-wide analysis of copy number gains and losses, and expression profiling of 14,500 genes.

In analysis of this data, Garnett et al. used multivariate analysis of variance (MANOVA) to examine pairwise drug-(genomic) feature associations. This process largely limits knowledge discovery in that: 1) only categorical features can be used as a result over 95% of the features were not examined; 2) the drug-feature associations can change dramatically by considering other features' impacts, hence the marginal associations rarely reflect true relationships. It is more likely that sensitivity of cancer cells to drugs depends on a multiplicity of genomic and epigenomic features with potential interactions. Therefore linear regression with an elastic-net penalty (Zou and Hastie 2005) was further applied to each drug to identify significantly related features while adjusting for other effects.

However given the degree of complexity of the data, this later elastic-net regression applied for each drug was far from sufficient. Firstly, the 639 tumor cell lines came from a variety of cancer tissue types, hence there is likely additional heterogeneity manifested as subpopulations in data. Secondly, the 130 drugs are hardly independent with each other. It has long been recognized that one can improve the prediction performance by modeling with multiple response variables (Breiman and Friedman 1997).

SUMMARY OF THE INVENTION

As a result of the foregoing shortcomings in the state of the art, the present application addresses some direct questions of interest. These include, i) can cancer-specific therapeutic biomarkers be detected, ii) can drug resistance patterns be identified along with predictive strategies to circumvent resistance using alternate drugs, and iii) can biomarkers of combination therapies be identified to help predict synergies in drug activities?

To address these questions a number of statistical challenges exist: i) therapeutic biomarkers of drug sensitivity cluster among the cell lines; ii) clusters can overlap (e.g. a cell line may belong to multiple clusters); and iii) can a multivariate framework be developed so that drugs can be modeled jointly.

The present application describes new statistical modeling techniques that address these issues using a finite mixture of multivariate regression (FMMR) model generalized to enable overlapping clustering and the numerical solutions of drug data, genomic data, biomarker data, demographic data, pathology data (e.g., cell line data, etc.).

In accordance with an example, a method of identifying alternative drug therapies, the method comprises: receiving, at a processing unit, drug responsiveness data for a treatment drug applied to a plurality of different cell lines, each cell line differing in genomic profile from one another such that the genomic profiles for the plurality of different cell lines are mutually exclusive, the drug responsiveness data being determined from live cell testing using the treatment drug; identifying at least two cell lines from the plurality of different cell lines, and determining, at the processing unit, an overlap cell line cluster where one of the at least two cell lines has a high drug responsiveness value and another of the at least two cell lines has a low drug responsiveness value, and wherein the overlap cell line cluster has a drug responsiveness value for the treatment drug that is between the high drug responsiveness value and the low drug responsiveness value, wherein determining the overlap cell line cluster using a generalized finite mixture of multivariate regression (FMMR) model; performing, at the processing unit, an optimality algorithm process on data for a cluster of drugs to identify one or more alternative drugs exhibiting a drug responsiveness value between the high drug responsiveness value and the low drug responsiveness value; and administering to cells of one of the at least two cell lines the one or more alternative drugs.

In accordance with another example, a method of grouping drugs for treating a pathology, the method comprises: receiving, at a processing unit, drug responsiveness data for a set of drugs and for a set of cell lines; grouping, using the processing unit, each of the drugs into a different drug grouping, using (i) a generalized finite mixture of multivariate regression (FMMR) model as follows $$f(y_i | x_i, \Theta) = \sum_{(l_1 \ldots l_s) \in T} \pi(l_1 \ldots l_s) f(y_i | x_i, B_{l_1}, \ldots, B_{l_s}, \Sigma).$$

wherein $f(y_i | x_i, B_{l_1}, \ldots, B_{l_s}, \Sigma)$ is a multivarite normal density function generalized for both non-overlapping clusters and overlapping clusters, $y_i$ are drug responsiveness values, $x_i$ are genomic biomarkers, $B_{l_1}, \ldots, B_{l_s}$ are coefficient matrix values for a cluster, $l_1 \ldots l_s$, are clusters, $\pi$ is an observation value indicating whether a drug belongs in a grouping ($\pi=1$) or not ($\pi=0$), and $\Sigma$ is an error term for the coefficient matrix values, i represents a drug, wherein the generalized FMMR model allows for modeling drugs for both non-overlapping clusters and overlapping clusters, and (ii) a clustering algorithm configured to group drugs based on the coefficient matrix values, B, for different drugs and based on cell line assignments; and administering one or more drugs from one of the drug groupings to a cell line expressing the pathology.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

FIG. 16 illustrates Table 1 showing sensitive versus drug resistant drugs for soft tissue cancer, identified by the drug analysis system of FIG. 15, in accordance with an example.

FIG. 17 illustrates a plaid model Algorithm 1, in accordance with an example.

FIG. 18 illustrates a all-plaid model Algorithm 2, in accordance with an example.

DETAILED DESCRIPTION

Figure 1:
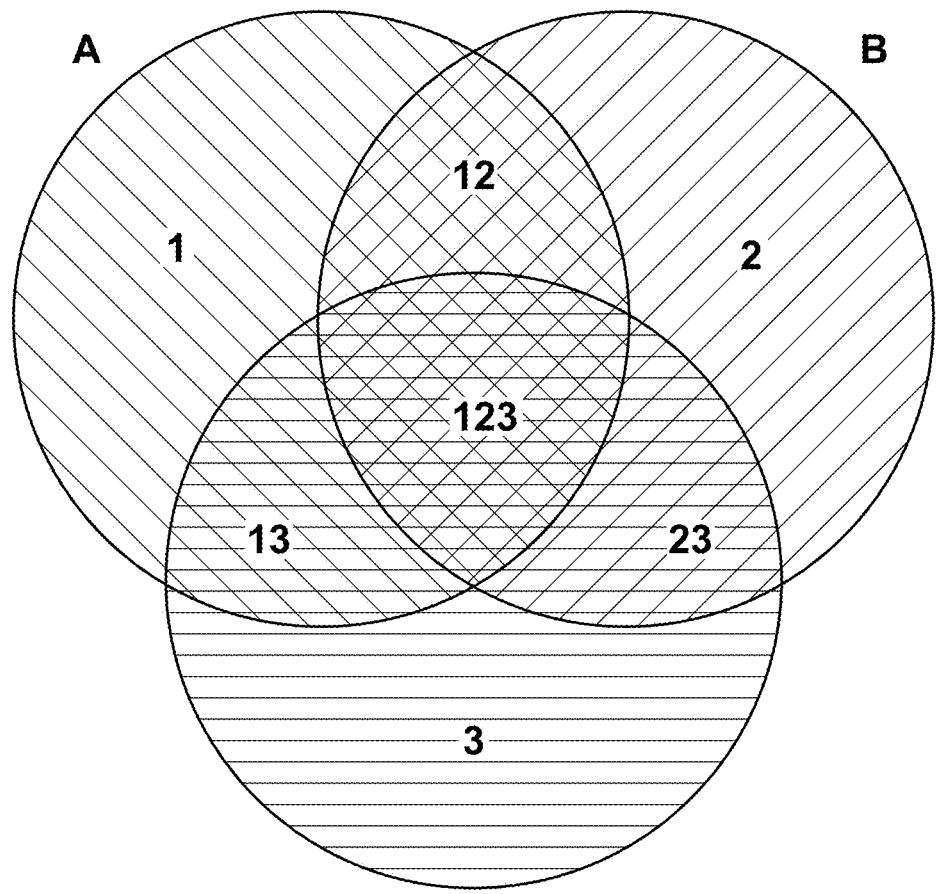
FIG. 1 illustrates a plurality (K=3) object clusters, showing that clusters can overlap resulting in $2^K-1$ overlapping patterns.
Figure 2A:
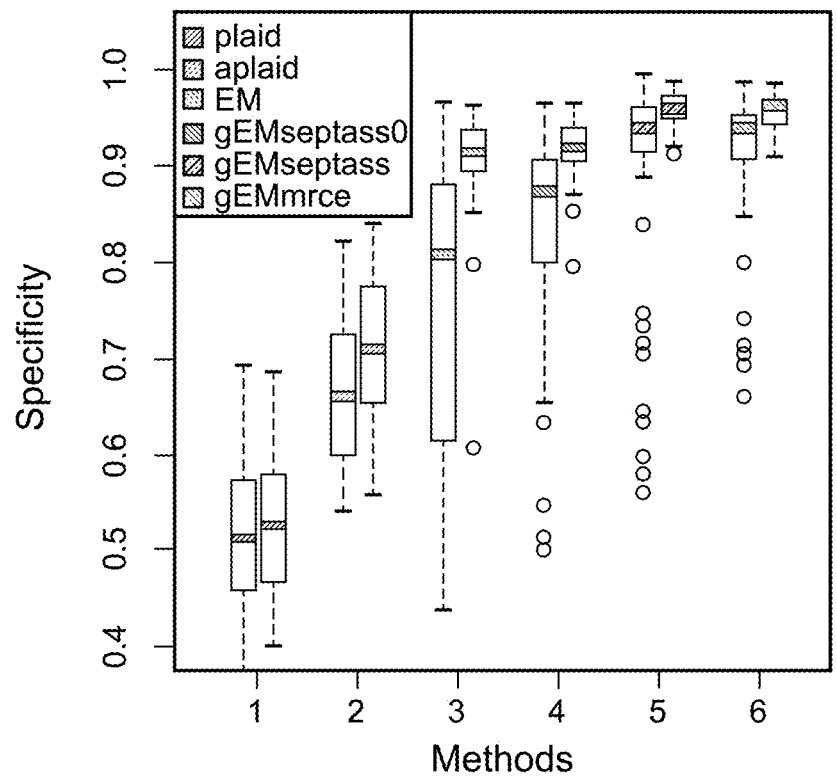
FIGS. 2A and 2B illustrate specificity measurement results for an example first analyzed scenario where there are no overlapping clusters, showing that techniques herein retain capture the un-overlapping clusters.
Figure 2B:
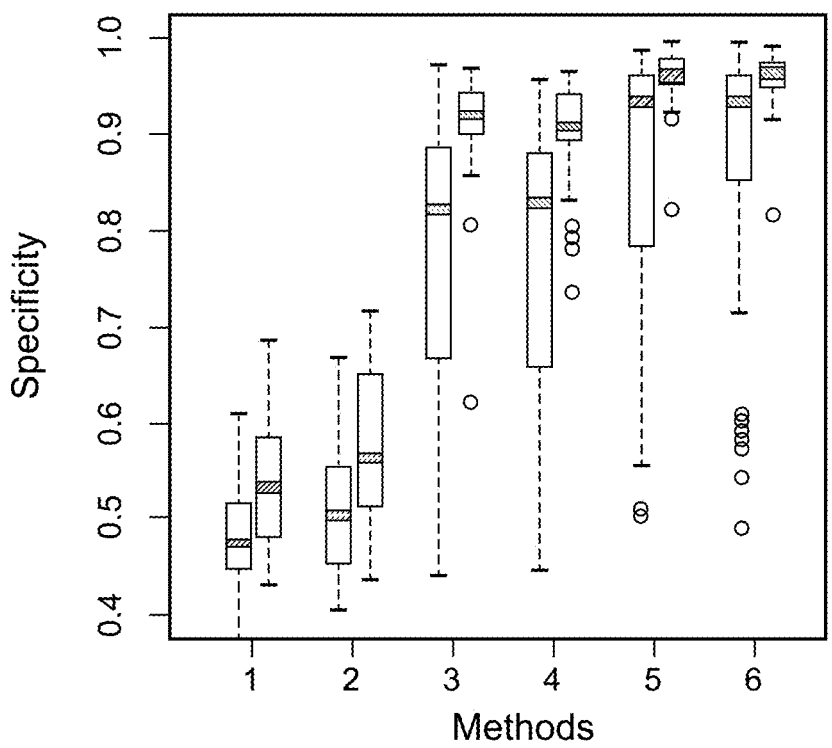
Figure 2C:
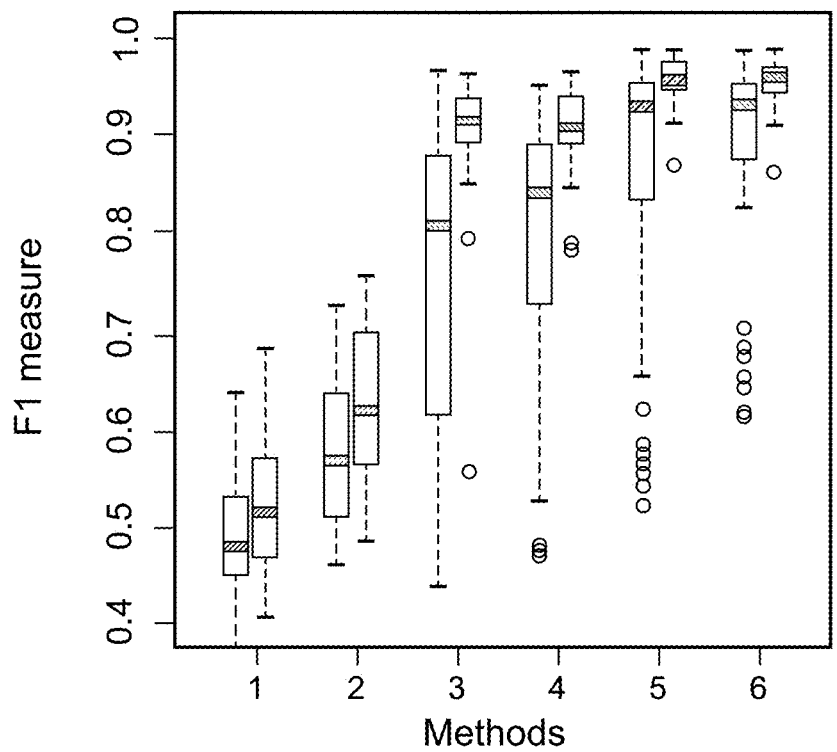
FIG. 2C illustrates F1 measurements for this first analyzed scenario.
Figure 2D:
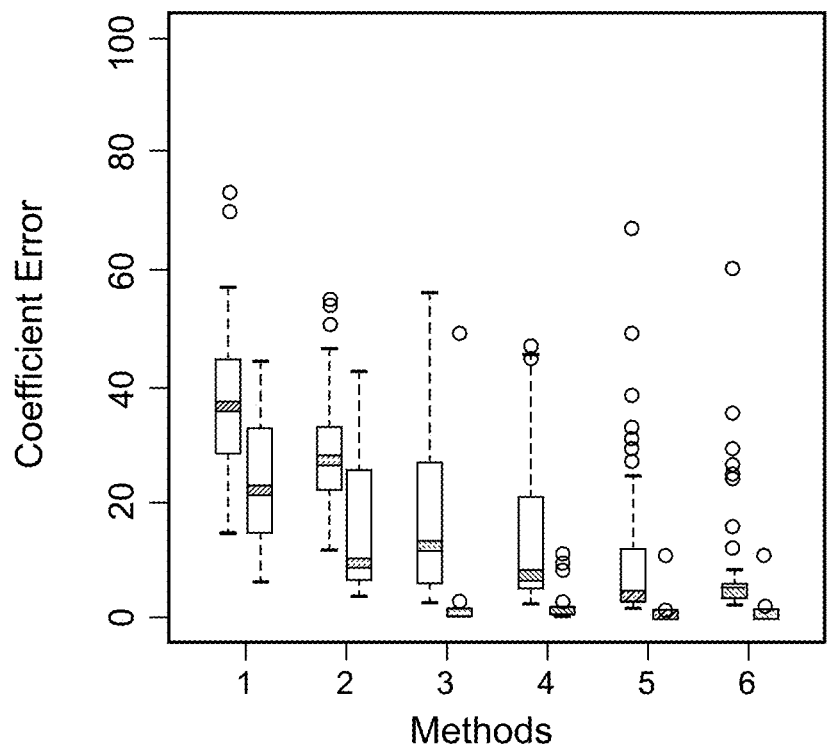
FIG. 2D illustrates a coefficient error for this first analyzed scenario.
Figure 3A:
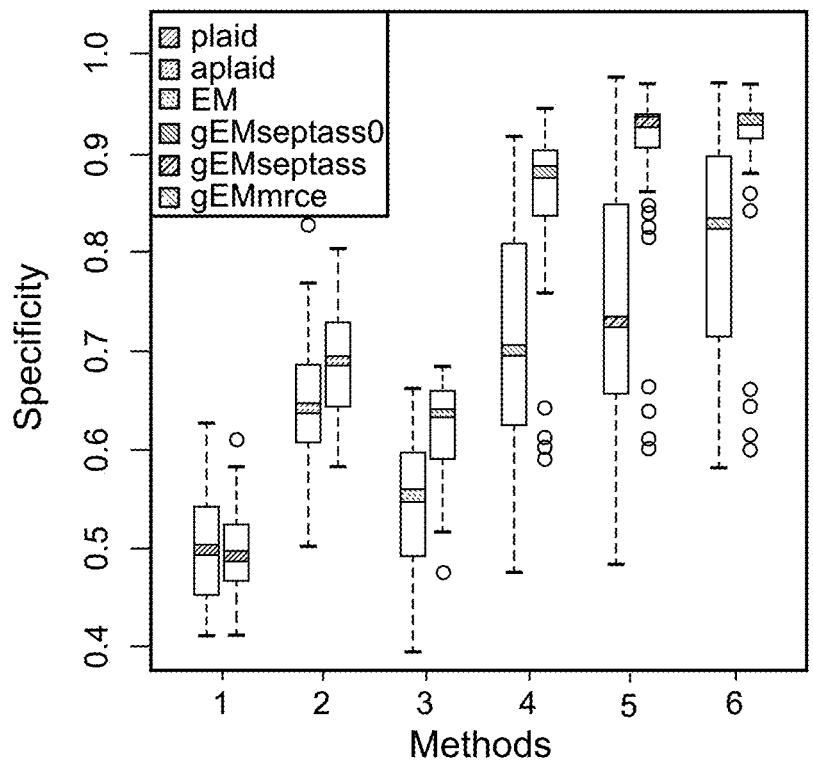
FIGS. 3A and 3B illustrate specificity measurement results for an example second analyzed scenario where there are (30%) overlapping clusters.
Figure 3B:
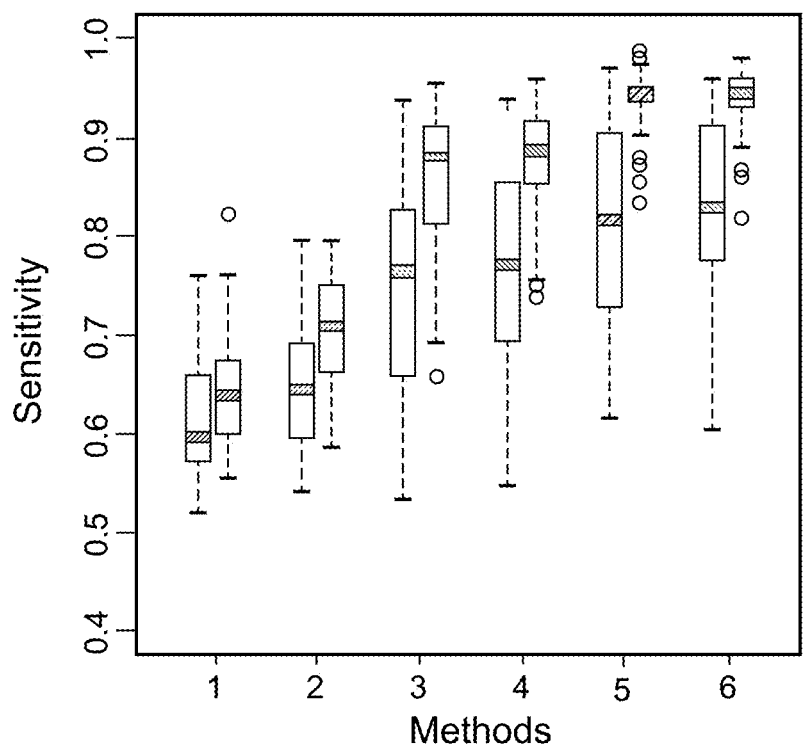
Figure 3C:
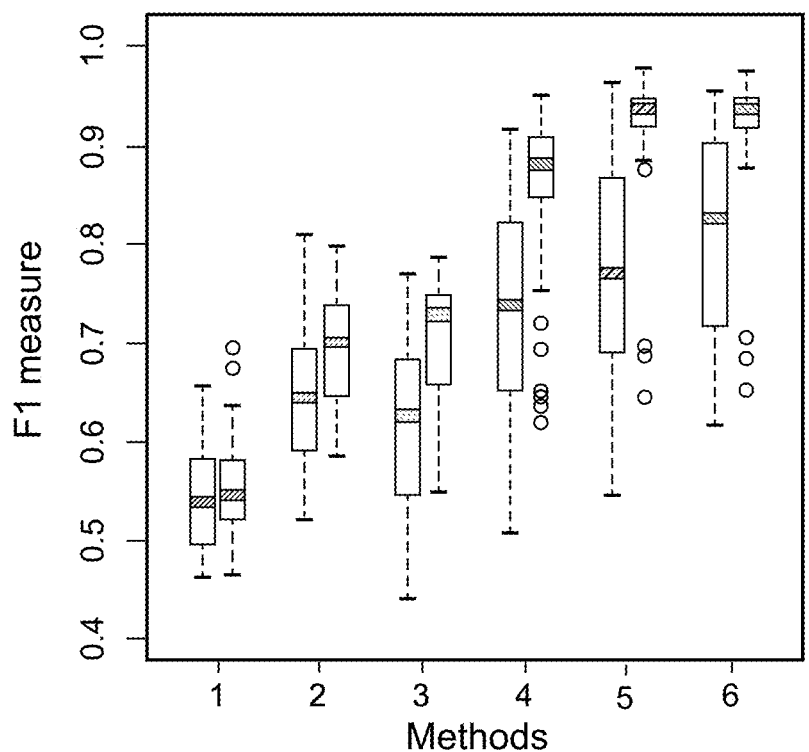
FIG. 3C illustrates F1 measurements for this second analyzed scenario.
Figure 3D:
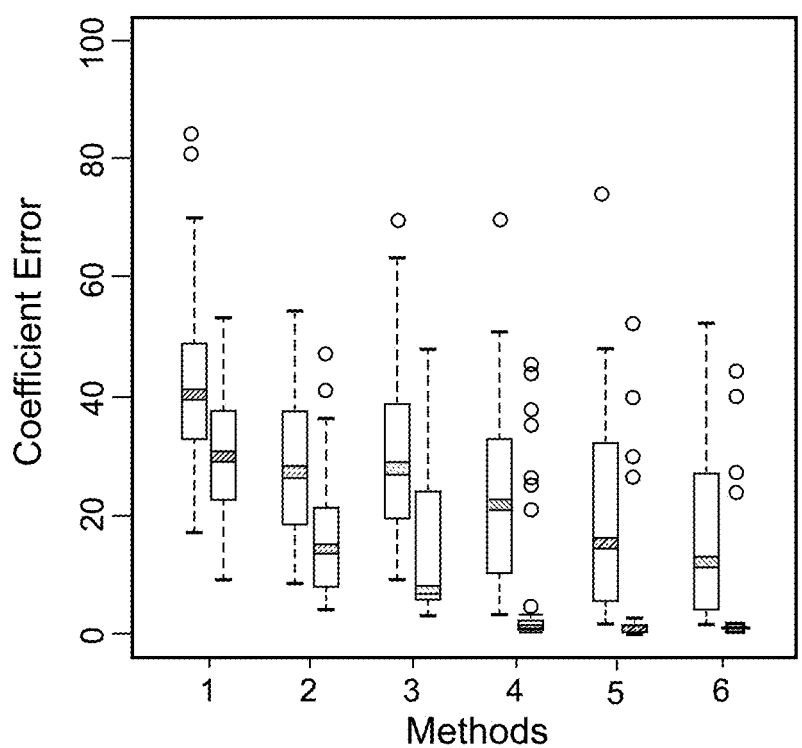
FIG. 3D illustrates a coefficient error for this second analyzed scenario.

The present techniques provide computer-implemented processes for precision therapeutic biomarker screening for cancer. The techniques use a model-based overlapping clustering framework to assess large numbers of possible drugs and drug combinations against patient data, including cell line responsiveness, genetic data, phenotype data, demographic data, etc. A multivariate regression model has been developed, along with a latent overlapping cluster indicator variable. The techniques employ a new finite mixture of multivariate regression (FMMR) model and EM algorithm for modeling. The techniques have been used to analyze large amounts of drug data and have identified complex overlapping drug clusters, as well as cluster-wise drivers that facilitate identification of new drugs for treating pathologies, such as cancer, in patients.

Clustering is a well-established statistical technique which involves grouping data elements according to a measure of similarity. Traditional clustering techniques generate partitions so that each data element belongs to one and only one cluster. It has long been recognized that such an ideal clustering seldom exists in real data. It is more likely that clusters overlap in some parts.

Some statistical methods have been developed to handle the overlapping clustering problem. Lazzeroni and Owen (2002), for example, put forward the so-called plaid model for two-sided overlapping clustering of gene expression data. However, the numerical solutions proposed in the paper can produce unsatisfactory cluster retrieval results (see Turner, Bailey and Krzanowski (2005) and Turner, Bailey, Krzanowski and Hemingway (2005) for improved and extended (to structured data) plaid models, and see, Zhang (2010) for the Bayesian plaid model formulation). Segal, Battle and Koller (2002) introduced a probabilistic model for one-sided overlapping clustering. Banerjee, Krumpelman, Ghosh, Basu and Mooney (2005) later generalized this probabilistic model to any regular exponential family distribution. However both of the methods suffer from computational complexity in estimating a binary membership matrix $M \in \{0, 1\}^{n \times K}$, which is an integer optimization problem.

An alternative "naive" overlapping clustering method is the finite mixture (FM) model with a hard threshold a on cluster membership probabilities. This approach assigns a data point to a cluster k if $P(z_{ik}=1|X_i, \Theta) > \alpha$ and hence enables an item to belong to multiple clusters.

As pointed out by Banerjee et al. (2005), this conventional FM method is problematic because: 1) it is hard to choose the value of a; and 2) it is not a natural generative model for overlapping clustering since one underlying assumption of the mixture model is that each object comes from only one mixture component. Later Fu and Banerjee (2008) introduced an overlapping clustering approach based on the multiplicative mixture model (Heller and Ghahramani 2007). However, this model ended up with the same computational issue as in Banerjee et al. (2005).

Some have focused on investigating the relationship between response variables $Y \in \mathbb{R}^q$ and covariates $X \in \mathbb{R}^p$ by fitting a regression model rather than to explore the X or Y on its own. In the context of regression analysis for q=1, finite mixture of regression (FMR) models are commonly used to capture unobserved cross-sectional heterogeneity in the data (see, e.g., Jedidi, Ramaswamy, DeSarbo and Wedel 1996). The FMR model postulates that a sample of observations come from a finite mixture of latent sub-populations with each sub-population represented by a specific regression model.

In 1972, Quandt proposed a two component mixture of univariate Gaussian linear regression model with the idea of using maximum likelihood function to estimate model parameters. Subsequently, the well-known expectation-maximization (EM) algorithm was used for maximum likelihood estimation (MLE) with incomplete data, revolutionizing studies of the FMR model, with various researchers contributing the advancing efforts.

However, looking at each of these conventional techniques, the results insufficient for true therapeutic applications, especially as data sets grow in size and complexity. Notably, none of these conventional techniques offer a truly generalized model, one that provides for overlapping (i.e., clustering) data sets for optimized variable selection. Data distributions depart from expected normality. In terms of statistical accuracy, breakdowns occur from forced approximations, such as setting mixture components as a constant. But most importantly, none of the above listed methods allow for simultaneous variable selection. In order to do variable selection, these data models were constrained to the point where response variables were treated as independent from one another. Yet, clinical testing shows, especially for pathologies like various cancers, that selection variables can be interdependent. Therefore, these proposed techniques are not suitable for cancer drug screening.

Overcoming these and other limitations of conventional techniques, with the advanced techniques described herein, we are able to show that biomarkers indicative of a first pathology, say soft tissue cancer, may well have demonstrated drug treatments that alone or combined with other drug treatments may be used to treat a second pathology, such as cancer in the bone or kidney.

The present techniques provide, among other things, a computer-implemented process using a model-based overlapping clustering framework. As detailed in examples below, a multivariate regression model is provided and a latent overlapping cluster indicator variable is introduced. The present techniques employ a new finite mixture of multivariate regression (FMMR) model and expectation-maximization (EM) algorithm to fit the new model. Penalized likelihood with a lasso, Elastic-Net, or other penalty function may be used to estimate model parameters meanwhile allowing variable selection. Simulation studies show excellent finite-sample performance that outperforms other methods. Analysis of drug data, for example, has found complex overlapping drug clusters as well as cluster-wise drivers that facilitate identification of new drugs for treating pathologies such as cancer.

As we discuss, the present techniques are able to assess multiple variables across cancer cell line targets to record drugs and drug combinations for treatment.

For a sample (of cell lines) of n observations, denote $y_i=(y_{i1}, \ldots, y_{iq})^T \in \mathbb{R}^q$ a vector of responses (IC$_{50}$ values), $x_i=(x_{i1}, \ldots, x_{ip_n})^T \in \mathbb{R}^{p_n}$ a vector of predictors (genomic markers) and $\varepsilon=(\varepsilon_{i1}, \ldots, \varepsilon_{iq})^T$ a vector of random errors for the ith observation. Assume $$\varepsilon_i \stackrel{iid}{\sim} N_q(0, \Sigma)$$

for i=1, ..., n. The following allows overlapping clustering of cell lines within the context of a multivariate regression model, $$y_i = \sum_{k=1}^{K} B_k^T x_i P_{ik} + \varepsilon_i, \quad i = 1, \ldots, n, \quad (2.1)$$

where K is the total number of clusters, $B_k$ is a $p_n \times q$ coefficient matrix for the kth cluster, and is $P_{ik} \in \{0, 1\}$ if observation i belongs to the kth cluster, otherwise 0. In traditional clustering problem, it assumes that each observation belongs to exactly one cluster, namely $\Sigma_{k=1}^K P_{ik}=1$ for all i. Therefore we allow $\Sigma_{k=1}^K P_{ik} \geq 1$ so that each observation can belong to multiple clusters.

We provide some interpretation of the clusters in model (2.1). A cluster k in the model contains a subset of observations for whom $P_{ik}=1$. We will assume that not all genomic feature are relevant in describing the cluster of observations and thus will assume a sparse coefficient matrix $B_k$. Since the sparse pattern can vary with k, each cluster can be represented by a unique set biomarkers. For samples belonging to multiple clusters, their response variables are explained by multiple sets of biomarkers, indicative of involving several biological processes simultaneously.

We examined two approaches for fitting (2.1): a generalized finite mixture of multivariate regressions model and a generalization of the plaid model previously discussed.

Estimation Procedure

Finite Mixture of Multivariate Linear Regression

When $\Sigma_{k=1}^K P_{ik}=1$, model (2.1) can be characterized by a hierarchical structure which ends up with an FMMR model. Consider a latent cluster membership random variable $z_i$ for observation i. Given $\Sigma_{k=1}^K P_{ik}=1$, the range of $z_i$ equals to $\{1, \ldots, K\}$. Assume that $P(z_i=k)=\pi_k$ for each k. By properties of probability, it satisfies that $\Sigma_{k=1}^K \pi_k=1$ and $\pi_k \geq 0$. Moreover for model (2.1), it has $$(y_i|z_i=k, x_i, B_k, \Sigma \sim N_q(B_k^T x_i, \Sigma). \quad (3.1)$$

Denote $\Theta=(B_1, \ldots, B_K, \Sigma, \pi)$ with $\pi=(\pi_1, \ldots, \pi_{K-1})^T$. We can derive the joint density of $y_i$ and $z_i$ as $$f(y_i, z_i | x_i, \Theta) = \prod_{k=1}^K \{\pi_k f(y_i | x_i, B_k, \Sigma)\}^{I(z_i=k)}, \quad (3.2)$$

where $f(y_i|x_i, B_k, \Sigma, \pi)$ is a multivariate normal density function defined in (3.1).

Summarizing (3.2) over $z_i=1, \ldots, K$ yields the FMMR model $$f(y_i | x_i, \Theta) = \sum_{k=1}^K \pi_k f(y_i | x_i, B_k, \Sigma). \quad (3.3)$$

When using the EM algorithm to estimate model (3.3), $(x_i; y_i)$ is regarded as an incomplete sample observation for missing cluster membership variable $z_i$, one instead deals with the joint density of (3.2) with complete data. The complete (conditional) log-likelihood of $\Theta$ given a sample of n independent observations from model (2.1) becomes $$l_n(\Theta) = \sum_{i=1}^n \sum_{k=1}^K z_{ik} \log \pi_k + \sum_{i=1}^n \sum_{k=1}^K z_{ik} \log f(y_i | x_i, B_k, \Sigma), \quad (3.4)$$

where $z_{ik}=I(z_i=k)$.

Variable selection, to obtain a parsimonious model, is essential especially to high dimensional statistical modeling for enhanced scientific discovery and improved prediction accuracy (Fan and Li 2006). Khalili and Chen (2012) introduced a penalized likelihood approach for variable selection in FMR models, which was shown to be variable selection consistent and computationally much more efficient than all-subset selections. Similarly, we derived a penalized log-likelihood of $\Theta$ as $$\tilde{l}_n(\Theta)=l_n(\Theta)-\rho_n(\Theta), \quad (3.5)$$

where $$\rho_n(\Theta) = \sum_{k=1}^K \pi_k \rho_{nk}(B_k).$$

The following two penalty functions were used to meet different demands in variable selection:
1) the $L_1$-penalty in LASSO (Tibshirani 1996) for simultaneous estimation and variable selection $$\rho_{nk}(B_k)=\lambda_k \|B_k\|_1$$

2) a linear combination of the L1- and L2-penalty in Elastic-Net (Zou and Hastie, 2005) for simultaneous estimation and selection of grouped features $$\rho_{nk}(B_k)=\lambda_k^1 \|B_k\|_1 + \lambda_k^2 \|B_k\|_2^2,$$

where $\|\cdot\|_1$ and $\|\cdot\|_2$ are respectively the $L_1$- and $L_2$-norms and the tuning parameters $\lambda_k, \lambda_k^1 \lambda_k^2 \geq 0$.

In next section, revised FMMR model and EM algorithm are devised for overlapping clustering multivariate regression data.

Generalized FMMR Model and EM Algorithm for Overlapping Clustering

The FMMR model solves (2.1) given $\Sigma_{k=1}^K P_{ik}=1$ for each i, for each i, wherein the clusters are partitional. When the clusters are overlapping, namely $\Sigma_{k=1}^K P_{ik} \geq 1$, we propose a generalized FMMR model to address the issue, meanwhile this generalized model preserves the ability in fitting partitions.

Suppose we have K objective clusters indexed by 1 to K. Note that these clusters can overlap with each other, resulting in $2^K-1$ types of overlapping patterns. Let K equal to 3 for an example, the overall overlapping patterns are composed of S={1; 2; 3; 12; 13; 23; 123}. Here element 12 in S represents exclusively the overlapping part of objective clusters 1 and 2, whereas element 1 represents a subset of objective cluster 1 which does not have overlappings with all other objective clusters. FIG. 1 illustrates the particular part each overlapping pattern in S represents. By definition, overlapping patterns in S are mutually exclusive. And each observation i from (2.1), given $\Sigma_{k=1}^K P_{ik} \geq 1$, belongs to one and only one overlapping pattern of S.

We define 2K−1 hypothetical clusters. Each hypothetical cluster (called "cluster" herein) indicates an overlapping pattern defined above and is indexed by an element in T wherein $$T=\cup_{s=1}^K \{(l_1 \ldots l_s): \{l_1, \ldots, l_s\} \subseteq \{1, \ldots, K\}\},$$

Cluster $(l_1 \ldots l_s)$ implies that its members belong to objective clusters $l_1, \ldots, l_s$.

We introduce a latent cluster membership random variable $z_i$ for observation i from (2.1), and characterize model (2.1) by a hierarchical structure. Given $\Sigma_{k=1}^K P_{ik} \geq 1$, the range of $z_i$ becomes the set T. We further postulate that $$P(z_i=l_1 \ldots l_s))=\pi_{(l_1 \ldots l_s)}. \quad (3.6)$$

By properties of probability, vector $\pi=(\pi_{(l_1 \ldots l_s)\in T})^T$ satisfies that $$\sum_{(l_1 \ldots l_s)\in T} \pi_{(l_1 \ldots l_s)} = 1, \pi_{(l_1 \ldots l_s)} \geq 0.$$

Moreover for (2.1), it amounts to $P_{il_1}, \ldots, P_{il_s}=1$ given $z_i=(l_1 \ldots l_s)$, Hence it has $$(y_i | z_i = (l_1 \ldots l_s), x_i, \{B_k\}_{k=l_1}^{l_s}, \Sigma) \sim N_q\left(\sum_{k=l_1}^{l_s} B_k^T x_i, \Sigma\right). \quad (3.7)$$

Let $\Theta=(B_1, \ldots, B_K, \Sigma, \pi)$. By (3.6) and (3.7), the joint density of $y_i$ and $z_i$ equals to $$f(y_i, z_i | x_i, \Theta) = \qquad (3.8)$$
$$\prod_{(l_1 \ldots l_s)\in T} \{\pi_{(l_1 \ldots l_s)} f(y_i | x_i, B_{l_1}, \ldots, B_{l_s}, \Sigma)\}^{I(z_i=(l_1 \ldots l_s))},$$

where $f(y_i|x_i, B_{l_1}, \ldots, B_{l_s}, \Sigma)$ is a multivariate normal density function defined in (3.7).

By summarizing (3.8) over $z_i$, we obtain a generalized FMMR model $$f(y_i | x_i, \Theta) = \sum_{(l_1 \ldots l_s)\in T} \pi_{(l_1 \ldots l_s)} f(y_i | x_i, B_{l_1}, \ldots, B_{l_s}, \Sigma). \quad (3.9)$$

Note that if $\pi_{(l_1 \ldots l_s)}=0$ for $s>1$, (3.9) reduces to traditional FMMR models in (3.3).

For a sample of n independent observations from model (2.1), the complete (conditional) log-likelihood of $\Theta$ becomes $$l_n(\Theta) = \sum_{i=1}^n \sum_{(l_1 \ldots l_s)\in T} z_{i,(l_1 \ldots l_s)} \log \pi_{(l_1 \ldots l_s)} +$$
$$\sum_{i=1}^n \sum_{(l_1 \ldots l_s)\in T} z_{i,(l_1 \ldots l_s)} \log f(y_i | x_i, B_{l_1}, \ldots, B_{l_s}, \Sigma),$$

where $z_{i,l(l_1 \ldots l_s)} = I(z_i=(l_1 \ldots l_s))$.

We derived a penalized log-likelihood of $\Theta$ which enforces sparsity in genomic features.

$$\tilde{l}_n(\Theta) = l_n(\Theta) - \sum_{k=1}^K \sum_{\substack{(l_1 \ldots l_s) \\ k\in\{l_1, \ldots, l_s\}}} \pi_{(l_1 \ldots l_s)} p_{nk}(B_k), \quad (3.10)$$

where $p_{nk}(B_k)$ utilizes one of two penalty functions, the LASSO penalty ($\rho_{nk}(|B_k|)=\lambda_k \|B_k\|_1$) or the Elastic-Net penalty $$(\rho_{nk}(|B_k|) = \lambda_k^1 \|B_k\|_1 + \lambda_k^2 \|\mathbf{B}\|_2^2.)$$

for grouped features as defined herein. The notation $$\sum_{\substack{(l_1 \ldots l_s) \\ k\in\{l_1, \ldots, l_s\}}}$$

implies that it summarizes over $(l_1 \ldots l_s)\in T$ for which $k\in\{l_1, \ldots, l_s\}$. In (3.10), $B_k$ is a coefficient matrix corresponding to the kth objective cluster. The penalty imposed on $B_k$ is proportional to $$\sum_{\substack{(l_1 \ldots l_s) \\ k\in\{l_1, \ldots, l_s\}}} \pi_{(l_1 \ldots l_s)}$$

which depicts the proportion of observations involving in the kth objective cluster. This is a strategy of relating the penalty to sample sizes similar to Khalili and Chen (2012) for enhanced power of the method.

Numerical Solution to the Generalized FMMR Model

A new expectation maximization (EM) algorithm to maximize the penalized log-likelihood in ($\tilde{l}_n(\Theta)$) (3.10) with a LASSO penalty function. Due to the additive property for overlapping clusters, each $B_k$ involves in multiple clusters. Therefore coefficient matrix $B_k$ for k=1; : : : ; K cannot be optimized independently within each cluster like in usual EM algorithm for FMR models. Instead we sequentially update each $B_k$ given the rest is known. Specifically, the revised EM algorithm iteratively maximizes the $\tilde{l}_n(\Theta)$ in following two steps:

E-step: Given $\Theta^m$, estimate $\hat{z}_{i,(l_1 \ldots l_s)}^m$ with its posterior probability by applying the Bayes' rule to (3.8) and (3.9), $$\hat{P}(z_{i,(l_1 \ldots l_s)}^m = 1 | y_i, x_i, \Theta^m) =$$
$$\frac{\pi_{(l_1 \ldots l_s)}^m f(y_i | x_i, B_{l_1}^m, \ldots, B_{l_s}^m, \Sigma^m)}{\sum_{(l_1' \ldots l_s')\in T} \pi_{(l_1' \ldots l_s')}^m f(y_i | x_i, B_{l_1'}^m, \ldots, B_{l_s'}^m, \Sigma^m)}$$

for i=1, ..., n and $(l_1 \ldots l_s)\in T$.

M-step: Given $Z^m = (\hat{z}_{i,(l_1 \ldots l_s)}^m)$, update the mixing proportions $\pi^{m+1}$ by $$\pi_{(l_1 \ldots l_s)}^{m+1} = \frac{1}{n}\sum_{i=1}^n z_{i,(l_1 \ldots l_s)}^m$$

for $(l_1 \ldots l_s)\in T$. Note that this is obtained by maximizing the leading term of (3.10) with respect to $\pi$ for simplicity. This simplified updating scheme however works well in simulation studies.

Given $Z^m$, $\pi^{m+1}$ and $\Sigma^m$, sequentially update $B_k^{m+1}|\{B_{s,s\neq k}^m\}$ by $$B_k^{m+1} = \max_{B_k} \sum_{i=1}^n \sum_{\substack{(l_1 \ldots l_s) \\ k\in\{l_1, \ldots, l_s\}}} z_{i,(l_1 \ldots l_s)}^m \log f(y_i | x_i, \{B_l^m\}_{l=l_1, l\neq k}^{l_s}, \Sigma^m) - \quad (3.11)$$
$$\sum_{\substack{(l_1 \ldots l_s) \\ k\in\{l_1, \ldots, l_s\}}} \pi_{(l_1 \ldots l_s)}^{m+1} \lambda_k \|B_k\|_1,$$

for k=1, ..., K.

According to (3.7), $y_i$ for i=1, ..., n are i.i.d. in multivariate normal. Hence (3.11) becomes $$B_k^{m+1} = \min_{B_k} \sum_{i=1}^n \sum_{\substack{(l_1 \ldots l_s) \\ k \in \{l_1, \ldots, l_s\}}} z_{i,(l_1 \ldots l_s)}^m \tag{3.12}$$
$$(y_i^* - B_k^T x_i)^T (\Sigma^m)^{-1} (y_i^* - B_k^T x_i) +$$
$$2 \sum_{\substack{(l_1 \ldots l_s) \\ k \in \{l_1, \ldots, l_s\}}} \pi_{(l_1 \ldots l_s)}^{m+1} \lambda_k \|B_k\|_1,$$
$$= \min_{B_k} \sum_{\substack{(l_1 \ldots l_s) \\ k \in \{l_1, \ldots, l_s\}}} tr\big((Y^* - XB_k)^T z_{(l_1 \ldots l_s)}^m\big)$$
$$(Y^* - XB_k)(\Sigma^m)^{-1}) + 2 \sum_{\substack{(l_1 \ldots l_s) \\ k \in \{l_1, \ldots, l_s\}}} \pi_{(l_1 \ldots l_s)}^{m+1} \lambda_k \|B_k\|_1,$$

where $y_i^* = y_i - \sum_{l \in (l_1, \ldots, l_s) \backslash k} (B_l^m)^T x_i,$ $Y^* = (y_1^*, \ldots, y_n^*)$ and $z_{(l_1 \ldots l_s)}^m = \text{diag}(z_{1,(l_1 \ldots l_s)}^m, \ldots, z_{n,(l_1 \ldots l_s)}^m).$ Optimization of (3.12) is a multivariate regression problem with a LASSO penalty for estimation, which can be solved by the MRCE algorithm (Rothman, Levina and Zhu 2010). If we ignore the covariance structure of $\Sigma^m$ in (3.12), the optimization reduces to q independent LASSO regression problems. In this case, more complex penalty functions say the Elastic-Net or the fused LASSO penalty can be easily applied. Therefore we also investigated the performance of this simplified strategy in simulation studies, and found the present techniques work surprisingly well comparable, in terms of clustering accuracy, to the original method utilizing the MRCE algorithm.

Given $Z^m$ and $\{B_k^{m+1}\}_{k=1}^K$, update $\Sigma^{m+1}$ by (3.13)

$$\Sigma^{m+1} = \max_\Sigma \sum_{i=1}^n \sum_{(l_1 \ldots l_s) \in T} z_{i,(l_1 \ldots l_s)}^m \log f\big(y_i \mid x_i, \{B_l^{m+1}\}_{l=l_1}^{l_s}, \Sigma\big)$$
$$= \min_\Sigma \sum_{i=1}^n \sum_{(l_1 \ldots l_s) \in T} -z_{i,(l_1 \ldots l_s)}^m \log|\Sigma^{-1}| +$$
$$\sum_{(l_1 \ldots l_s) \in T} tr\left(\left(Y - X\sum_{l=l_1}^{l_s} B_l^{m+1}\right)^T z_{(l_1 \ldots l_s)}^m \left(Y - X\sum_{l=l_1}^{l_s} B_l^{m+1}\right) \Sigma^{-1}\right).$$

By taking the derivative of (3.13) according to $\Sigma^{-1}$, we get $$\Sigma^{m+1} = \frac{\sum_{(l_1 \ldots l_s) \in T} \left(Y - X\sum_{l=l_1}^{l_s} B_l^{m+1}\right)^T z_{(l_1 \ldots l_s)}^m \left(Y - X\sum_{l=l_1}^{l_s} B_l^{m+1}\right)}{\sum_{(l_1 \ldots l_s) \in T} \sum_{i=1}^n z_{i,(l_1 \ldots l_s)}^m},$$

where $\Sigma_{(l_1 \ldots l_s) \in T} \Sigma_{i=1}^n z_{i,(l_1 \ldots l_s)}^m = n$.

Although we can also penalize the inverse covariance matrix $\Sigma^{-1}$ in (3.13) like in Rothman et al. (2010), our simulations have shown that penalizing the $\Sigma^{-1}$ results in a lower degree of clustering accuracy than not penalizing the $\Sigma^{-1}$. This is because by penalizing the $\Sigma^{-1}$ one introduces bias in its estimation, and a biased estimate of $\Sigma^{-1}$ in return deteriorates the estimate of $z_i$; $(l_1 \ldots l_s)$ in the E-step. Thus we choose to not penalize the $\Sigma^{-1}$.

Commencing with an initial value $\Theta^0$, the present models may iterate between the E- and M-steps until the relative change in log-likelihood, $|l_n^{m+1}(\hat{\Theta}) - l_n^m(\hat{\Theta}))/(l_n^m(\hat{\Theta}))|$, is smaller than some threshold value, taken as $10^{-5}$ in simulation studies and $10^{-3}$ in real data analysis. Additionally, a cluster, whose mixing proportion is smaller than some threshold value taken as 0.01 in the paper, was removed during iterations to avoid over estimations.

Selection of the Tuning Parameters and K

In preceding penalized likelihood approach, the techniques can choose the sizes of component-wise tuning parameters $\lambda_k$ for k=1, ..., K, which controls the complexity of an estimated model (Fan and Lv 2010). The data-driven method cross-validation (CV) (Stone 1977) is frequently adopted in literature (Tibshirani 1996; Zou and Hastie 2005). In an example, we used a component-wise 10-fold CV method for optimal tuning parameter selection in the expression (3.12).

Selection of the number of components K is performed in finite mixture models (including the FM, FMR and FMMR). In applications, the choice can be based on prior knowledge of data analysts. With respect to formatted methodologies, information criteria (IC) remains by far the most popular strategy for selection of K. See Fraley and Raftery (1998), Anderson and Burnham (2002) and Claeskens, Hjort et al. (2008) for general treatments on this topic. Here we choose the K that minimizes the IC, $$IC_n(K) = -2l_n(\Theta) + N_K a_n. \tag{3.14}$$

In (3.14), $N_k$ is the effective number of parameters in the model with $$N_K = |\{B_k, k=1, \ldots, K\}| + |\pi| - 1 + |\Sigma|,$$

where $|A|$ calculates the number of nonzero elements in A. Also in (3.14), an is a positive sequence depending on n. The well-known AIC (Akaike 1974) and BIC (Schwarz et al. 1978) correspond to $a_n = 2$ and $a_n = \log(n)$ respectively. It has been shown (in Keribin (2000)) that under general regularity conditions, BIC can correctly identify the order of an FM model as n increases to infinity. The feasibility of their results to the FMR or FMMR models is however unknown. However, we have examined the performance of BIC for selection of K in an generalized FMMR model via simulations in supplementary material (Exhibit A, attached herewith). It obtains a high degree of accuracy in identifying the true K in our new model.

Generalization of the Plaid Model

To make comparisons with the generalized FMMR model introduced herein, we generalize the plaid model by introducing covariates into the model such that it can as well cluster overlapping multivariate regression data. To date, none of the conventional plaid model techniques have been conducted on overlapping clustering for (univariate/multivariate) regression data to best of our knowledge. The plaid model and probabilistic model are the two most popular methods for overlapping clustering ordinary data. The reason to select the plaid model rather than the probabilistic model for comparison is because the latter one revolves around Bayesian model like ours. The plaid model however brought in the concept of layers (subsets of rows and columns of a data matrix), wherein a data matrix is decomposed as the sum of the layers. Model (2.1) is the generalized plaid model. It seeks to find the parameter estimators that minimize the Q $$Q = \frac{1}{2}\sum_{i=1}^{n}\left\|y_i - \sum_{k=1}^{K}x_i^T B_k P_{ik}\right\|_2^2 + \sum_{k=1}^{K}\rho_{nk}(B_k),$$

where $p_{nk}(B_k)$ is the penalty function defined herein.

Detailed procedures for optimizing Q are shown in Algorithm 1 in FIG. 17. At each time, the algorithm searches a layer which explains as much of the rest data as possible; once a layer has been found, it is subtracted from the data and remains unchanged; the algorithm stops when no further layers can be found. However this method introduces bias to parameter estimators due to the discrete updating scheme, where previous recruited layers cannot be refined as new layers are recruited into the model. To address this issue, we further revised Algorithm 1 to enable joint optimization of all layers. Detailed procedures are presented in Algorithm 2 in FIG. 18.

Asymptotic Properties and Some Simulation Studies
Asymptotic Properties

Khalili and Lin (2013) studied the penalized likelihood approach for variable selection and estimation in finite mixture of regression models with a diverging $p_n$. It was shown that this approach leads to consistent estimation as well as variable selection under certain regularity conditions. Let $f(w; \Theta)$ be the joint density function of $w=(x; y)$ with parameter space $\Theta \in \Omega$. The conditional density function of y given x follows (3.9). Since the regularity conditions given for asymptotic establishments in Khalili and Lin (2013) are made on $p_{nk}(B_k)$ and $f(w; \Theta)$ directly, corresponding theoretical properties can be extended to current problem.

Denote by $B_k^j$ the jth column of $B_k$ for $j=1, \ldots, q$. Let $B_k^j=(B_{k1}^j, B_{k2}^j)$ to divide the coefficient vector into non-zero and zero subsets. Denote by $\Theta^0$ the true value of $\Theta$, $\Theta^0 = (\Theta_1^0, \Theta_2^0)$ is the corresponding decomposition such that $\Theta_2^0$ contains all zero coefficients, i.e. $B_{k2}^j$, and $\hat{\Theta}_n = (\hat{\Theta}_{n1}, \hat{\Theta}_{n2})$ is the estimate. Since the dimension of $\hat{\Theta}_{n1}$ increases with n as $p_n$ is diverging, we investigate the asymptotic distribution of a finite linear transformation, $D_n \hat{\Theta}_{n1}$, where $D_n$ is a constant $l \times d_{n1}$ matrix with a finite l, and $d_{n1}$ is the dimension of $\Theta_1^0$. Moreover $D_n D_N^T \to D$ and D is a positive definite symmetric matrix. In the theory, we assume that the order K is independent of the sample size n and also is known beforehand. Strategies for its selection in applications are discussed herein and performance of the selection is studied in simulations.

Theorem 1. Suppose the penalty function $p_{nk}(B_k)$ satisfies conditions $P_0$-$P_2$, and the joint density function $f(w; \Theta)$ of a random sample $w=(x; y)$ satisfies conditions $R_1$-$R_5$.

I. If $$\frac{p_n^4}{n} \to 0,$$

then there exists a local maximizer $\hat{\Theta}_n$ for the penalized log-likelihood $\tilde{l}_n(\Theta)$ with $$\|\hat{\Theta}_n - \Theta^0\| = O_p\left\{\sqrt{\frac{p_n}{n}}(1+q_{2n})\right\},$$

where $$\frac{p_n^5}{n} \to 0,$$

II. If $\rho_{nk}(B_k)$ also satisfies condition $\mathcal{P}_3$ and $$q_{2n} = \max_{k,st}\left\{\frac{|\rho'_{n,k}(b_{k,st}^0)|}{\sqrt{n}}; b_{k,st}^0 \neq 0\right\}.$$

for any $\sqrt{n/p_n}$-consistent maximum penalized log-likelihood estimator $\hat{\Theta}_n$, as $n \to \infty$ it has:

1. Variable selection consistency:

$$P(\hat{B}_{k2}^j = 0) \to 1, k=1, \ldots, K \text{ and } j=1, \ldots, q.$$

2. Asympiotic normality:

$$\sqrt{n} D_n \mathcal{I}_1^{-1/2}(\Theta_1^0)\left\{\left[\mathcal{I}_1(\Theta_1^0) - \frac{\rho_n''(\Theta_1^0)}{n}\right](\hat{\Theta}_{n1} - \Theta_1^0) + \frac{\rho_n'(\Theta_1^0)}{n}\right\} \to^d \quad (5.1)$$

$$N(0, D),$$

where $\mathcal{I}_1(\Theta_1^0)$ is the Fisher information matrix under the true subset model.

Proof. Write $\Theta = (\theta_1, \theta_2, \ldots, \theta_{t_n})^T$, where $t_n$ is the total number of parameters in the model. Regularity conditions $P_0$-$P_3$ and $R_1$-$R_5$ has the same form as in Khalili and Lin (2013). By following the proofs in Khalili and Lin (2013), conclusions below can be established.

1) Let $$\sigma_n = \sqrt{\frac{p_n}{n}}(1+q_{2n}).$$

For any given $\varepsilon > 0$, there exists a constant $C_\varepsilon$ such that $$\lim_{n \to \infty} P\left\{\sup_{\|u\|=C_\varepsilon} \tilde{l}_n(\Theta^0 + \sigma_n u) < \tilde{l}_n(\Theta^0)\right\} \geq 1 - \varepsilon.$$

2) For any $\Theta = (\Theta_1, \Theta_2)$ in the neighborhood $\|\Theta - \Theta^0\| = O(\sqrt{p_n/n})$, it has that $$P\{\tilde{l}_n(\Theta_1, \Theta_2) < \tilde{l}_n(\Theta_1, 0)\} \to 1 \text{ as } n \to \infty.$$

3)

$$\left\{-\frac{1}{n}E\{l_n''(\Theta_1^0)\} + \frac{\rho_n''(\Theta_1^0)}{n}\right\}(\hat{\Theta}_{n1} - \Theta_1^0) + \frac{\rho_n'(\Theta_1^0)}{n} = \frac{l_n'(\Theta_1^0)}{n} + o(1/\sqrt{n}). \quad (5.2)$$

By (5.2), the left side of (5.1), denoted as A, becomes $$A = \sum_{i=1}^{n} W_i + o(1),$$

where $$W_i = n^{-\frac{1}{2}} D_n \mathcal{I}_n^{-\frac{1}{2}}(\Theta_1^0)[\partial \log f(w_i; \Theta_1^0)/\partial \Theta_1],$$

$i=1, \ldots, n$, are independent and identically distributed random vectors. They satisfy the condition of the Lindeberg-Feller central limit theorem and also $$\sum_{i=1}^{n} \text{Cov}(W_i) = D_n D_n^T \to D \text{ as } n \to \infty.$$

Theorem 1 can be easily derived from above conclusions. We refer readers to Khalili and Lin (2013) for detailed proofs.

By Theorem 1.I, $\hat{\Theta}_n$ with respect to LASSO or Elastic Net penalty has convergence rate $\sqrt{p_n/n}$ under appropriate choice of tuning parameters. Note that consistent estimator of $\Theta^0$ does not necessarily guarantee the variable selection consistency. Theorem 1.II looks into conditions under which the estimator is consistent in variable selection. However the LASSO or Elastic Net penalty cannot attain both properties simultaneously because the bias term $q_{2n}$ is proportional to $\lambda k/\sqrt{n}$, while $\lambda k$ must be large enough to achieve sparsity. This problem can be efficiently solved by using the adaptive LASSO or adaptive Elastic Net penalty instead, which fulfills the conditions required for both variable selection and estimation consistency.

Design of the Simulations

Two scenarios are designed for the unoverlapping and overlapping situations respectively. In each scenario, data are generated from model (2.1) with K=3, $p_n$=15, q=3 and n=150; 450 respectively. Predictors $x_i$ are IID from $N_{p_n}(0; \Sigma_1)$ and random errors $\varepsilon_1$ are IID from $N_q(0, \Sigma)$ with $\Sigma_1$ (i, j)=$0.5^{|i-j|}$ and $\Sigma(i, j)=0.75^{|i-j|}$.

The sparse coefficient matrixes $B_k$, k=1, 2, 3 are generated as follows, $$B_k = W \otimes S \otimes T, \quad (5.3)$$

where $\otimes$ indicates the element-wise product. Each entry of W is drawn independently from N(0, 1), each entry of S independently from the Bernoulli distribution B(1, $p_1$), and rows of T (either all 1 or all 0) are determined by $p_n$ independent Bernoulli draws from B(1, $p_2$). Thus for each response variable, we expect $p_1 p_2 p_n$ relevant predictors, and there will be $(1-p_2)pn$ predictors in expectation to be irrelevant to all q responses. We have for all scenarios $p_1$=0:5 and $p_2$=0:9. Simulations are repeated for 50 times. For each repetition, a new sequence of $B_k$, k=1; 2; 3 are generated. To show that our proposed method has the ability to identify overlapping clusters, we assume K is known in following simulations.

Scenario 1: The 3 clusters are unoverlapping, each cluster contains n/3 observations.

Scenario 2: 70% of the observations involve in single clusters, 22% of the observations involve in two clusters and 8% of the observations involve in three clusters.

Cluster Recovery Quality Measures

Quality measures in Baeza-Yates, Ribeiro-Neto et al. (1999) are used to evaluate the clustering performance of the proposed method. Suppose we want to compare a target cluster A and a retrieved cluster Â. Ns denotes the number of observations in set S. The quality measures are defined as $$\text{"specificty"} = \frac{N_{A \cap \hat{A}}}{N_A},$$

$$\text{"sensitivity"} = \frac{N_{A \cap \hat{A}}}{N_{\hat{A}}},$$

$$\text{"}F_1 \text{ measure"} = \frac{2N_{A \cap \hat{A}}}{N_A + N_{\hat{A}}}.$$

The $F_1$ measure, taken as the harmonic mean of specificity and sensitivity, gives an overall measure of the clustering performance.

In order to compare a sequence of target clusters, we use a one-to-one correspondence match approach (Turner, Bailey and Krzanowski 2005). We first make the number of retrieved clusters to be the same as the number of target clusters by adding null clusters to retrieved clusters or dropping additional poorly retrieved clusters. Retrieved clusters are then matched to target clusters via a one-to-one correspondence. Finally calculate the mean pair-wise quality measures. The optimal one-to-one match is the one producing the highest mean pair-wise $F_1$ measure.

Cluster Model Comparisons

A sequence of methods have been implemented in simulations including the plaid model (plaid) and its revised counterparts (aplaid); the FMR model with 'flexmix' R package (EM) in Leisch (2004) and Grun and Leisch (2008) where the multivarite responses are treated as independent and overlapping problems are not considered; our proposed generalized FMMR model with the multivariate responses treated as independent (gEMseplasso0); our proposed generalized FMMR model with separate lasso estimation for $B_k$ in (3.12) (gEMseplasso); and finally our proposed original method (gEMmrce).

The clustering performances were evaluated via quality measures as well as the sum of squared estimation errors (SSE) for model coefficients. Results for the example simulations are summarized in FIGS. 2A-2D and FIGS. 3A-3D. In scenario 1 when there is no overlappings, EM and gEMseplasso0 do equally well showing that the generalized FMMR model retains the ability in recovering unoverlapping clusters. By taking into account the covariance structure among multivariate responses in generalized FMMR model, gEMseplasso and gEMmrce produce a higher degree of clustering accuracy than EM and gEMseplasso0. There is little difference between gEMseplasso and gEMmrce however. When there are 30% overlappings in scenario 2, specificity of the EM drops down dramatically resulting in a poor $F_1$ measure. The gEMseplasso0 does much better than the EM by estimating overlapping clusters, but on the other hand it is worse than the gEMseplasso and gEMmrce. There is again little difference between gEMseplasso and gEMmrce. Moreover, the gEMseplasso and gEMmrce converge fast with n, achieving a median 95% accuracy in terms of $F_1$ measure when n=450. The plaid and aplaid however have a poor performance in all scenarios.

Therapeutic Biomarker Screening for the Sanger Dataset

We applied the innovative techniques herein to analyzing the SANGER high throughput drug sensitivity dataset for cancer. An updated version of this data set (cancerrxgene.org/downloads/) contains 140 drugs as response variables, 13831 genomic features as covariates (including tissue type, rearrangements, mutation status of 71 cancer genes, continuous copy number data of 426 genes causally implicated in cancer, as well as genome-wide transcriptional pro les), and 707 human tumor cell lines as samples. The responses, made up with IC50 values from pairwise drug-cell-line screening, has some missing values. Therefore the data was first filtered by removing cell lines for which less than 50% of the drugs were tested, resulting in 591 cell lines remaining. In the remaining data, about 37.4% of the cell lines are with missing values. These missing values are imputed via the random forest imputation algorithm (Ishwaran, Kogalur, Blackstone and Lauer 2008; Stekhoven and Buhlmann 2012).

In order to identify patterns of cancer-specific therapeutic biomarkers, we employed method gEMseplasso in the analysis. Note that by "cancer-specific" we do not assume separate patterns for each cancer type but rather clusters that may be driven by one or a small number of cancer types. Throughout the analysis, we fixed K to a value of 3, although as previously shown, a BIC model selection approach could also be used. However, fixing the value of K does not limit the interesting findings that we can still find and saves on computational time.

Due to the scale and complexity of the data, the analysis, in this example, was conducted in three steps. Although simulation studies show that modeling with multivariate responses yields much higher clustering accuracy than modeling with single response, it is unreasonable to simply fit all 140 drugs (responses) in one generalized FMMR model. Because by doing so, one assumes that the cell line assignments to components are the same for all 140 drugs, which can hardly be true. Thus in our analysis, we first divide the 140 drugs into groups and then fit each drug group with a generalized FMMR model, strategies of which lead to following three steps in detail.

In the first step, for example as implemented in a drug analysis computing system, the processing takes received drug data and fits each drug c by a generalized FMMR model. As a result, we obtain drug-specific cell line assignments, $\hat{Z}_c$, as well as component-wise coefficient estimates, $\hat{B}_k^c$ for $k=1, \ldots, 3$.

Figure 4A:
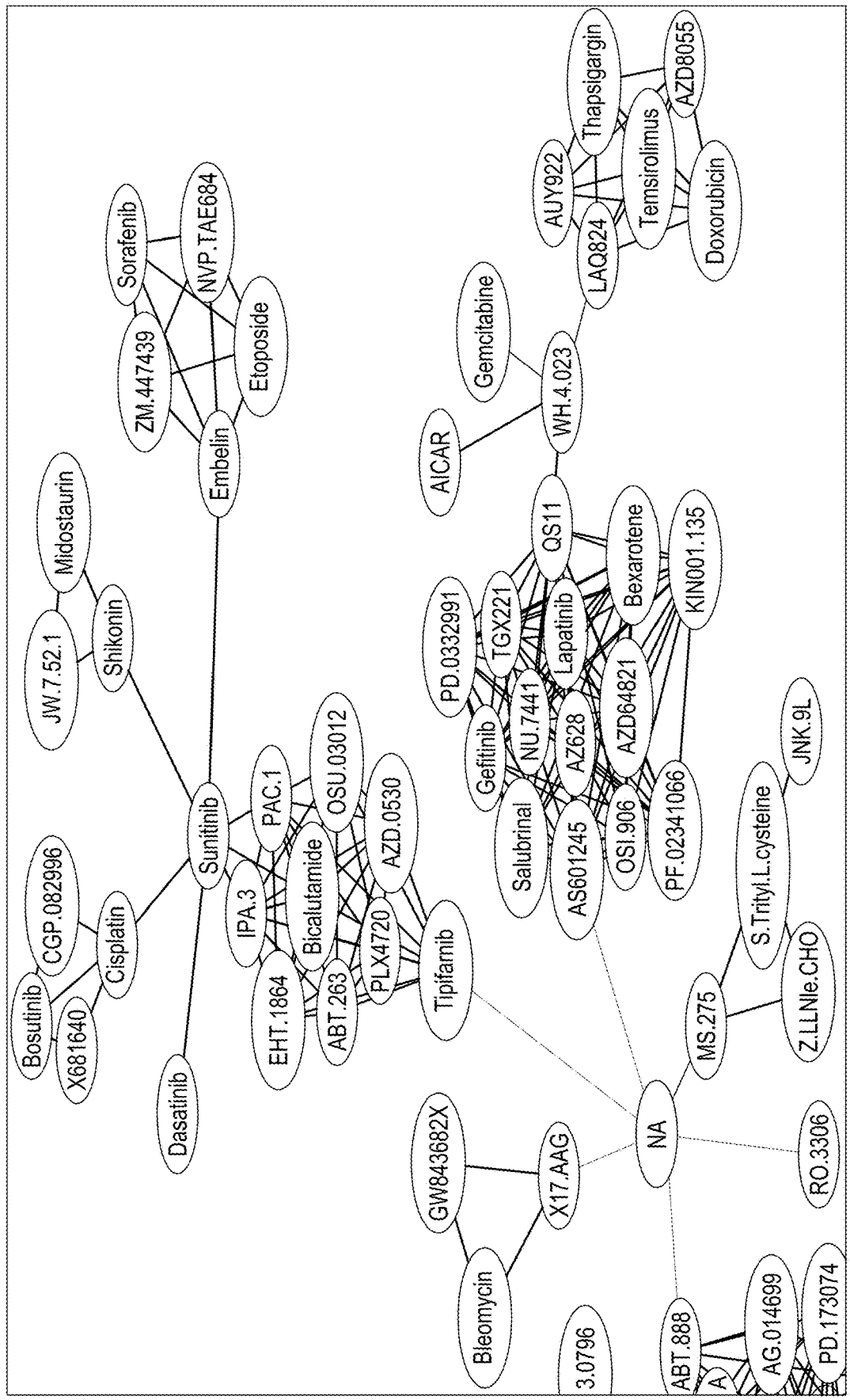
FIGS. 4A-4C illustrate drug groupings that result from application of an affinity-propagation clustering (APC) algorithm, showing different nodes, each node corresponding to a different drug as a second-level cluster.
Figure 4B:
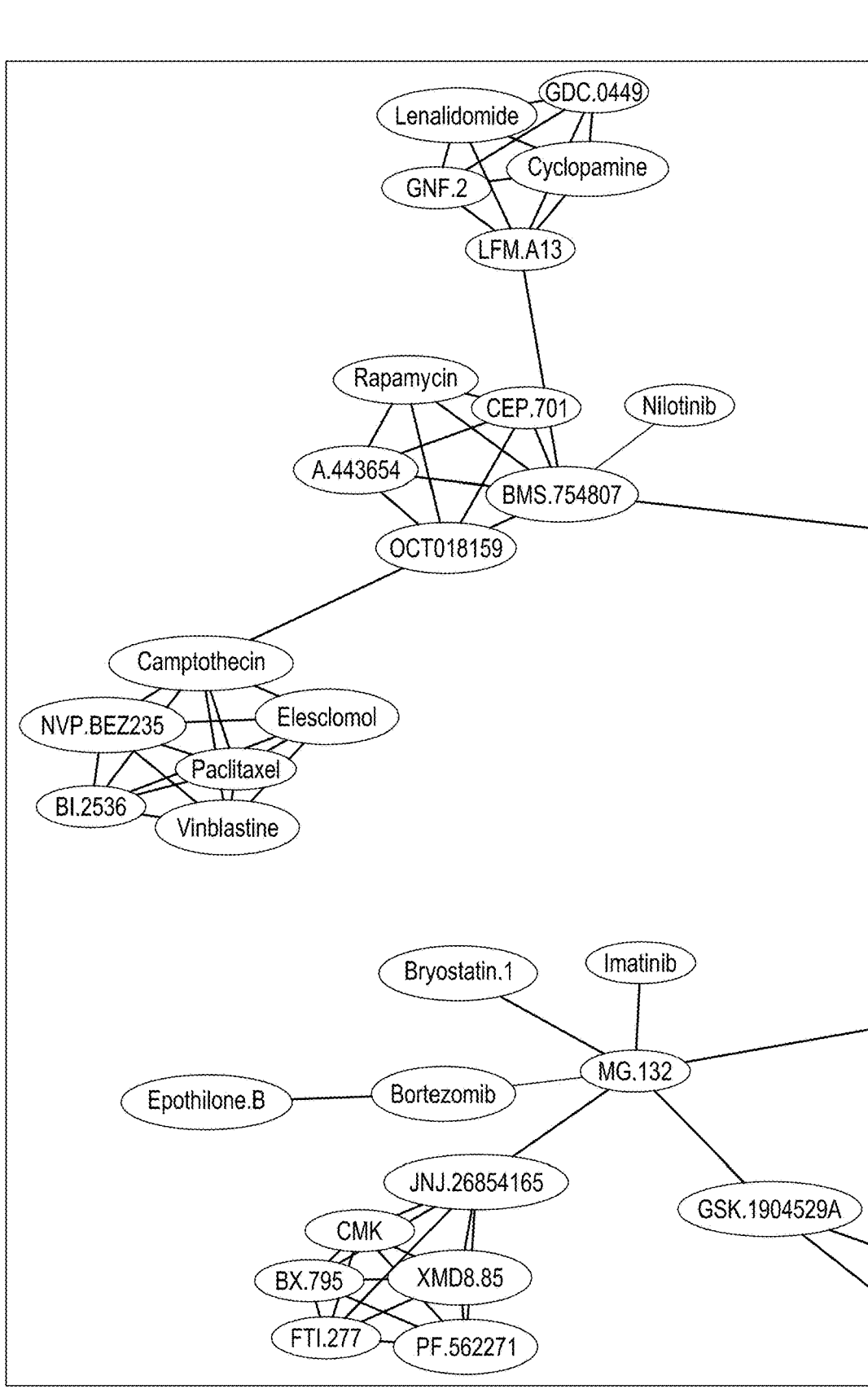
Figure 4B:
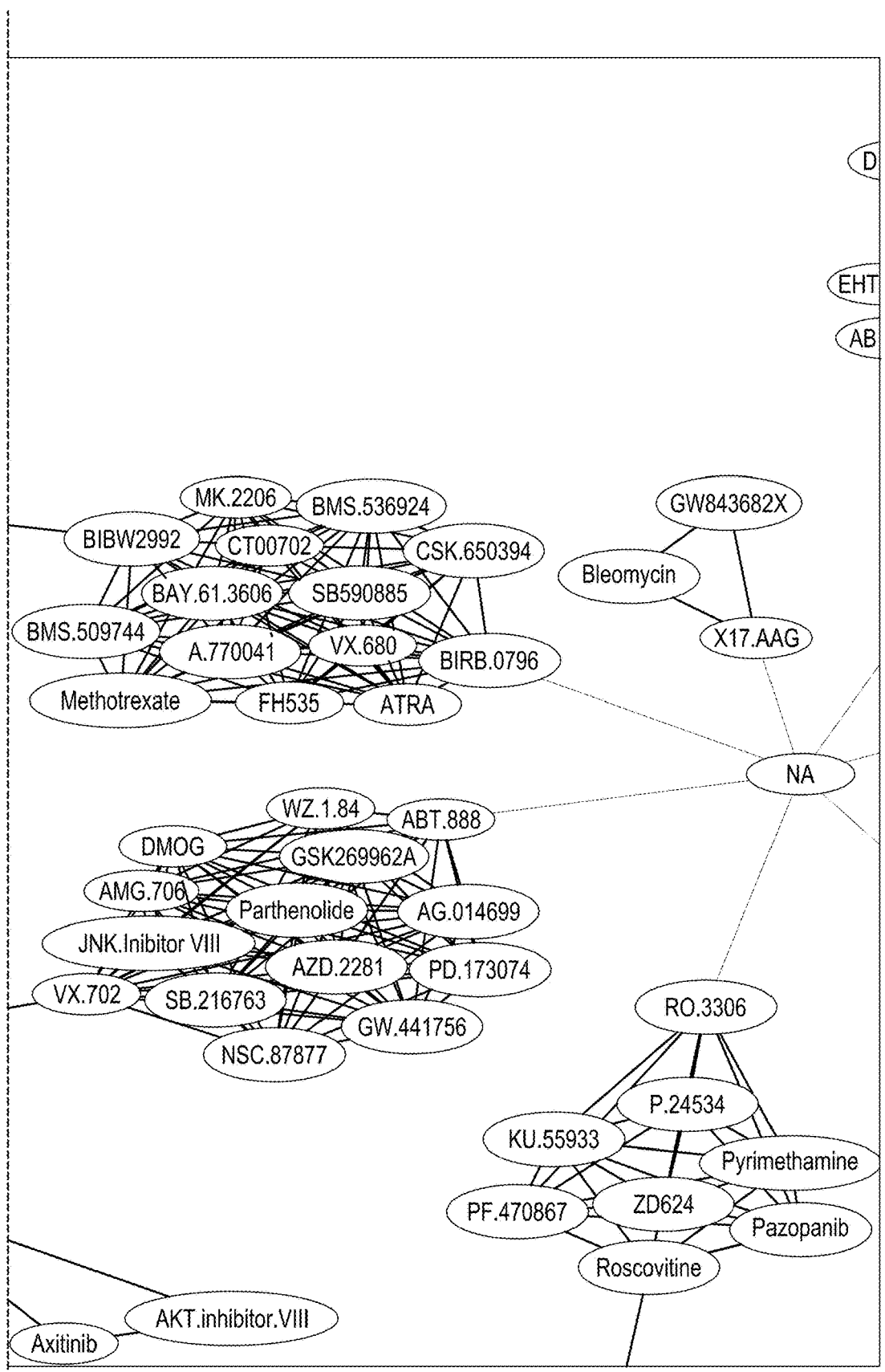
Figure 4C:
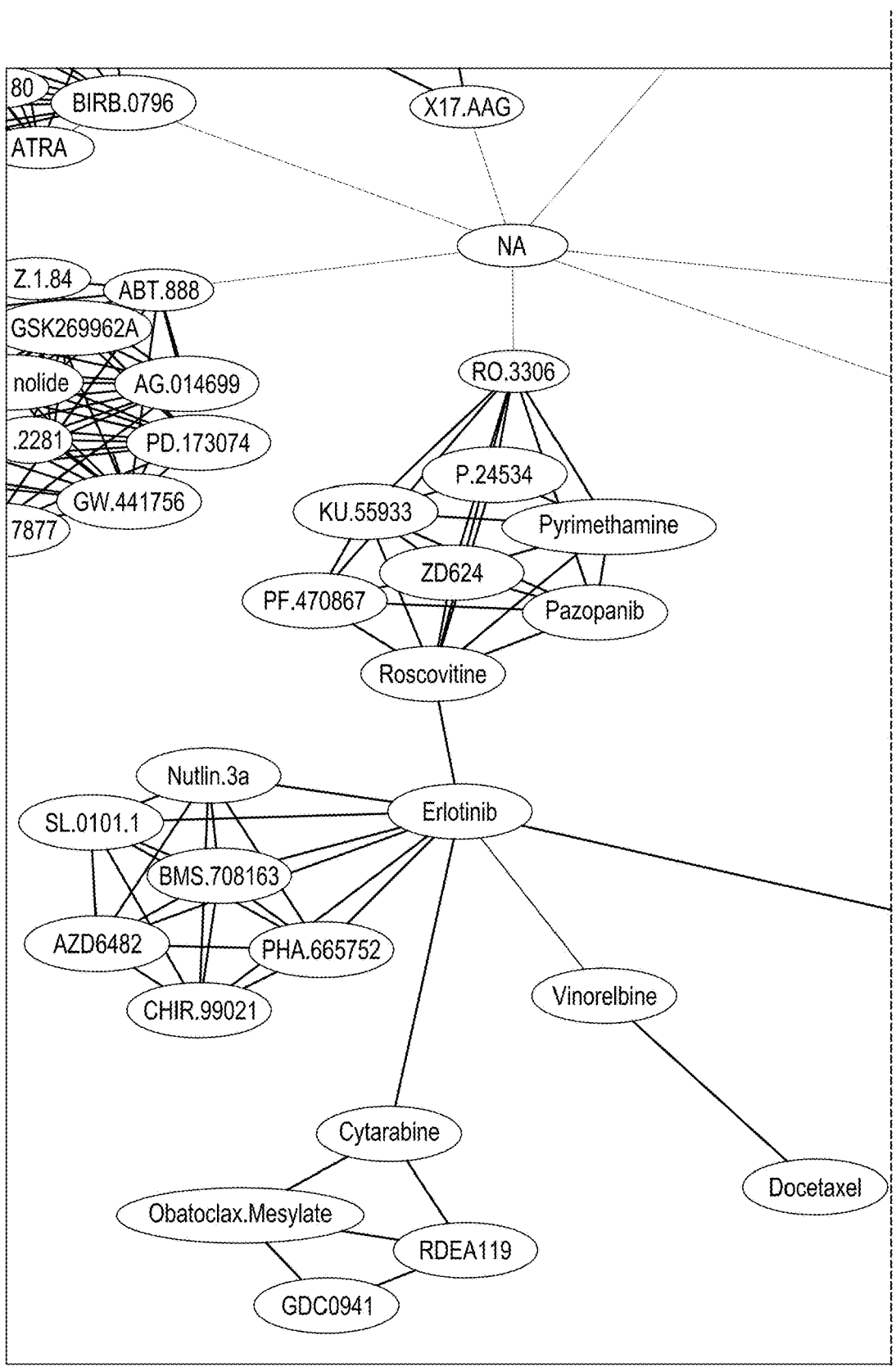
Figure 4C:
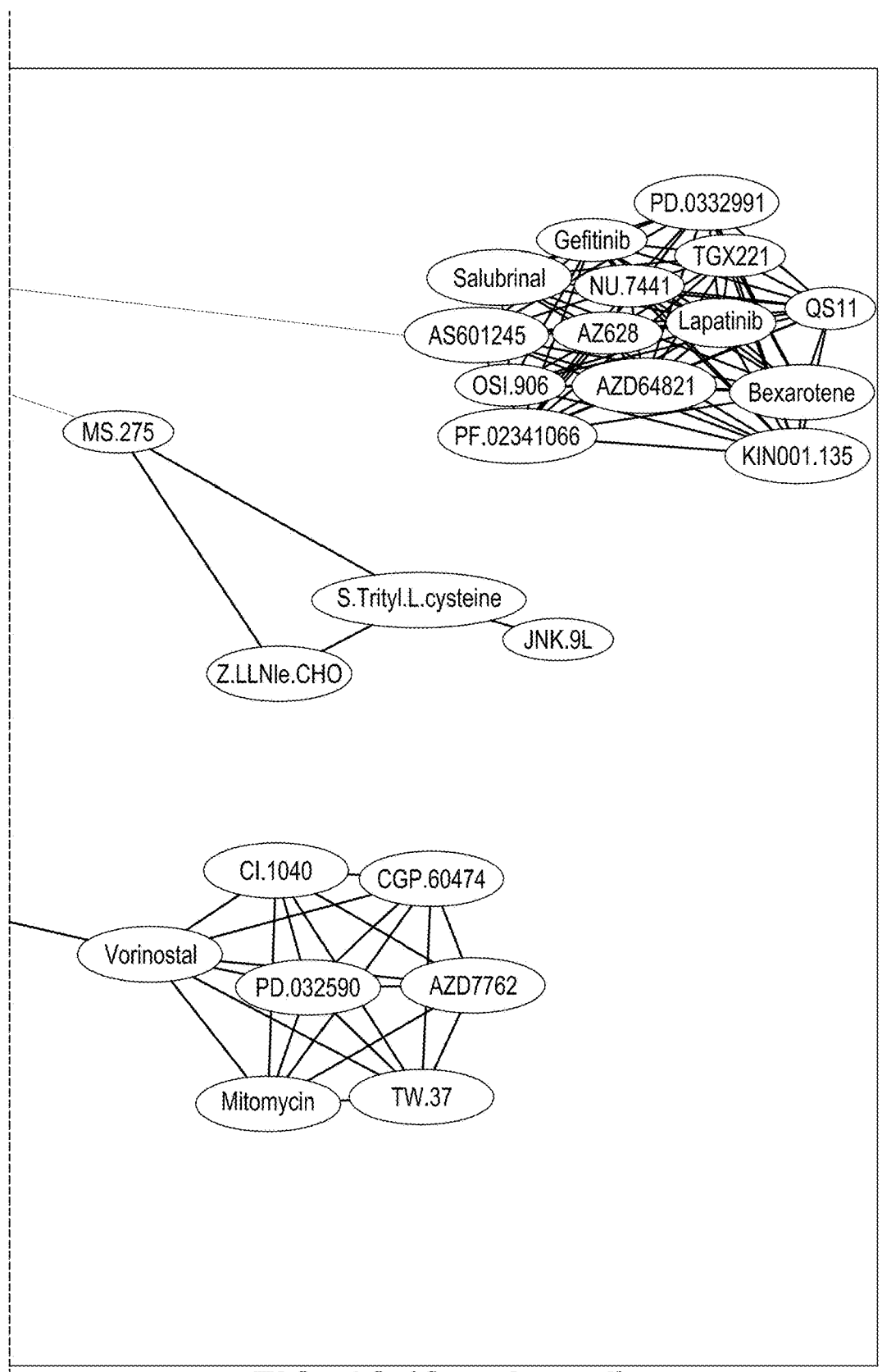

In the second step, the process uses an affinity-propagation clustering (APC) algorithm (Frey and Dueck 2007) to group the 140 drugs based on results from the first step. The grouping is conducted in a two-level nested manner. In the first level, the APC algorithm is applied to all 140 drugs. The pair-wise similarity matrix required by the algorithm as input data is calculated from the Euclidean distance between $\hat{Z}_a$ and $\hat{Z}_b$. In the second level, the APC algorithm is utilized again within every first-level drug group. The pair-wise similarity matrix is calculated from the Euclidean distance between $\hat{B}_k^a$ and $\hat{B}_k^b$ for $k=1, \ldots, 3$. Consequently, drugs having similar cell line assignments and component-wise coefficient estimates are grouped together. Resulting drug groups are shown in FIGS. 4A-4C (which are quadrants of an overall drug grouping (or cluster) display, where the coloring and thickness of connecting lines indicate degree of closeness.

Finally, in the third step of the process, each second-level drug group from step two is fitted by a generalized FMMR model. We get specific cell line assignments, $\hat{Z}_C$, and component-wise coefficient estimates $\hat{B}_k^C$, $k=1, \ldots, 3$, for every second-level drug group C.

Figure 5A:
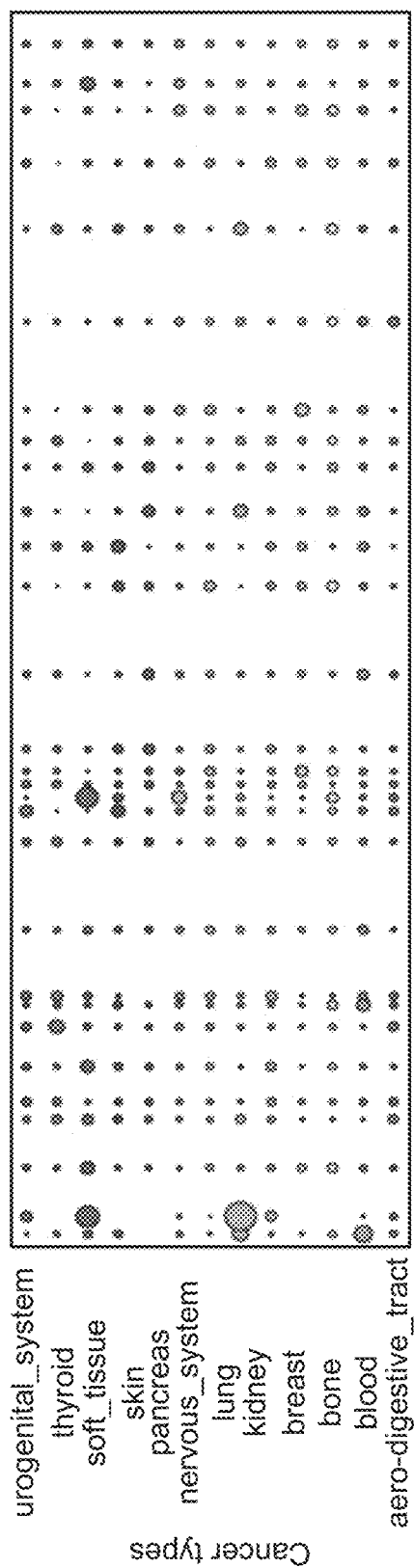
FIG. 5A illustrates a mapping of estimation results of cell lines with a fitting of second-level drug cluster using a generalized FMMR model, in accordance with an example.
Figure 5B:
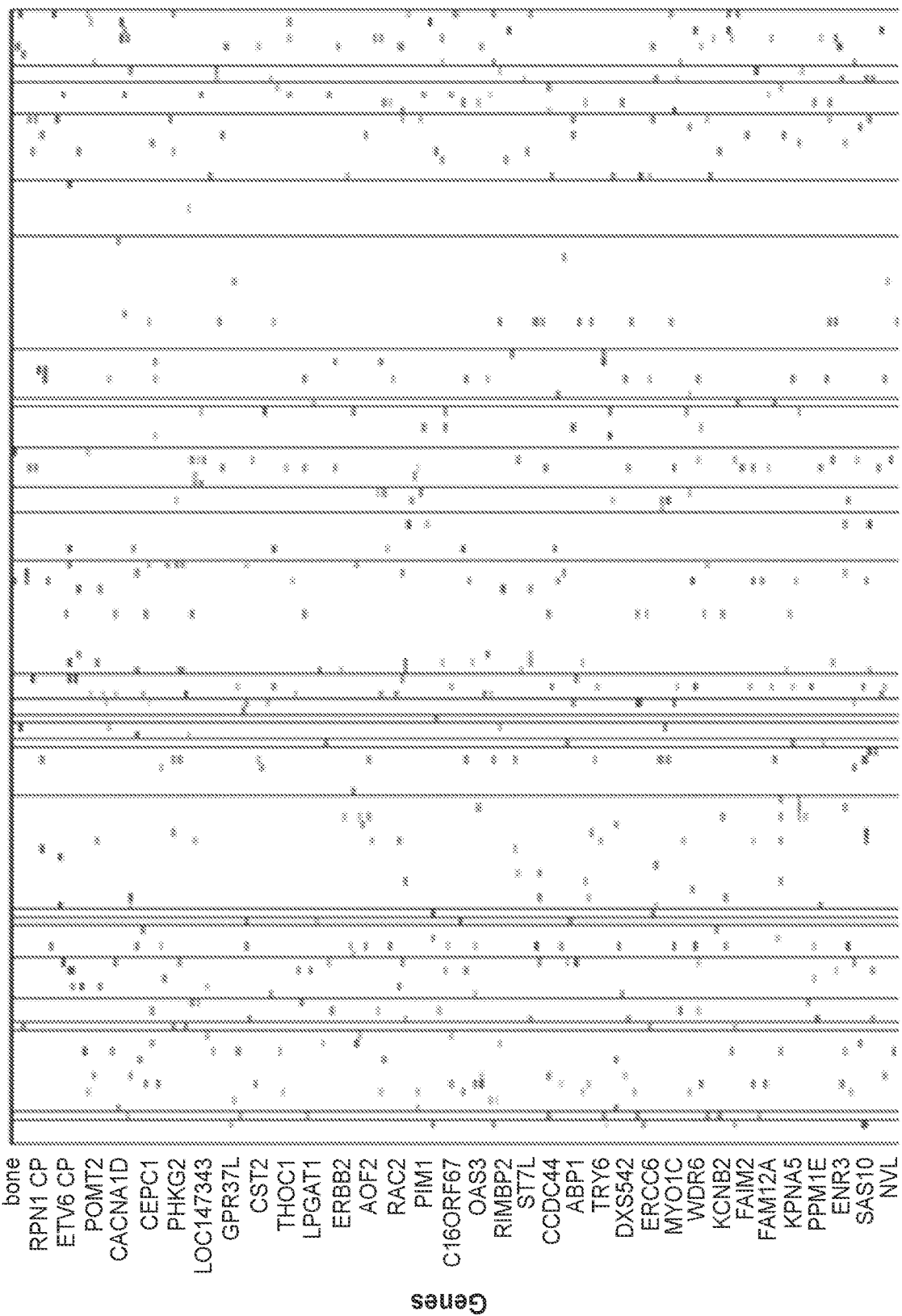
FIG. 5B illustrates a plot of estimate coefficient matrix showing drugs for different genes, in accordance with an example.
Figure 5B:
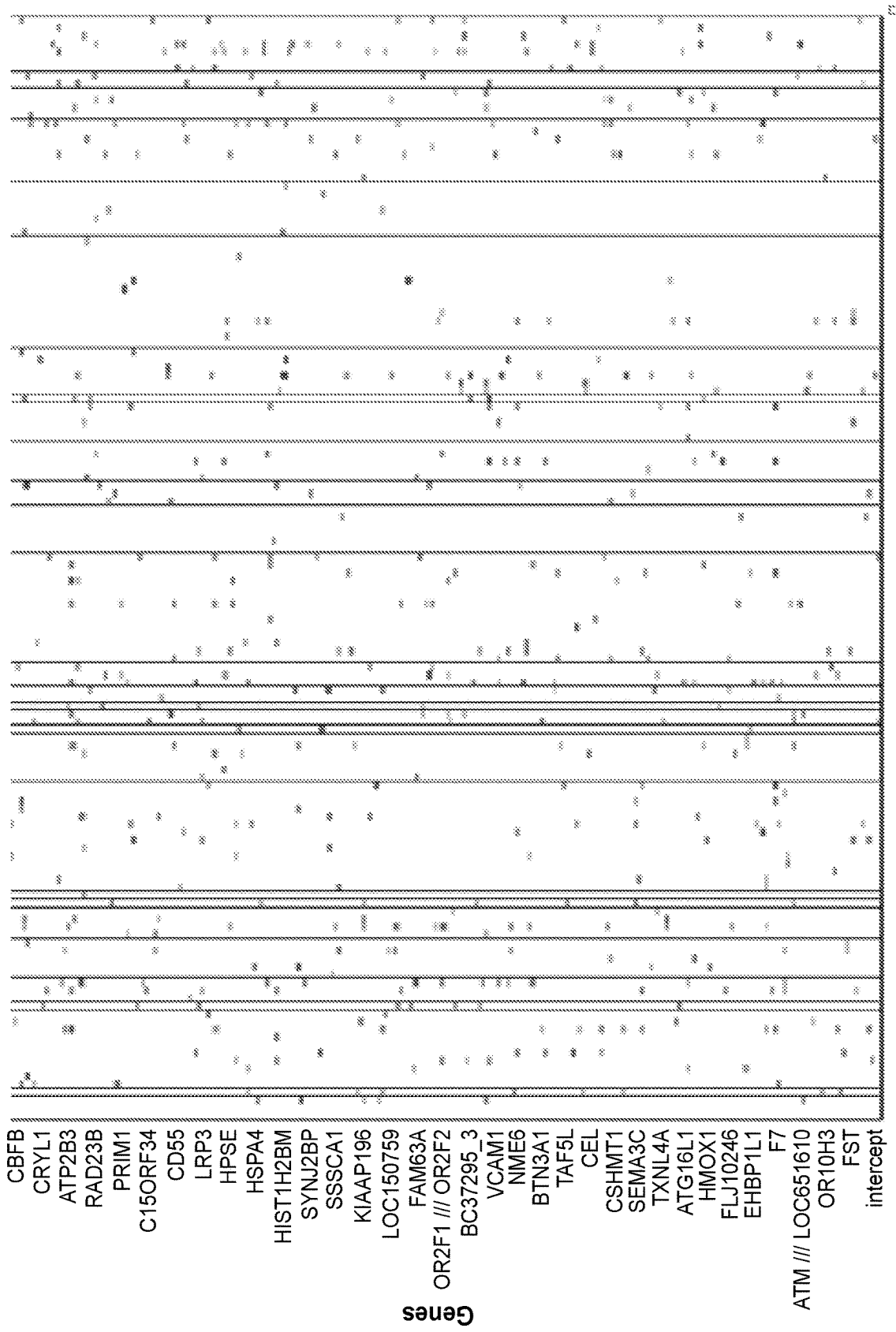
Figure 5B:
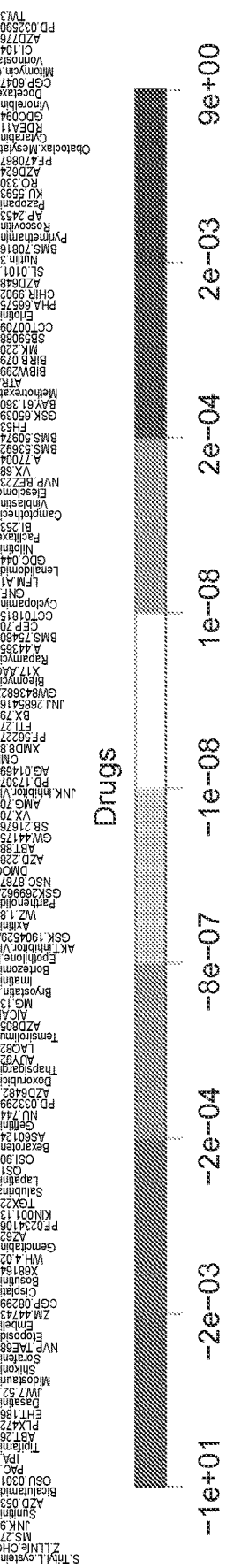
Figure 6A:
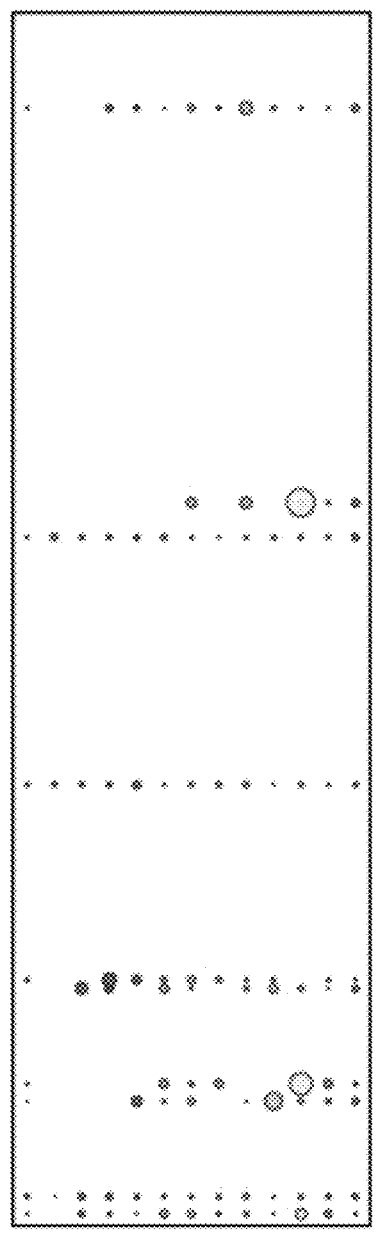
FIG. 6A illustrates a mapping of estimation results of cell lines with a fitting of second-level drug cluster using a generalized FMMR model, in accordance with another example.
Figure 6B:
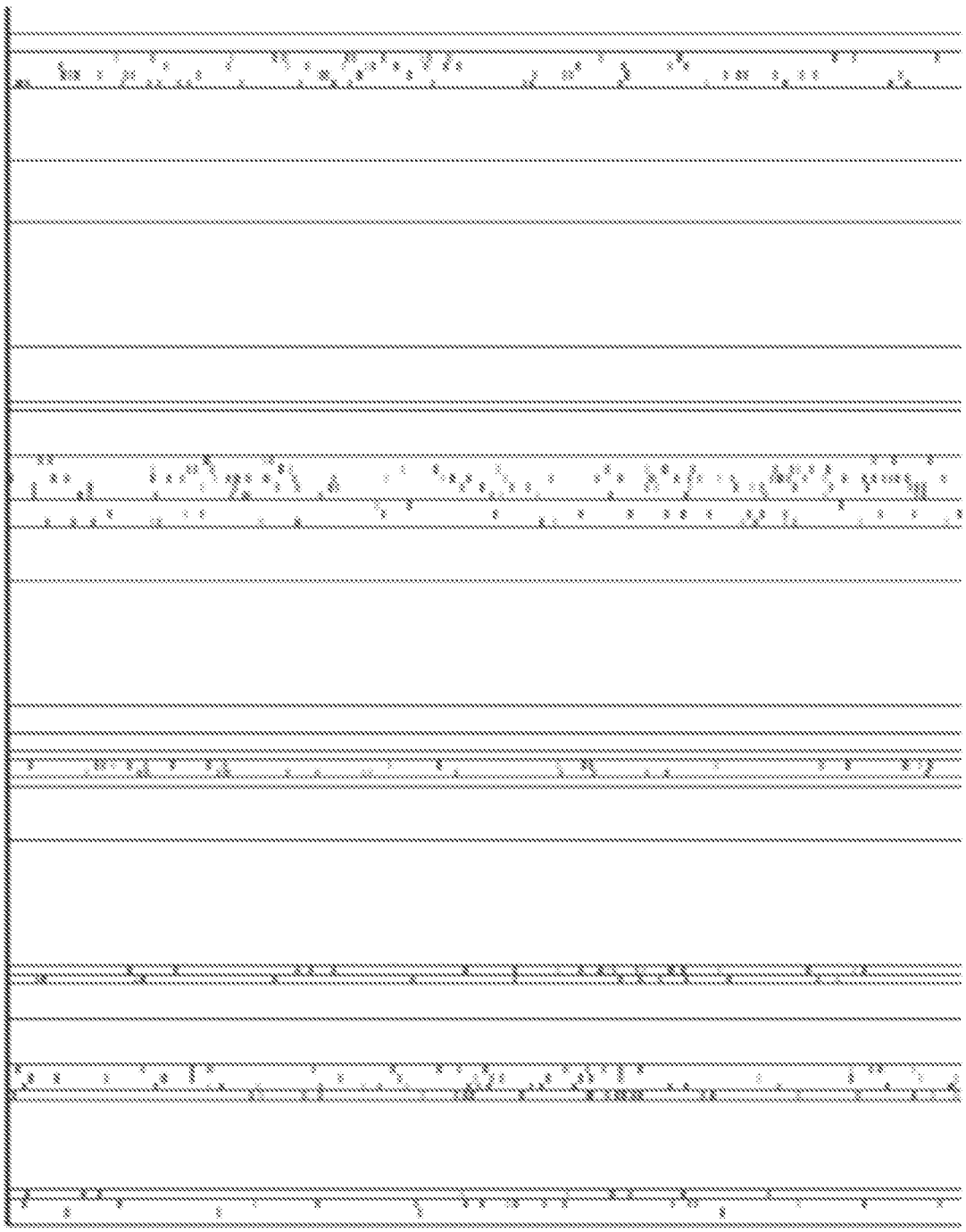
FIG. 6B illustrates a plot of estimate coefficient matrix showing drugs for different genes, in accordance with another example.
Figure 6B:
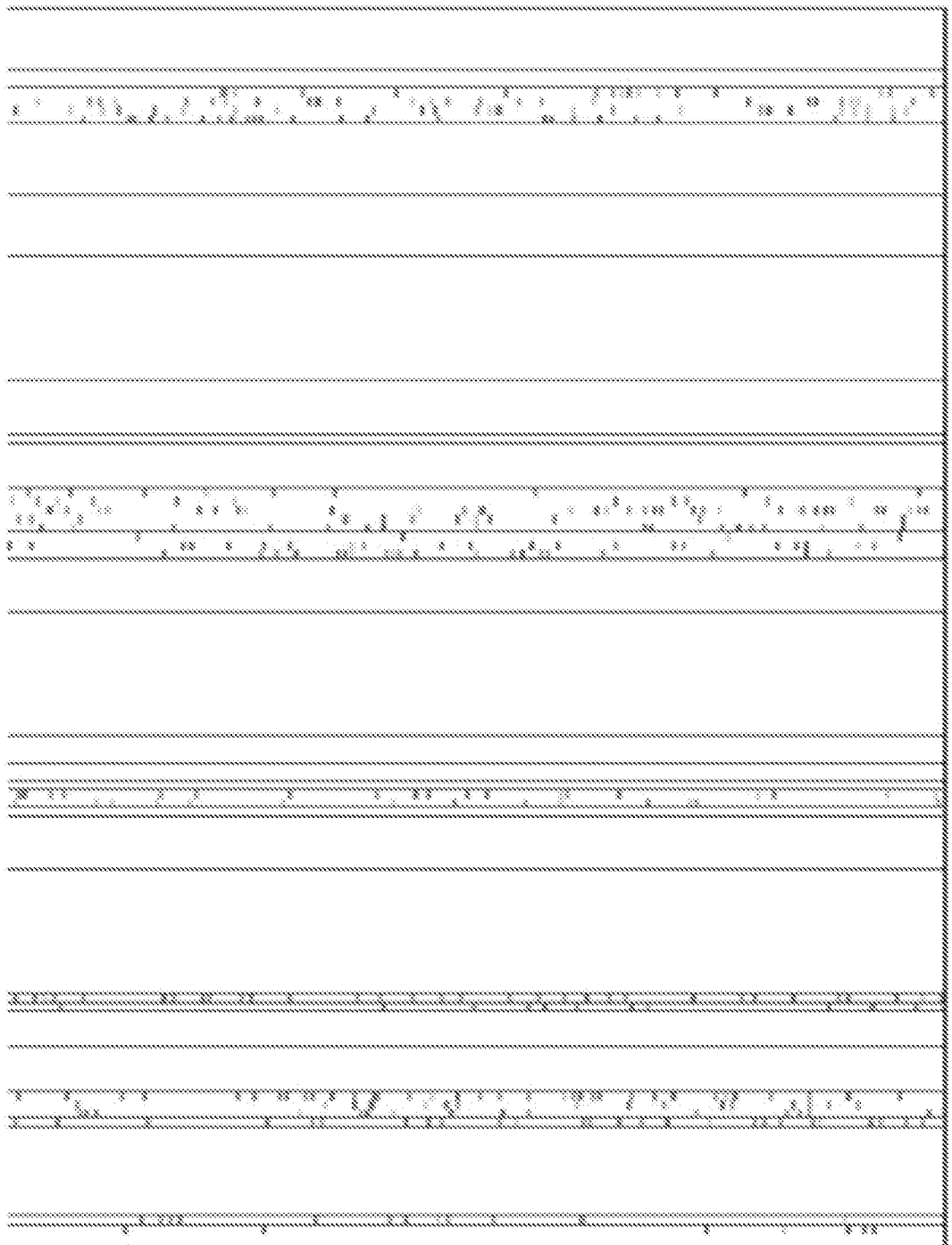
Figure 6B:
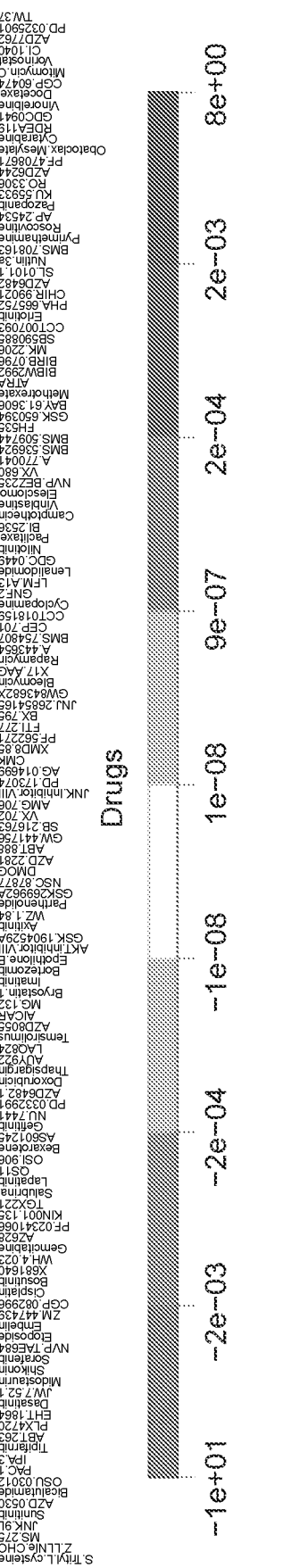
Figure 7A:
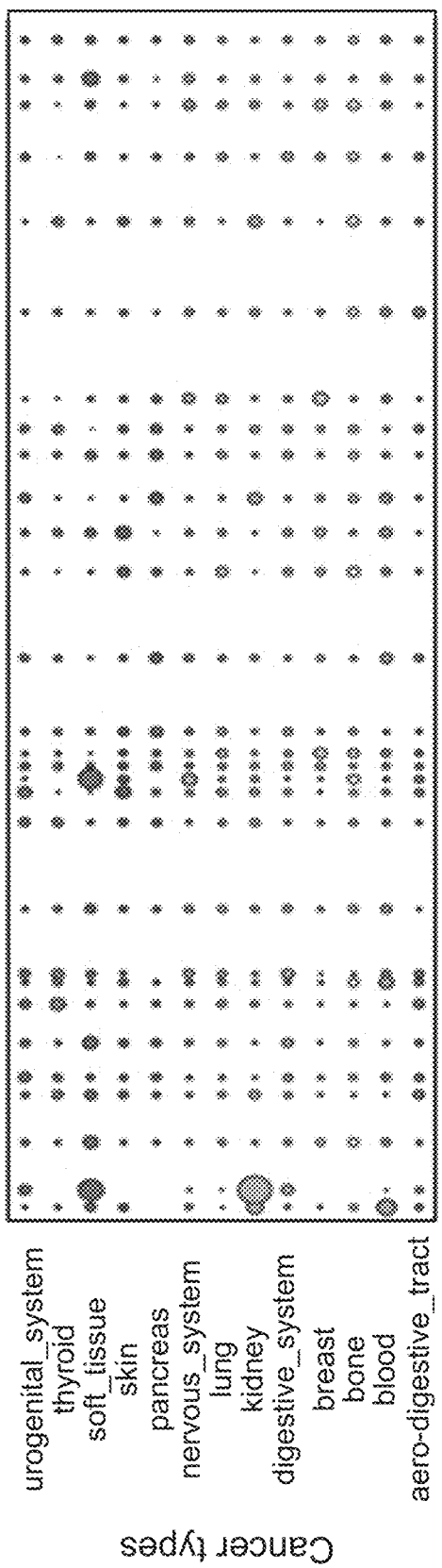
FIG. 7A illustrates a mapping of estimation results of cell lines with a fitting of second-level drug cluster using a generalized FMMR model, in accordance with yet another example.
Figure 7B:
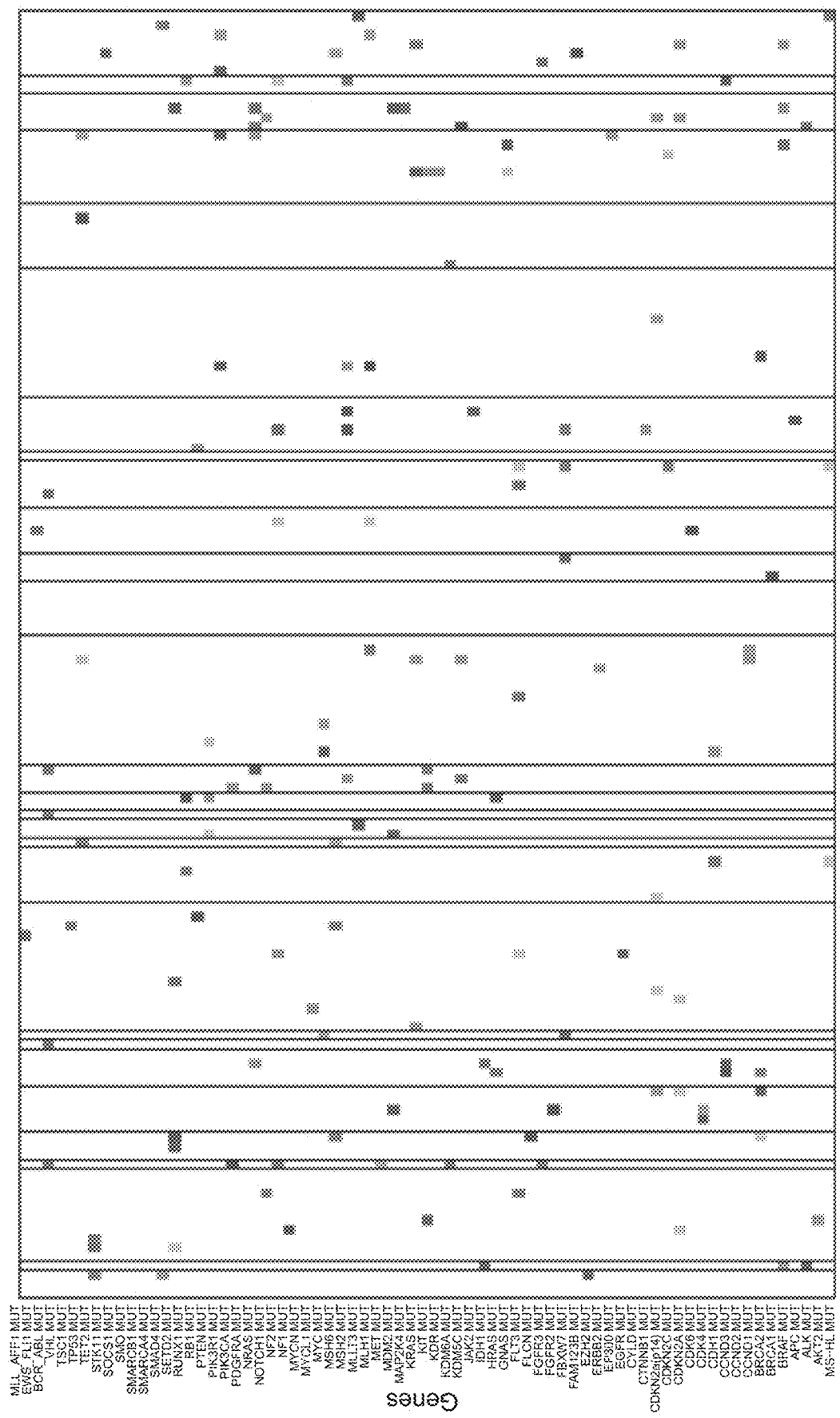
FIG. 7B illustrates a plot of estimate coefficient matrix showing drugs for different genes, in accordance with yet another example.
Figure 7C:
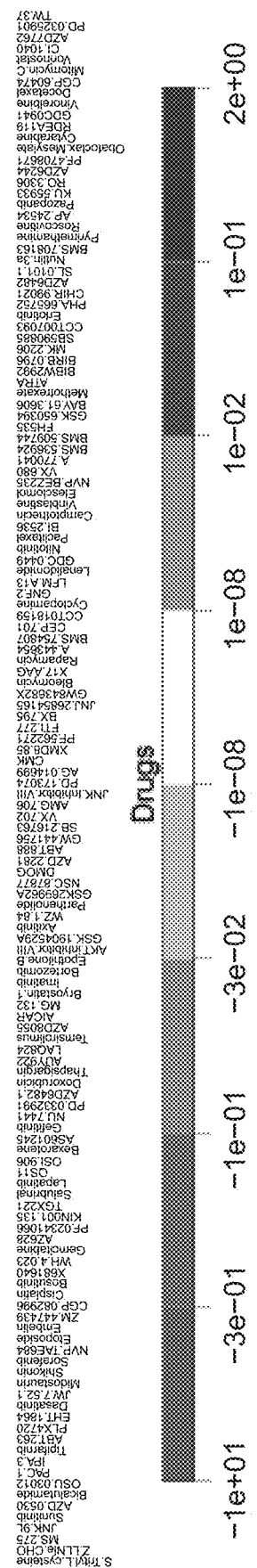
Figure 8A:
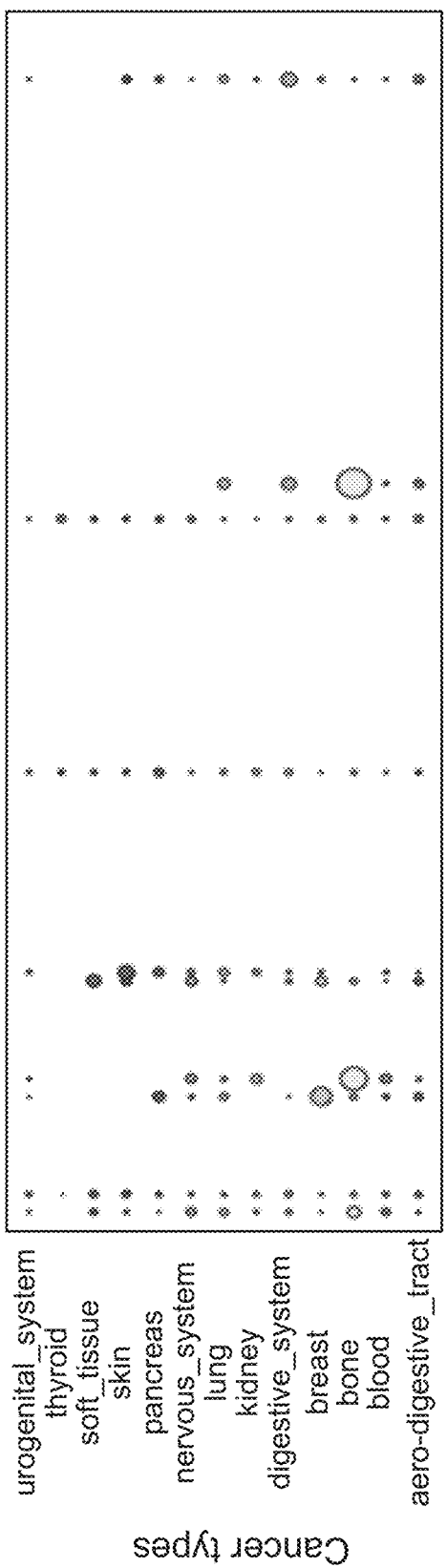
FIG. 8A illustrates a mapping of estimation results of cell lines with a fitting of second-level drug cluster using a generalized FMMR model, in accordance with yet another example.
Figure 8B:
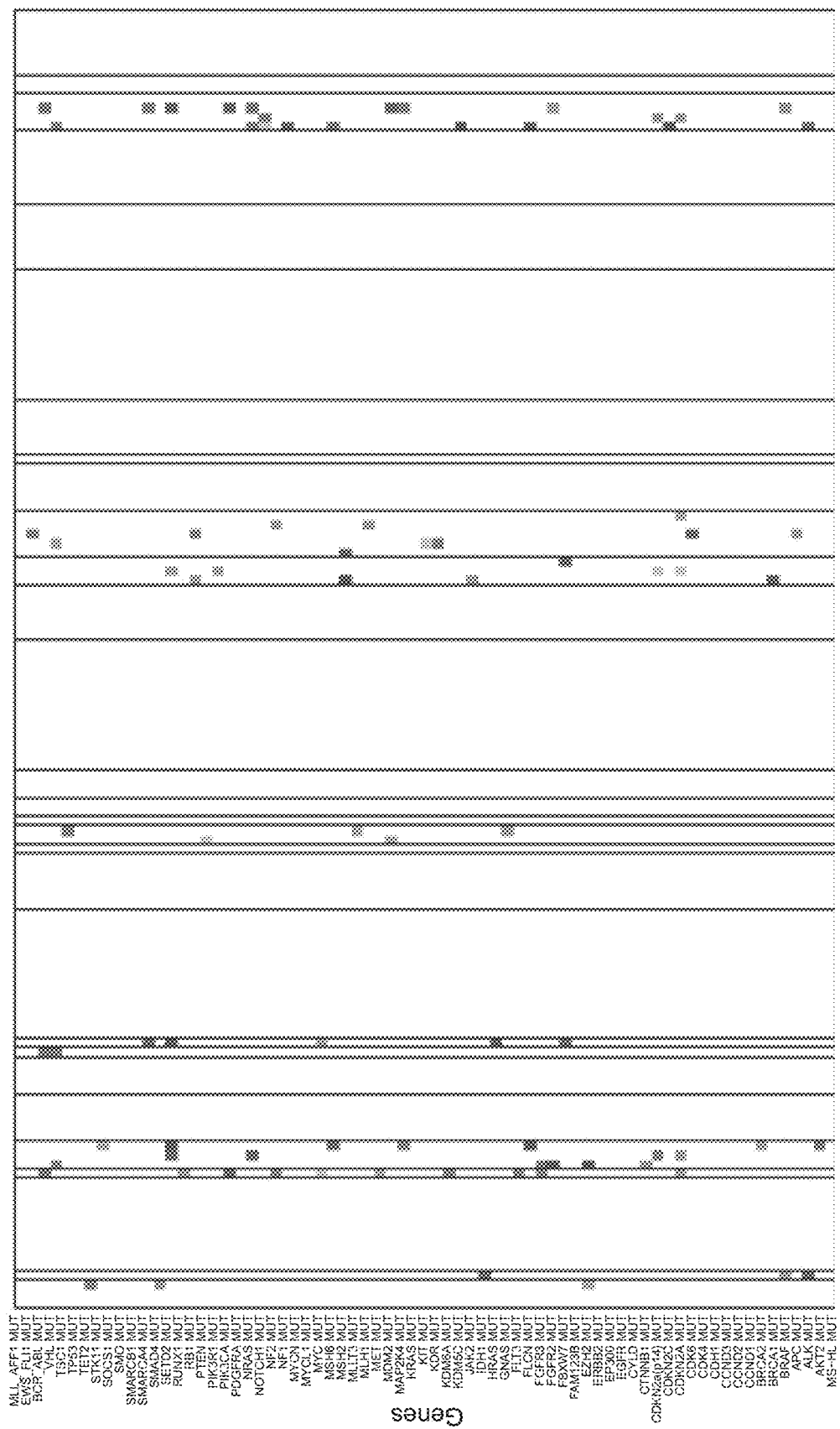
FIG. 8B illustrates a plot of estimate coefficient matrix showing drugs for different genes, in accordance with an example.
Figure 8C:
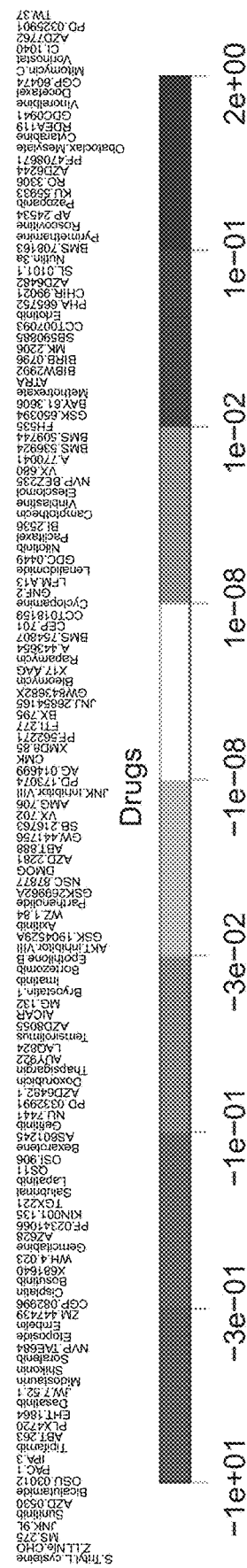

As an illustration, the membership and coefficient estimates of cell line component 1 and 12 for every second-level drug group are shown in FIGS. 5A and 5B (parts 1-3, where part 3 is the legend showing drugs and drug groupings by color corresponding to the corresponding biomarker responsiveness data for each drug on the w-axis of parts 1 and 2) and FIGS. 6A and 6B (with the same sub-parts indications), respectively. The memberships are depicted via frequencies of cancer types that cell lines belong to. These are represented by the size of the colored bubbles in the top panels. Estimates of other clusters are not presented in the paper due to limited space. It's very clear that clusters being driven by different cancer types have very different therapeutic genomic profiles and yet no clusters are homogeneous in a particular cancer type. This speaks to the great heterogeneity seen in cancer overall where in fact, cancer is not thought of as a single disease but rather many diseases characterized by different underlying biological changes.

Next, we show how the present techniques can be used to identify predictive strategies for circumventing drug resistance based on mutation data.

Figure 9A:
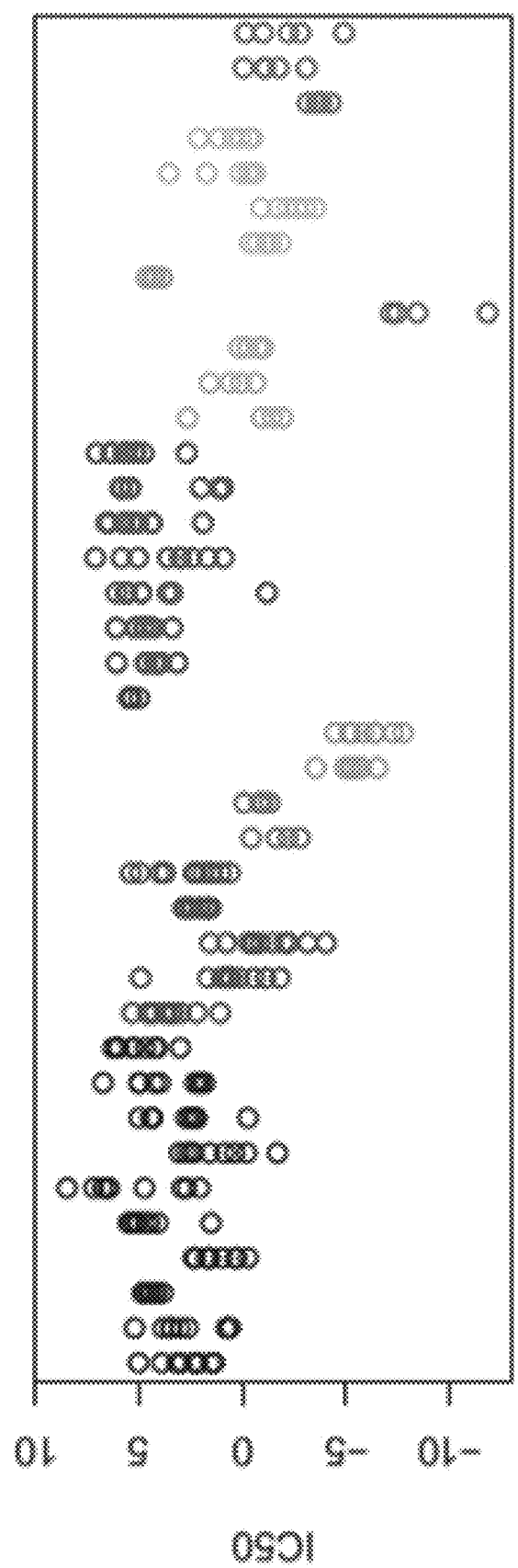
FIG. 9A illustrates drug responsive data for a plurality of drugs for a soft-tissue cancer.
Figure 9B:
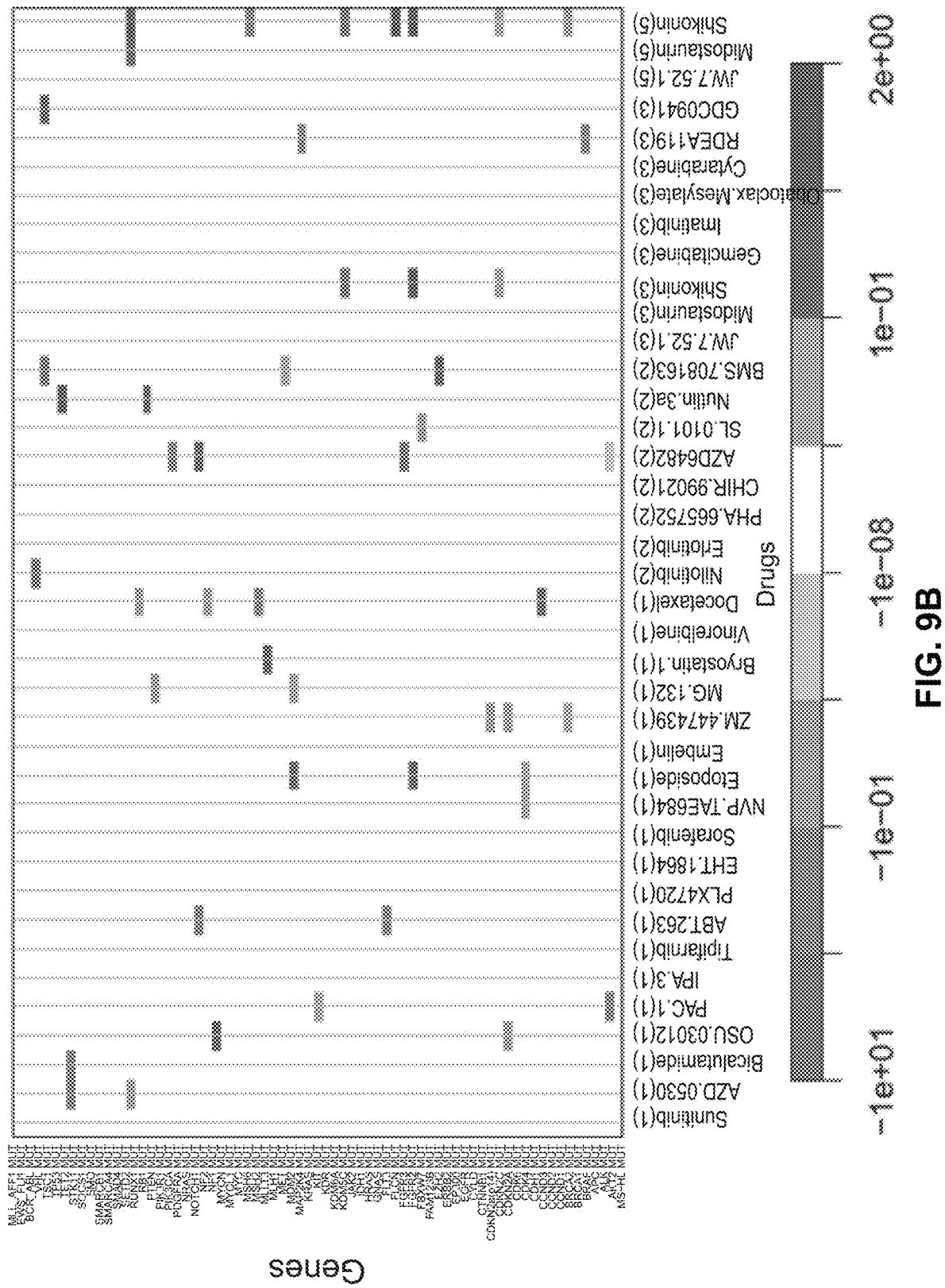
FIG. 9B illustrates a plot of estimate coefficient matrix showing drugs for different genes, in accordance with an example.
Figure 10A:
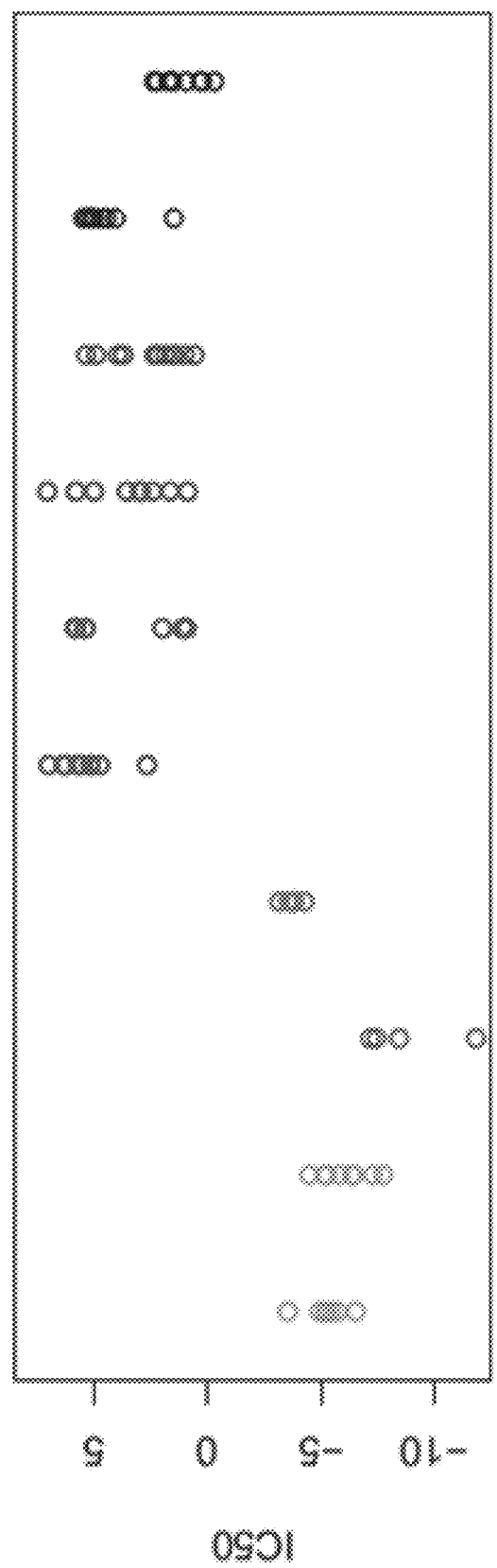
FIG. 10A illustrates drug responsive data for a plurality of drugs for a soft-tissue cancer.
Figure 10B:
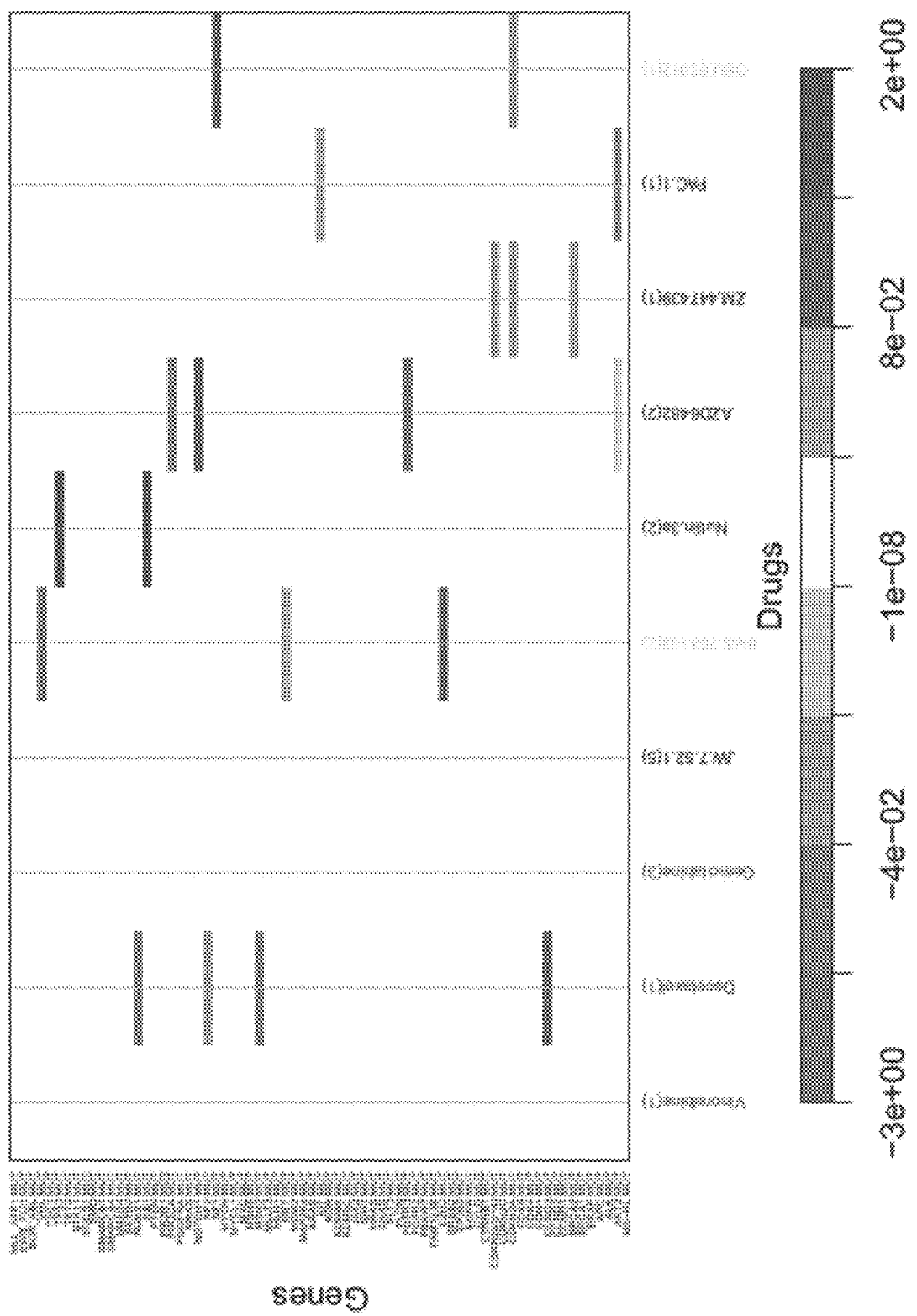
FIG. 10B illustrates a plot of estimate coefficient matrix showing drugs for different genes, in accordance with an example.
Figure 11A:
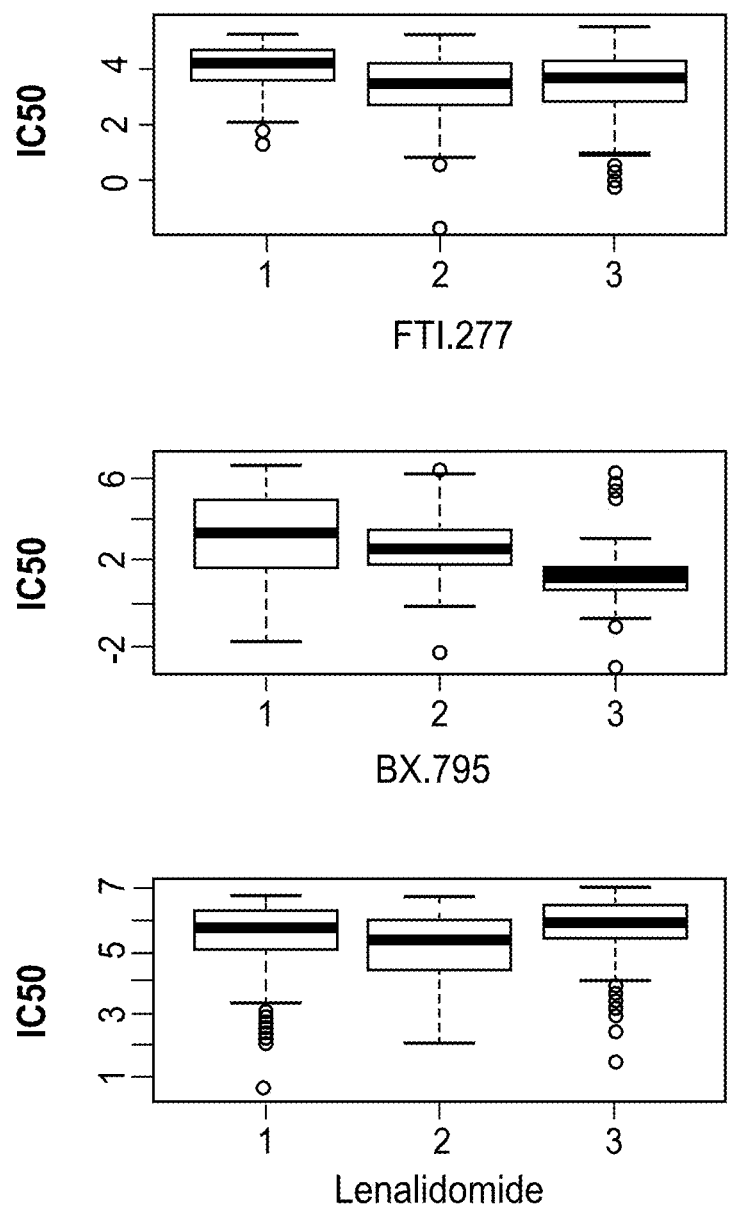
FIGS. 11A-11E illustrate the drug responsiveness data for a plurality of drugs out of a larger examined listing of drugs.
Figure 11B:
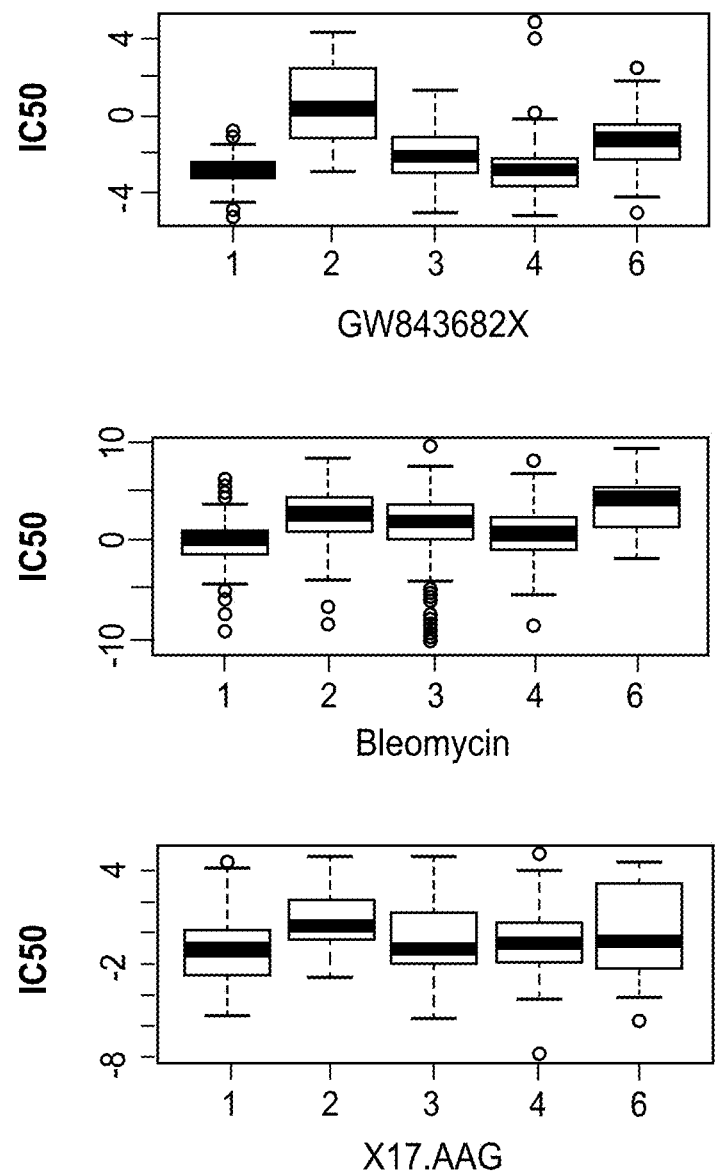
Figure 11C:
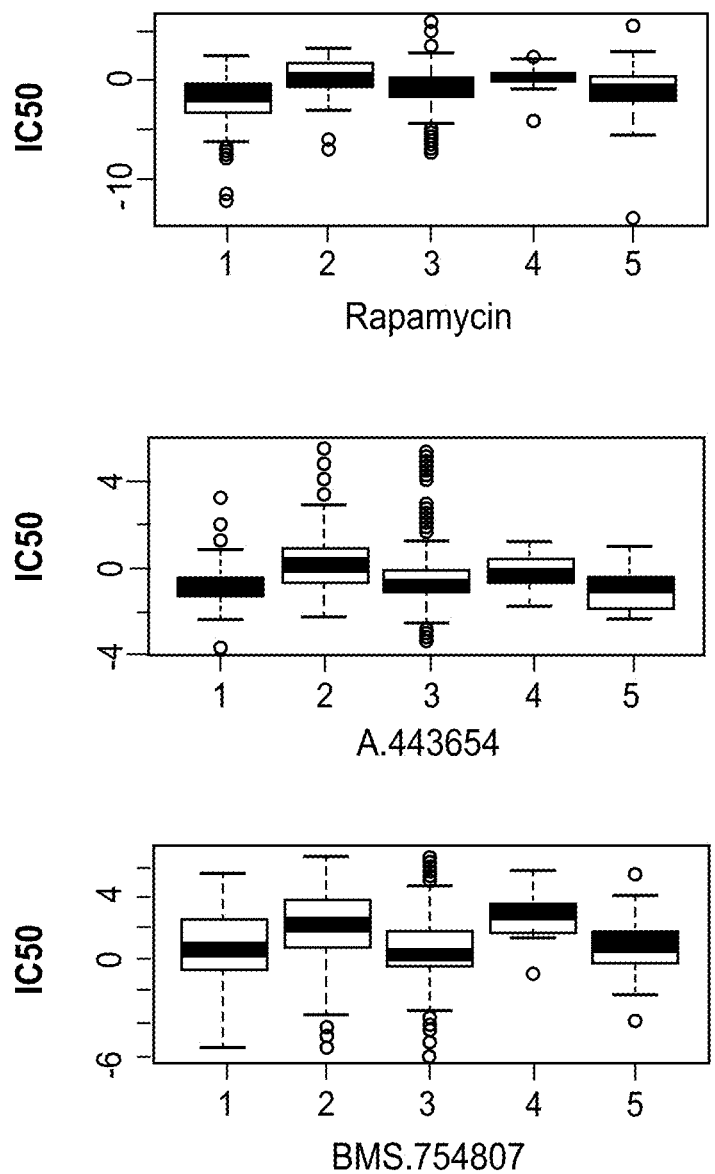
Figure 11D:
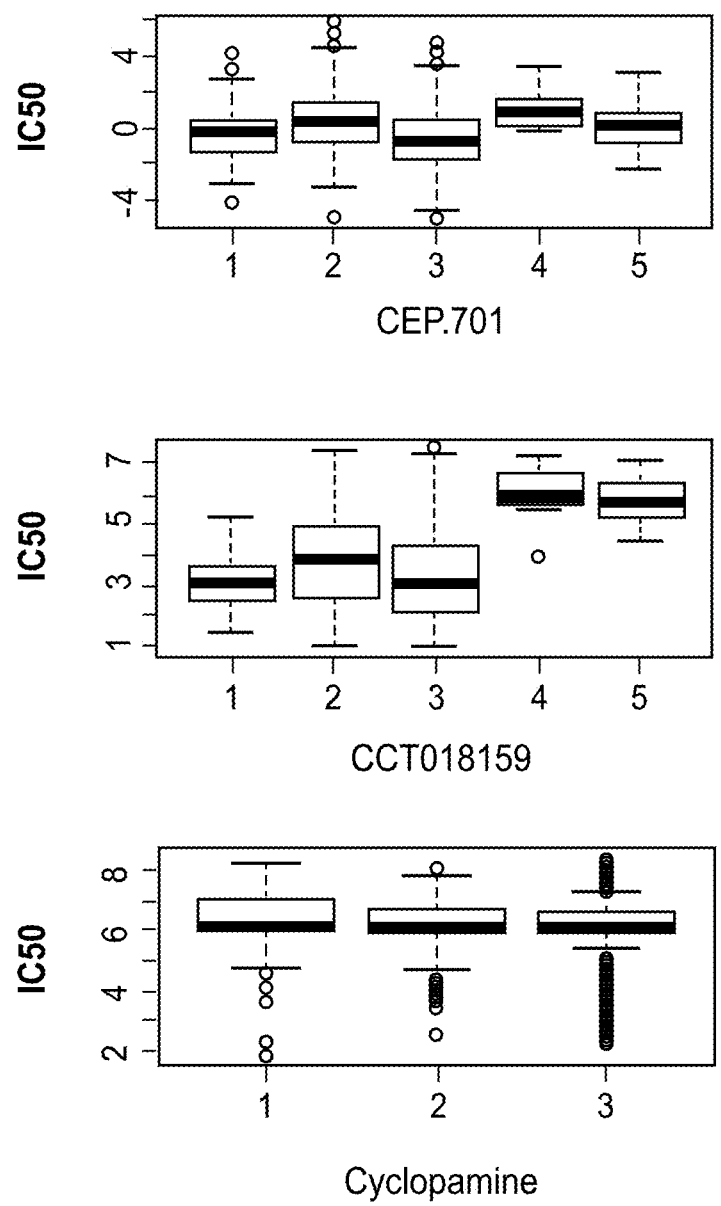
Figure 11E:
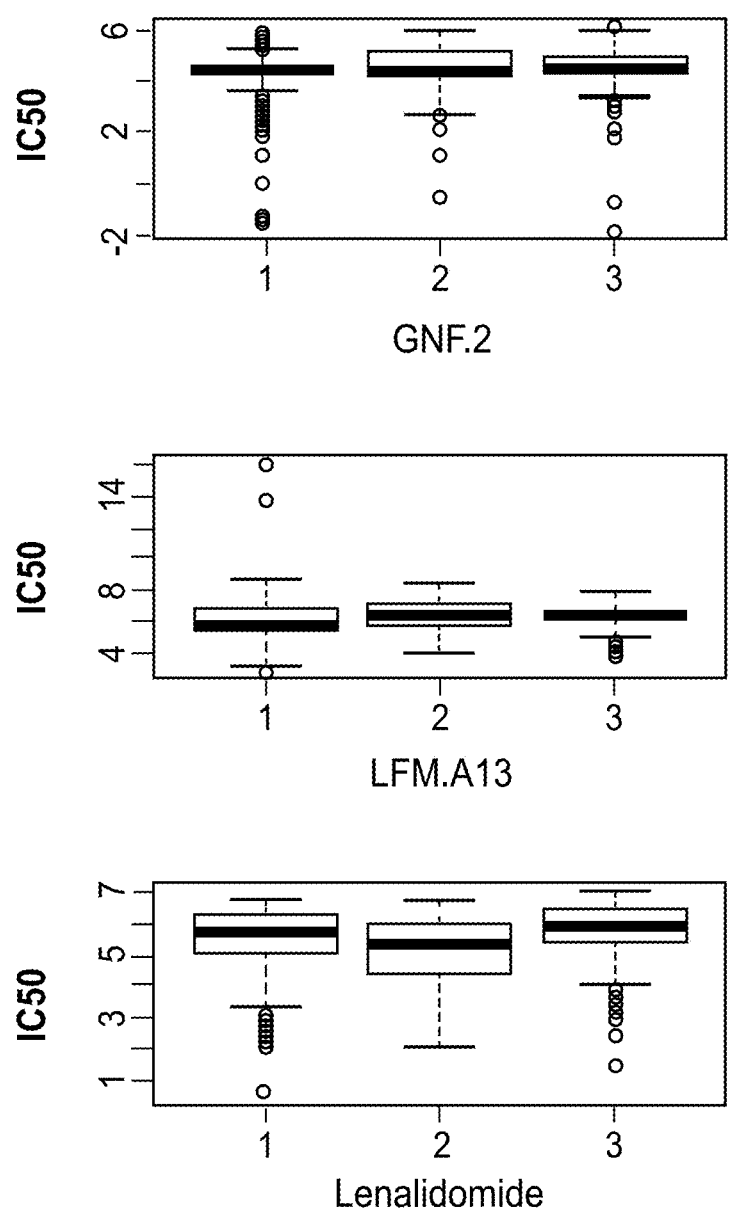

FIGS. 7A-7B and FIGS. 8A-8B are similar to FIGS. 5A, 5B, 6A, and 6B, except that they only show a subset of $\hat{B}_1^C$ and $\hat{B}_{12}^C$ with regard to the mutations of 71 cancer genes, where $\hat{B}_{12}^C = \hat{B}_1^C + \hat{B}_2^C$ are coefficient estimates of component 12 for drug group C. The present techniques can be used for drug repurposing (Martins, Zhou, Corella, Horiuchi, Yau, Rakshandehroo, Gordan, Levin, Johnson, Jascur et al. 2015) for resistant tumors. FIGS. 7A-7B and FIGS. 8A-8B are regression based drug-genetic association maps (bottom panel) with red indicating drug-sensitivity biomarkers and blue indicating drug-resistance biomarkers, conditioning on a component of cell lines (upper panel) identified through the generalized FMMR model. We focus the process on soft-tissue cancers as an example of this drug repurposing. The process extracted those cell line components which contain a high percentage of soft-tissue cancer (large purple bubbles), along with the subset component-wise coefficient estimates. The extracted information is presented in FIGS. 9A and 9B. FIG. 9A showing the $IC_{50}$ values of soft-tissue cell lines in extracted cell line components. Extracted drugs in FIGS. 9A and 9B are further filtered, by the processes herein, by only keeping those that have a low $IC_{50}$ value without resistance biomarkers and that have a high $IC_{50}$ value with resistance biomarkers, leading to FIGS. 10A and 10B. As shown in these figures, the process herein is able to determine that the former set of drugs can be used as alternatives for the later set of drugs, which progress resistance to soft tissue cancer. Table 1, FIG. 16, provides a summary of all pairwise drug combinations found in the dataset that are predicted in this way for soft tissue cancers. As a positive control (represented by a * in Table 1), of this strategy, we find that drug Gemcitabine was found to be effective in soft tissue cancer resistant to standard chemotherapy (doxyrubicin) in a small sample size phase II study (Merimsky, Meller, Flusser, Kollender, Issakov, Weil-Ben-Arush, Fenig, Neuman, Sapir, Ariad et al. 2000).

Overlapping cell lines can be used to guide drug combinations and identify potential drug synergies. Based on estimates of cell line assignments $\hat{Z}_C$, the process can cluster the $IC_{50}$ values with respect to cell line components for each drug.

FIG. 11A-11E are boxplots of the resulting component-wise $IC_{50}$ values for 15 out of 140 drugs. Due to limited space, the rest are not shown. As indicated in the illustrated example, the present techniques are able to automatically identify drugs for which the magnitude of $IC_{50}$s for overlapping component, say 12, is between those for component 1 and 2. Drugs MS.275 and GW843682X show such interesting pattern. Next, the process can determine the component with highest $IC_{50}$ and try to decrease its $IC_{50}$s towards overlapping component. Take GW843682X for an example, component 2 has the highest $IC_{50}$ among components 1, 2, and 12. The process can do initial predictions that the $IC_{50}$s for cell lines in component 2 using $\hat{B}_1^{gw843682x}$, $\hat{B}_2^{gw843682x}$ and $\hat{B}_2^{gw843682x}$ respectively. Predicted results as well as the observations are shown in top panel (middle) of FIG. 12A. By doing so, the process can determine if coefficients $\hat{B}_1^{gw843682x}$ and $\hat{B}_{12}^{gw843682x}$ applied to cell lines in component 2 can generate lower $IC_{50}$s similar to that in component 1 and 12. This type of determination can be performed by the processes herein without actually physically testing the drug data on a cell line, but rather the determination is made from drug data, biomarker response, cell line data, etc. Since $\hat{B}_1^{gw843682x}$ corresponds to the coefficient estimates of drug GW843682X regressing on its cell line component 1, we want to find another drug which produces similar coefficient estimates as $\hat{B}_1^{gw843682x}$. The process automatically identifies coefficient estimates $\hat{B}_3^{epothilone.b}$ are found highly correlated with $\hat{B}_1^{gw843682x}$. And the predicted $IC_{50}$s for cell lines in component 2 using $\hat{B}_3^{epothilone.b}$, $B_2^{gw843682x}$ and $\hat{B}_3^{epothilone.b} + \hat{B}_2^{gw843682x}$ are presented in bottom panel (middle) of FIG. 12B. It is shown that the drug combination of GW843682X and Epothilone.B decreases the $IC_{50}$s dramatically.

Similar studies were conducted for drug MS.275 with respect to component 1, 2, and 12 and for drug GW843682X with respect to component 2, 3 and 23. Results are shown in left and right columns of FIGS. 12A and 12B, respectively. The combination of GW843682X and NVP.BEZ235 is effective in decreasing the $IC_{50}$s, while the combination of MS.275 and Bicalutamide does not show the effectiveness. As a positive control, Wildey, Chen, Lent, Stetson, Pink, Barnholtz-Sloan and Dowlati (2014) pointed out that a group of drugs (including GW-843682X and Epothilone B) may provide a practical starting point to investigate combinatorial drug therapies for synergistic effect in small-cell lung cancer (SCLC). Among the cluster of drugs, they found synergism between GW-843682X and CGP-60474 via a preliminary study.

Figure 12A:
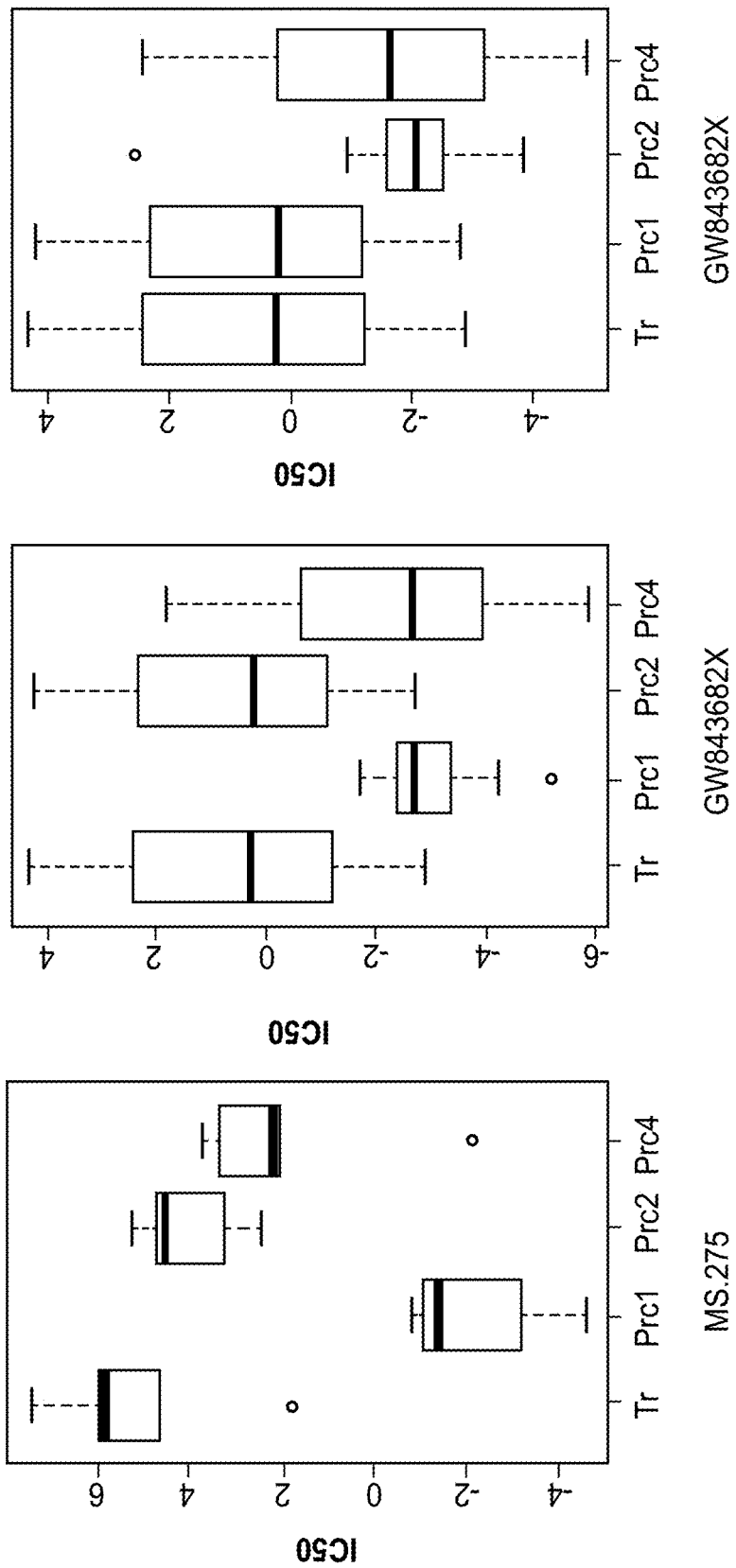
FIGS. 12A and 12B illustrate predicted drug responsive data for different combination combinations, in accordance with an example.
Figure 12B:
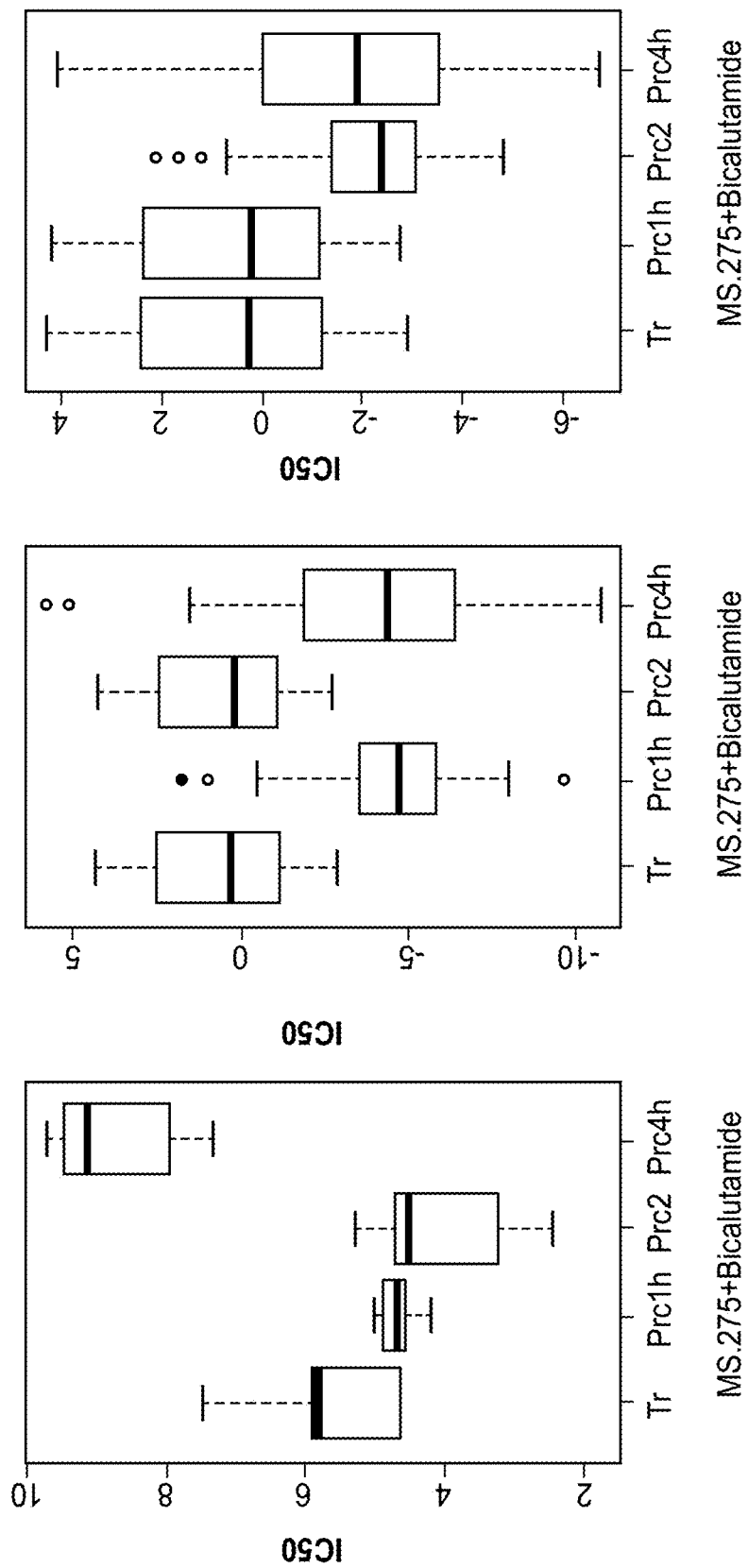

In FIGS. 12A and 12B, the indications Prc1 and Prc1h indicate a cell line of a first genomic profile and Prc2 and represent a second genomic profile for that cell line. For example, the plot for Prc1(h) may represent $IC_{50}$ drug responsiveness data for the plotted drug for a soft tissue cancer cell line having a first genomic profile. Prc2 may then represent a mutation of that soft tissue cancer cell line. The present techniques, as described, can then analyze drugs by their drug grouping to identify drugs producing an IC50 value in a desired range, between the max and mix $IC_{50}$ values of the two cell lines, and specifically a drug that corresponds to an overlapping cluster drug cell line (e.g., Prc4h) that includes at least some of the genomic profile of the first cell line (Prc1(h)) and at least some of the genomic profile of the second cell line (Prc2). As shown, for example, because GW843682X+Epothilone.B produces an $IC_{50}$ responsive to an overlapping cluster cell line Prc4H, that drug GW843682X+Epothilone.B is automatically identified by the processes as a potential for treating the cancer of a patient having either the Prc1 or Prc2 cancer cell lines.

Any number of cell lines can be examined against drugs and drug combinations, with the present techniques. Examples include cells that are cancer cells, including but not limited to thyroid cancer cells, soft tissue cancer cells, skin cancer cells, pancreatic cancer cells, nervous system cancer cells, lung cancer cells, kidney cancer cells, digestive system cancer cells, breast cancer cells, bone cancer cells, blood cancer cells, digestive tract cancer cells, and urogenital cancers cells.

In some of the examples, at least some examined cell lines correspond to a primary cancer, and wherein an overlapping cell line cluster corresponds to the primary cancer. In yet other examples, at least some of cell lines correspond to a primary cancer, and an overlapping cell line cluster includes a secondary cancer different than the primary cancer.

The present techniques can automatically identify, from a database of drugs, plurality of alternative drugs exhibiting a drug responsiveness value between a high drug responsiveness value and a low drug responsiveness value, such that the alternative drugs have the highest drug responsiveness for the overlapping cell line cluster. This can be used to maximize the likelihood of success of the alternative drugs. In automated drug delivery systems, the alternative drug may then be administered to the overlapping cell line cluster for testing.

We note that an alternative drug may comprise at least one drug combination comprising a treatment drug and an additive drug. In other examples, the alternative drug comprises at least one drug combination that does not contain the treatment drug.

Figure 13:
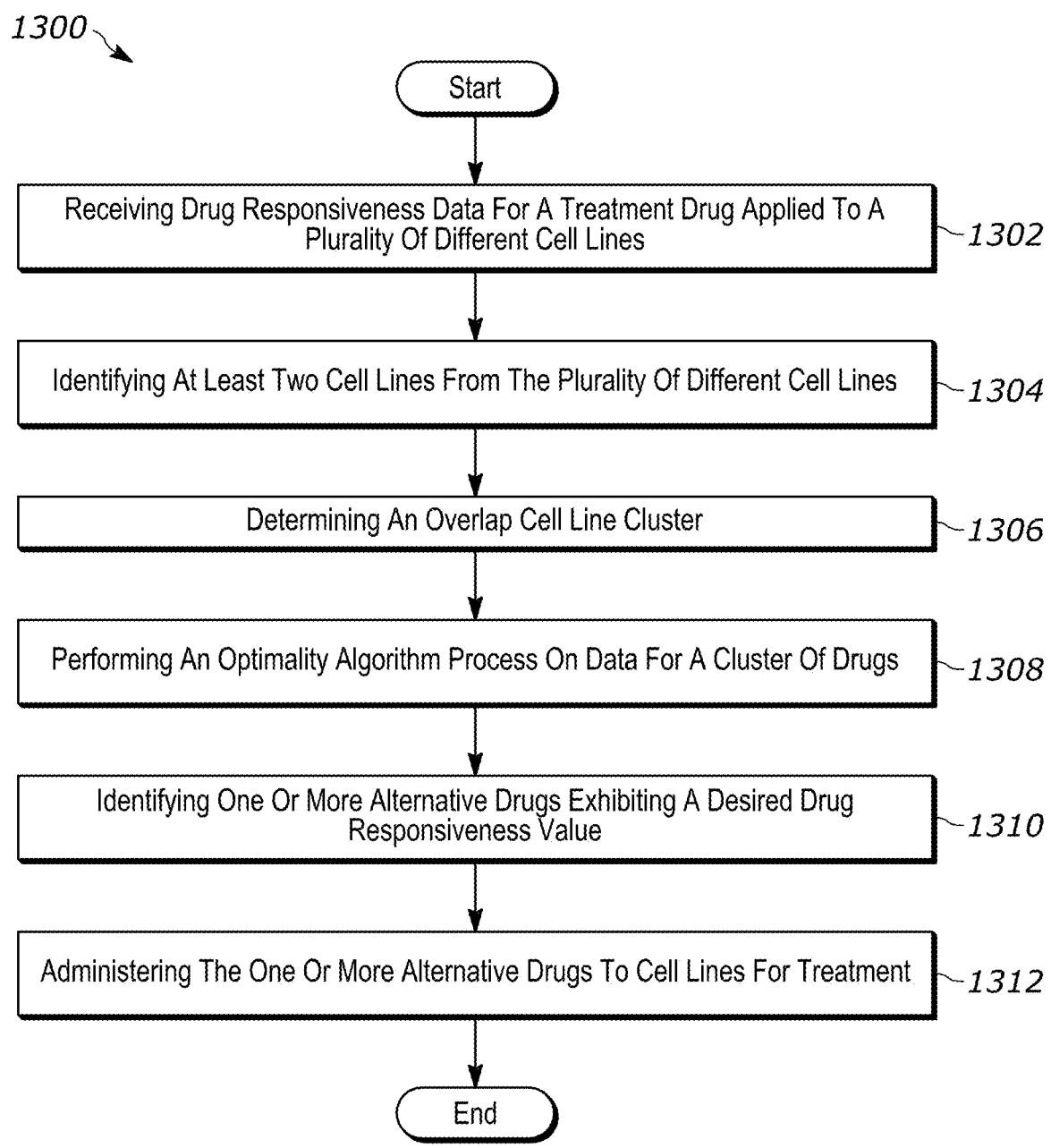
FIG. 13 illustrates a process for clustering (or grouping) drugs and identifying alternative drugs based on drug responsive data such as that of FIGS. 12A and 12B, in accordance with an example.
Figure 14:
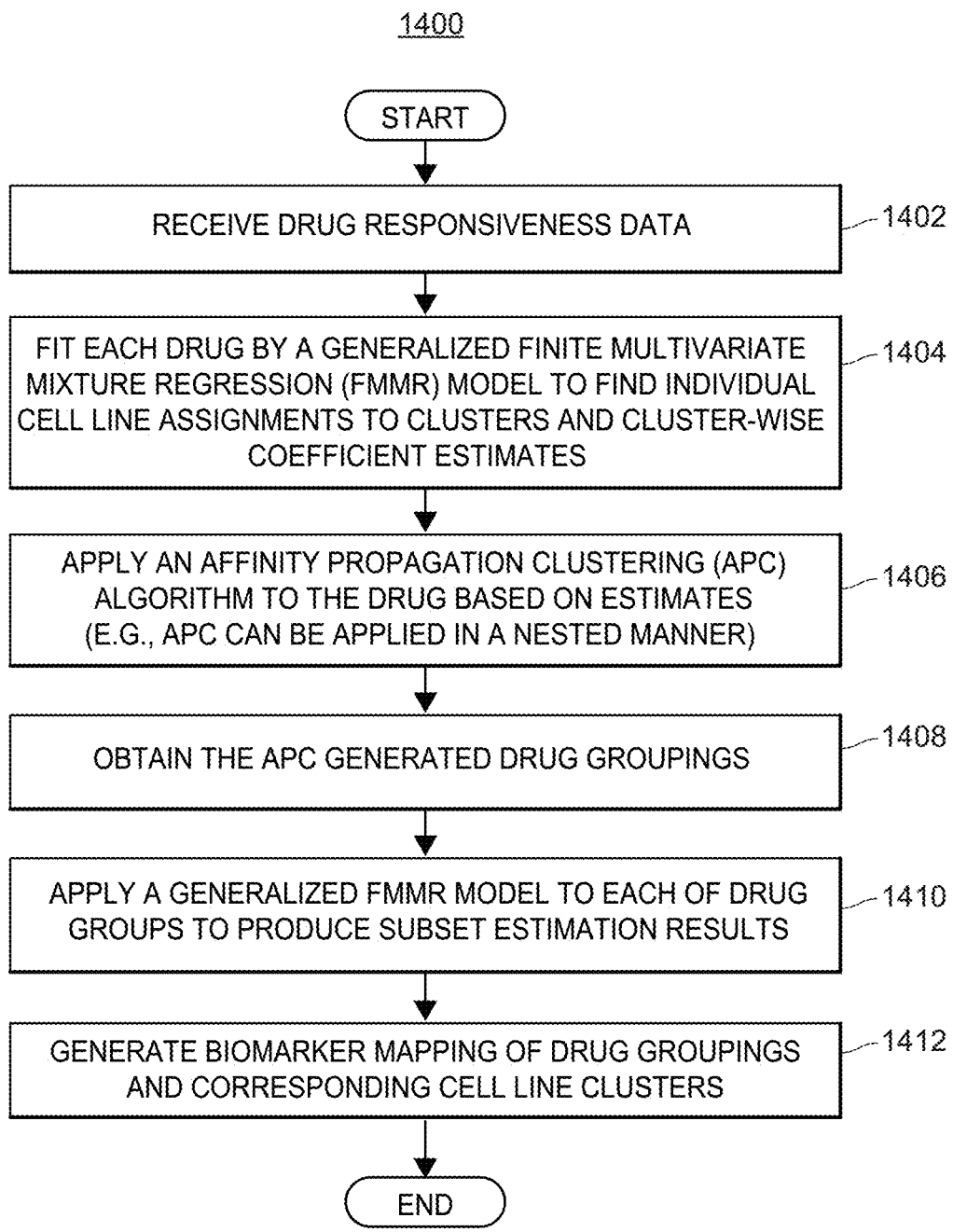
FIG. 14 illustrates a process for clustering (or grouping) drugs and generating biomarker mapping of drug groupings corresponding to the cell line clusters of FIG. 13, in accordance with an example.

FIGS. 13 and 14 illustrate example processes for identifying alternative treatment drugs from drug cluster groupings and processes for generating biomarker mappings of drug cluster groupings for different cell lines, respectively. For process 1300 (FIG. 13), at a block 1302, drug responsiveness data is received at a drug analysis computing system. The drug responsiveness data may corresponding to drug treatment data for a drug applied to a one or more different cell lines. Such drug treatment data may include, by way of example, drug test data on drugs applied to patient cell lines. In response to the treatment data, the drug analysis computing system (at a block 1304) identifies two or more cell lines from the plurality of different cell lines. For example, the drug analysis computing system may be configured to use any number of criteria to identify initial cell lines. Cell lines could be selected randomly in some examples. In some examples patient data may be used to determine initial cell lines. In some examples, cell lines are chosen to introduce a sufficient amount of diversity in patients represented for drug analysis. At a block 1306, the drug analysis computing system implements one or more of the clustering grouping analysis techniques herein to determine an overlapping cell line cluster, from the among the identified cell lines. For example, the drug analysis computing system may apply a model-based overlapping clustering framework, as described herein, e.g., a multivariate regression model analysis, such as a finite mixture of multivariate regression model and EM algorithm.

At a block 1308, an optimality algorithm process is performed on data for a cluster of drugs 1308, as the implementation of Algorithm 1. From the optimization, one or more alternative drugs are identified (block 1310), drugs exhibiting a desired drug responsiveness, measured as a $IC_{50}$ value. With the drugs being identified, the one or more alternative drugs may then be applied to cell lines for treatment (1312) and for collecting new drug responsiveness data.

FIG. 14 illustrates a process 1400, which may be an example implementation of the process 1300, in accordance with examples herein. Initially, drug responsiveness data is received to a drug analysis computing system at a block 1402. At a block 1404, the drug analysis computing system fits each drug by a generalized finite multivariate mixture regression (FMMR) model and identifies individual cell line assignments to clusters and cluster-wise coefficient estimates. An affinity propagation clustering (APC) algorithm is applied to the drug data, based on estimates, at a block 1406. In some examples, the APC may be applied in a nested manner. From there, APC generated drug groupings are generated and stored (block 1408). These groupings may group drugs based on correlations of responsiveness, commonality of drug targets or biological pathways, or other factors, for example. A generalized FMMR model is then applied to each drug group to produce a subset of estimation results of drug responsiveness, at a block 1410. At block 1412, the drug analysis computing system generates a biomarker mapping of drug groupings and corresponding cell line clusters for treatment by these drug groupings. The mappings may be based on cell lines as described, while in other examples, the mappings may be based on gene expression, as shown in the example generated biomarker mapping in FIGS. 7, 8, 9, and 10.

Figure 15:
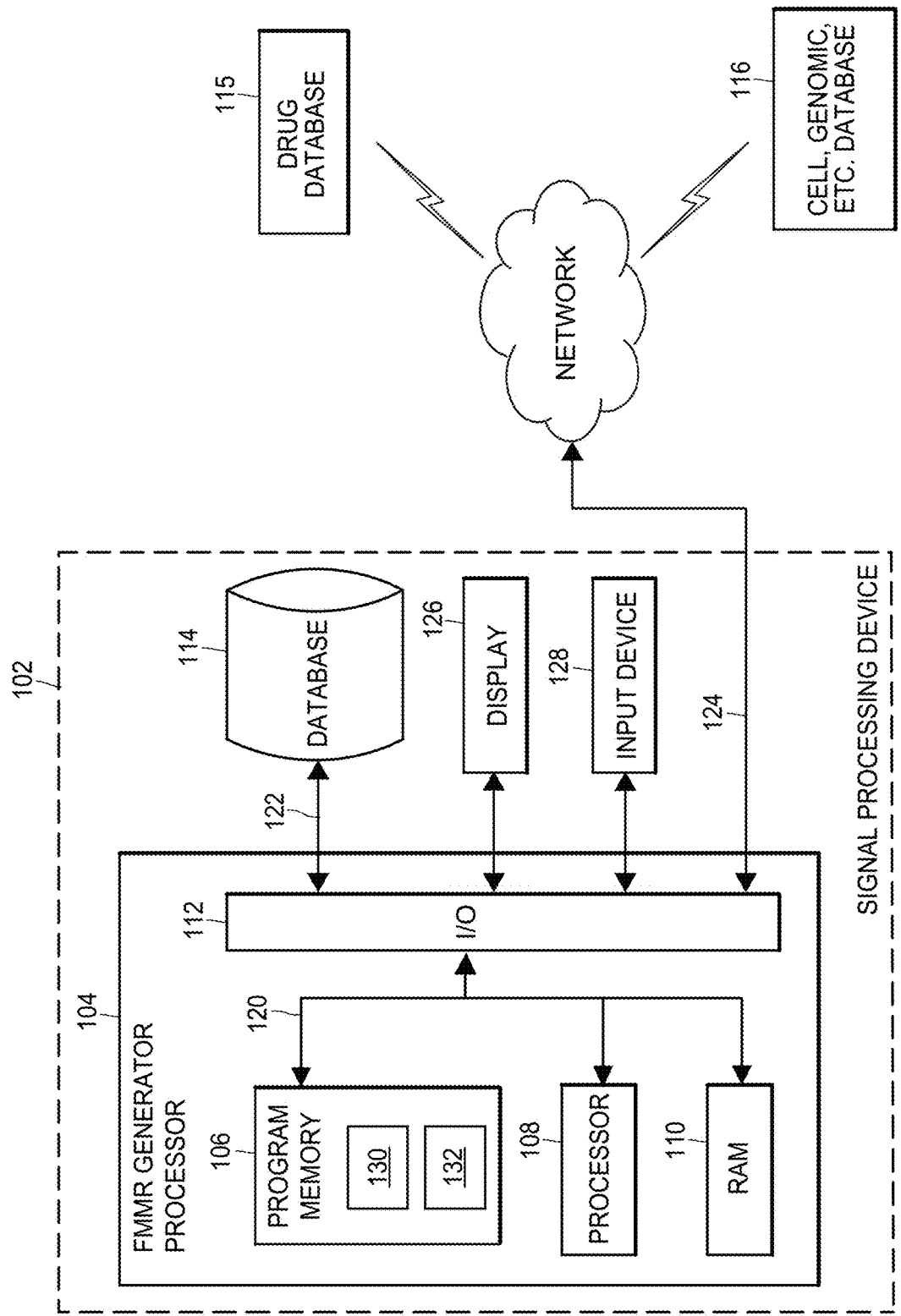
FIG. 15 illustrates a drug analysis system for implementing the techniques herein, in accordance with an example.

FIG. 15 illustrates an example drug analysis system 100 that illustrates various components used in implementing an example embodiment of the present techniques. A signal-processing device 102 (or "signal processor" or "diagnostic device") is configured to collect cancer cell, gene, genomic, demographic, drug, and other data from example databases 116 and 115 connected to the single processing device through a wireless (or wired) network 117. The signal-processing device 102 may have a generalized FMMR model generator 104 operatively connected to an internal database 114 (that may alternatively drug protein and/or cancer cell and other data) via a link 122 connected to an input/output (I/O) circuit 112. It should be noted that, while not shown, additional databases may be linked to the generalized FMMR model generator 104 in a known manner. The generator processor 104 includes a program memory 106, one or more processors 108 (may be called microcontrollers or a microprocessors), a random-access memory (RAM) 110, and the input/output (I/O) circuit 112, all of which are interconnected via an address/data bus 120. It should be appreciated that although only one processor 108 is shown, the generator 104 may include multiple microprocessors 108. Similarly, the memory of the generator 104 may include multiple RAMs 110 and multiple program memories 106. Although the I/O circuit 112 is shown as a single block, it should be appreciated that the I/O circuit 112 may include a number of different types of I/O circuits. The RAM(s) 110 and the program memories 106 may be implemented as semiconductor memories, magnetically readable memories, and/or optically readable memories, for example. A link 124, which may include one or more wired and/or wireless (Bluetooth, WLAN, etc.) connections, may operatively connect the matrix generator 104 to the databases 115 and 116 through the I/O circuit 112. In other examples, the databases 115 and 116 may be part of the signal-processing device 102.

The program memory 106 and/or the RAM 110 may store various applications (i.e., machine readable instructions) for execution by the processor 108. For example, an operating system 130 may generally control the operation of the signal-processing device 102 and provide a user interface to the signal-processing device 102 to implement data processing operations. The program memory 106 and/or the RAM 110 may also store a variety of subroutines 132 for accessing specific functions of the signal-processing device 102. By way of example, and without limitation, the subroutines 132 may include, among other things: a subroutine to perform the process steps of FIGS. 13 and/or 14 or any of the other processes described herein.

The subroutines 132 may also include other subroutines, for example, implementing software keyboard functionality, interfacing with other hardware in the signal processing device 102, etc. The program memory 106 and/or the RAM 110 may further store data related to the configuration and/or operation of the signal-processing device 102, and/or related to the operation of the one or more subroutines 132. For example, the data may be data gathered from the databases 115 and 116, data determined and/or calculated by the processor 108, etc. In addition to the matrix generator 104, the signal-processing device 102 may include other hardware resources. The signal-processing device 102 may also include various types of input/output hardware such as a visual display 126 and input device(s) 128 (e.g., keypad, keyboard, etc.). In an embodiment, the display 126 is touch-sensitive, and may cooperate with a software keyboard routine as one of the software routines 132 to accept user input.

It may be advantageous for the signal-processing device 102 to communicate with a medical treatment device, medical drug testing databases, biomarker/genomic testing databases, medical data records storage device, through the network 117 or through any of a number of known networking devices and techniques (e.g., through a commuter network such as a hospital or clinic intranet, the Internet, etc.). For example, the signal-processing device may be connected to a medical records database, hospital management processing system, healthcare professional terminals (e.g., doctor stations, nurse stations), high throughput screening framework, drug/biomarker databases, or other system.

The system 100 may be implemented as computer-readable instructions stored on a single dedicated machine, for example, one with one or more computer processing units. In some examples, the dedicated machine performs only the functions described in the processes of FIGS. 1-14, and any other functions needed to perform those processes. The dedicated machine may be a standalone machine or embedded within another computing machine.

In some examples, one or more of the functions of the system 100 may be performed remotely, including, for example, on a server connected to a remote computing device, through a wired or wireless interface at 112 and the network 117. Such distributed processing may include having all or a portion of the processing of system 100 performed on a remote server. In some embodiments, the techniques herein may be implemented as software-as-a-service (SaaS) with the computer-readable instructions to perform the method steps being stored on one or more of the computer processing devices and communicating with one or more user devices, including but not limited to personal computers, handheld devices, etc.

Provided are computer-implemented processes built upon new models for identifying therapeutic biomarkers for cancer and other pathologies, where these techniques can answer specific questions regarding sensitivity, resistance and synergy across large sets of possible treatment drugs. In an example, a penalized likelihood approach for an FMMR model was used and which enforced sparsity in the genomic features. To enable overlapping clustering, the FMMR model was then generalized and a new EM algorithm derived for estimation of model parameters implemented. While the noteworthy plaid model can also be generalized for overlapping clustering multivariate regression data, the generalized FMMR model markedly outperforms that method.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of the example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but also deployed across a number of machines. In some example embodiments, the processor or processors may be located in a single location (e.g., within a home environment, an office environment or as a server farm), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., application program interfaces (APIs).)

The performance of certain of the operations may be distributed among the one or more processors, not only residing within a single machine, but also deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

The foregoing description is given for clearness of understanding; and no unnecessary limitations should be understood therefrom, as modifications within the scope of the invention may be apparent to those having ordinary skill in the art.

REFERENCES

Akaike, H. (1974), "A new look at the statistical model identification," IEEE transactions on automatic control, 19(6), 716-723.

Anderson, D. R., and Burnham, K. P. (2002), "Avoiding pitfalls when using information-theoretic methods," The Journal of Wildlife Management, pp. 912-918.

Azzalini, A. (2005), "The skew-normal distribution and related multivariate families," Scandinavian Journal of Statistics, 32(2), 159-188.

Baeza-Yates, R., Ribeiro-Neto, B. et al. (1999), Modern information retrieval, Vol. 463 ACM press New York.

Bailey, A. M., Mao, Y., Zeng, J., Holla, V., Johnson, A., Brusco, L., Chen, K., Mendelsohn, J., Routbort, M. J., Mills, G. B. et al. (2014), "Implementation of biomarker-driven cancer therapy: existing tools and remaining gaps," Discovery medicine, 17(92), 101.

Banerjee, A., Krumpelman, C., Ghosh, J., Basu, S., and Mooney, R. J. (2005), Model-based overlapping clustering, in Proceedings of the eleventh ACM SIGKDD international conference on Knowledge discovery in data mining, ACM, pp. 532-537.

Barretina, J., Caponigro, G., Stransky, N., Venkatesan, K., Margolin, A. A., Kim, S., Wilson, C. J., Leh ar, J., Kryukov, G. V., Sonkin, D. et al. (2012), "The Cancer Cell Line Encyclopedia enables predictive modeling of anticancer drug sensitivity," Nature, 483(7391), 603-607.

Branco, M. D., and Dey, D. K. (2001), "A general class of multivariate skew-elliptical distributions," Journal of Multivariate Analysis, 79(1), 99-113.

Breiman, L., and Friedman, J. H. (1997), "Predicting multivariate responses in multiple linear regression," Journal of the Royal Statistical Society: Series B (Statistical Methodology), 59(1), 3-54.

Chen, L., Pourahmadi, M., and Maadooliat, M. (2014), "Regularized multivariate regression models with skew-t error distributions," Journal of Statistical Planning and Inference, 149, 125-139.

Claeskens, G., Hjort, N. L. et al. (2008), Model selection and model averaging, Vol. 330 Cambridge University Press Cambridge.

Dempster, A. P., Laird, N. M., and Rubin, D. B. (1977), "Maximum likelihood from incomplete data via the EM algorithm," Journal of the royal statistical society. Series B (methodological), pp. 1-38.

DeSarbo, W. S., and Cron, W. L. (1988), "A maximum likelihood methodology for clusterwise linear regression," Journal of classification, 5(2), 249-282.

Druker, B. J., Guilhot, F., O'Brien, S. G., Gathmann, I., Kantarjian, H., Gattermann, N., Deininger, M. W., Silver, R. T., Goldman, J. M., Stone, R. M. et al. (2006), "Five-year follow-up of patients receiving imatinib for chronic myeloid leukemia," New England Journal of Medicine, 355(23), 2408-2417.

Estivill-Castro, V. (2002), \Why so many clustering algorithms: a position paper," ACM SIGKDD explorations newsletter, 4(1), 65-75.

Fan, J., and Li, R. (2006), "Statistical challenges with high dimensionality: Feature selection in knowledge discovery," arXiv preprint math/0602133.

Fan, J., and Lv, J. (2010), "A selective overview of variable selection in high dimensional feature space," Statistica Sinica, 20(1), 101.

Fraley, C., and Raftery, A. E. (1998), "How many clusters? Which clustering method? Answers via model-based cluster analysis," The computer journal, 41(8), 578-588.

Frey, B. J., and Dueck, D. (2007), "Clustering by passing messages between data points," science, 315(5814), 972-976.

Fu, Q., and Banerjee, A. (2008), Multiplicative mixture models for overlapping clustering, in 2008 Eighth IEEE International Conference on Data Mining, IEEE, pp. 791-796.

Galimberti, G., and Soffritti, G. (2014), "A multivariate linear regression analysis using finite mixtures of t distributions," Computational Statistics & Data Analysis, 71, 138-150.

Garnett, M. J., Edelman, E. J., Heidorn, S. J., Greenman, C. D., Dastur, A., Lau, K. W., Greninger, P., Thompson, I. R., Luo, X., Soares, J. et al. (2012), "Systematic identification of genomic markers of drug sensitivity in cancer cells," Nature, 483(7391), 570-575.

Grun, B., and Leisch, F. (2008), "FlexMix version 2: finite mixtures with concomitant variables and varying and constant parameters,".

Heller, K. A., and Ghahramani, Z. (2007), A Nonparametric Bayesian Approach to Modeling Overlapping Clusters, in AISTATS, pp. 187-194.

Ishwaran, H., Kogalur, U. B., Blackstone, E. H., and Lauer, M. S. (2008), "Random survival forests," The annals of applied statistics, pp. 841-860.

Jain, A. K., Murty, M. N., and Flynn, P. J. (1999), "Data clustering: a review," ACM computing surveys (CSUR), 31(3), 264-323.

Jedidi, K., Ramaswamy, V., DeSarbo, W. S., and Wedel, M. (1996), "On estimating finite mixtures of multivariate regression and simultaneous equation models," Structural Equation Modeling: A Multidisciplinary Journal, 3(3), 266-289.

Jiang, J., Nguyen, T., and Rao, J. S. (2015), "The E-MS algorithm: model selection with incomplete data," Journal of the American Statistical Association, 110(511), 1136-1147.

Jones, P., and McLachlan, G. (1992), "Fitting finite mixture models in a regression context," Australian Journal of Statistics, 34(2), 233-240.

Keribin, C. (2000), "Consistent estimation of the order of mixture models," Sankhy a: The Indian Journal of Statistics, Series A, pp. 49-66.

Khalili, A., and Chen, J. (2012), "Variable selection in finite mixture of regression models," Journal of the American Statistical Association.

Khalili, A., and Lin, S. (2013), "Regularization in finite mixture of regression models with diverging number of parameters," Biometrics, 69(2), 436-446.

Lazzeroni, L., and Owen, A. (2002), "Plaid models for gene expression data," Statistica sinica, pp. 61-86.

Leisch, F. (2004), "Flexmix: A general framework for finite mixture models and latent glass regression in R".

Martins, M. M., Zhou, A. Y., Corella, A., Horiuchi, D., Yau, C., Rakshandehroo, T., Gordan, J. D., Levin, R. S., Johnson, J., Jascur, J. et al. (2015), "Linking Tumor Mutations to Drug Responses via a Quantitative Chemical-Genetic Interaction Map," Cancer discovery, 5(2), 154-167.

Merimsky, O., Meller, I., Flusser, G., Kollender, Y., Issakov, J., Weil-Ben-Arush, M., Fenig, E., Neuman, G., Sapir, D., Ariad, S. et al. (2000), "Gemcitabine in soft tissue or bone sarcoma resistant to standard chemotherapy: a phase II study," Cancer chemotherapy and pharmacology, 45(2), 177-181.

Needham, R. (1965), "Computer methods for classification and grouping," The Use of Computers in Anthropology, I. Hymes, ed, pp. 345-356.

Peng, J., Zhu, J., Bergamaschi, A., Han, W., Noh, D.-Y., Pollack, J. R., and Wang, P. (2010), "Regularized multivariate regression for identifying master predictors with application to integrative genomics study of breast cancer," The annals of applied statistics, 4(1), 53.

Quandt, R. E. (1972), "A new approach to estimating switching regressions," Journal of the American statistical association, 67(338), 306-310.

Rothman, A. J., Levina, E., and Zhu, J. (2010), "Sparse multivariate regression with covariance estimation," Journal of Computational and Graphical Statistics, 19(4), 947-962.

Schwarz, G. et al. (1978), "Estimating the dimension of a model," The annals of statistics, 6(2), 461-464.

Segal, E., Battle, A., and Koller, D. (2002), Decomposing gene expression into cellular processes, in Proceedings of the Pacific Symposium on Biocomputing, Vol. 8, pp. 89-100.

Similä, T., and Tikka, J. (2007), "Input selection and shrinkage in multiresponse linear regression," Computational Statistics & Data Analysis, 52(1), 406-422.

Soffritti, G., and Galimberti, G. (2011), "Multivariate linear regression with non-normal errors: a solution based on mixture models," Statistics and Computing, 21(4), 523-536.

Stekhoven, D. J., and Bühlmann, P. (2012), "MissForestnonparametric missing value imputation for mixed-type data," Bioinformatics, 28(1), 112-118.

Stone, M. (1977), "An asymptotic equivalence of choice of model by cross-validation and Akaike's criterion," Journal of the Royal Statistical Society. Series B (Methodological), pp. 44-47.

Tibshirani, R. (1996), "Regression shrinkage and selection via the lasso," Journal of the Royal Statistical Society. Series B (Methodological), pp. 267-288.

Turlach, B. A., Venables, W. N., and Wright, S. J. (2005), "Simultaneous variable selection," Technometrics, 47(3), 349-363.

Turner, H., Bailey, T., and Krzanowski, W. (2005), "Improved biclustering of microarray data demonstrated through systematic performance tests," Computational statistics & data analysis, 48(2), 235-254.

Turner, H. L., Bailey, T. C., Krzanowski, W. J., and Hemingway, C. A. (2005), "Biclustering models for structured microarray data," IEEE/ACM Transactions on Computational Biology and Bioinformatics (TCBB), 2(4), 316-329.

Wildey, G., Chen, Y., Lent, I., Stetson, L., Pink, J., Barnholtz-Sloan, J. S., and Dowlati, A. (2014), "Pharmacogenomic approach to identify drug sensitivity in small-cell lung cancer," PloS one, 9(9), e106784.

Zhang, J. (2010), "A Bayesian model for biclustering with applications," Journal of the Royal Statistical Society: Series C (Applied Statistics), 59(4), 635-656.

Zou, H., and Hastie, T. (2005), "Regularization and variable selection via the elastic net," Journal of the Royal Statistical Society: Series B (Statistical Methodology), 67(2), 301-320.

What is claimed:

1. A method of identifying alternative drug therapies, the method comprising:
receiving, at a processing unit, drug responsiveness data for a treatment drug applied to a plurality of different cell lines, each cell line differing in genomic profile from one another such that the genomic profiles for the plurality of different cell lines are mutually exclusive, the drug responsiveness data being determined from live cell testing using the treatment drug;
identifying at least two cell lines from the plurality of different cell lines, and determining, at the processing unit, an overlap cell line cluster where one of the at least two cell lines has a high drug responsiveness value and another of the at least two cell lines has a low drug responsiveness value, and wherein the overlap cell line cluster has a drug responsiveness value for the treatment drug that is between the high drug responsiveness value and the low drug responsiveness value, wherein determining the overlap cell line cluster using a generalized finite mixture of multivariate regression (FMMR) model;
performing, at the processing unit, an optimality algorithm process on data for a cluster of drugs to identify one or more alternative drugs exhibiting a drug responsiveness value between the high drug responsiveness value and the low drug responsiveness value; and
administering to cells of one of the at least two cell lines the one or more alternative drugs.

2. The method of claim 1, wherein the cells are cancer cells, including but not limited to thyroid cancer cells, soft tissue cancer cells, skin cancer cells, pancreatic cancer cells, nervous system cancer cells, lung cancer cells, kidney cancer cells, digestive system cancer cells, breast cancer cells, bone cancer cells, blood cancer cells, digestive tract cancer cells, and urogenital cancers cells.

3. The method of claim 1, wherein drug responsiveness value is an IC50 value.

4. The method of claim 3, wherein high drug responsiveness value is a lowest IC50 value for any of the plurality of cell lines.

5. The method of claim 3, wherein low drug responsiveness value is a highest IC50 value for any of the plurality of cell lines.

6. The method of claim 1, wherein the at least two cell lines each correspond to a primary cancer, and wherein the overlap cell line cluster corresponds to the primary cancer.

7. The method of claim 1, wherein the at least two cell lines each correspond to a primary cancer, and wherein the overlap cell line cluster includes a secondary cancer different than the primary cancer.

8. The method of claim 1, wherein if a plurality of alternative drugs exhibiting a drug responsiveness value between the high drug responsiveness value and the low drug responsiveness value are identified, identifying the alternative drug having the highest drug responsiveness for the overlapping cell line cluster; and administering to cells of one of the at least two cell lines the alternative drug having the highest drug responsiveness for the overlapping cell line cluster.

9. The method of claim 1, wherein the one or more alternative drugs comprises at least one drug combination comprising the treatment drug and an additive drug.

10. The method of claim 1, wherein the one or more alternative drugs comprises at least one drug combination that does not contain the treatment drug.

11. A method of grouping drugs for treating a pathology, the method comprising:
receiving, at a processing unit, drug responsiveness data for a set of drugs and for a set of cell lines;
grouping, using the processing unit, each of the drugs into a different drug grouping, using
(i) a generalized finite mixture of multivariate regression (FMMR) model as follows $$f(y_i \mid x_i, \Theta) = \sum_{(l_1...l_s) \in T} \pi_{(l_1...l_s)} f(y_i \mid x_i, B_{l_1}, ..., B_{l_s}, \Sigma).$$

wherein $f(y_i | x_i, B_{l_1}, ..., B_{l_s}, \Sigma)$ is a multivarite normal density function generalized for both non-overlapping clusters and overlapping clusters, $y_i$ are drug responsiveness values, $x_i$ are genomic biomarkers, $B_{l_1}, ..., B_{l_s}$ are coefficient matrix values for a cluster, are clusters, $\pi$ is an observation value indicating whether a drug belongs in a grouping ($\pi=1$) or not ($\pi=0$), and $\Sigma$ is an error term for the coefficient matrix values, i represents a drug, wherein the generalized FMMR model allows for modeling drugs for both non-overlapping clusters and overlapping clusters, and (ii) a clustering algorithm configured to group drugs based on the coefficient matrix values, B, for different drugs and based on cell line assignments to generate a group of alternative drugs corresponding to an overlap cell line cluster having a drug responsiveness value that is between a high drug responsiveness value and a low drug responsiveness value; and administering one or more of the alternative drugs from one of the drug groupings to a cell line expressing the pathology.

12. The method of claim 11, wherein the clustering algorithm is a multi-level nested clustering algorithm.

13. The method of claim 12, wherein clustering algorithm is an affinity-propagation clustering algorithm.

14. The method of claim 13, further comprising:
applying the affinity-propagation clustering algorithm at a first level to produce a first level of groupings; and
applying the affinity-propagation clustering algorithm to each of the first level of drug groupings, to produce a subsequent level of drug groupings.

\* \* \* \* \*

UNITED STATES PATENT AND TRADEMARK OFFICE
CERTIFICATE OF CORRECTION

PATENT NO. : 11,932,898 B2
APPLICATION NO. : 16/321755
DATED : March 19, 2024
INVENTOR(S) : Jonnagadda Sunil Rao et al.

It is certified that error appears in the above-identified patent and that said Letters Patent is hereby corrected as shown below:

In the Claims

Column 28, Line 52, Claim 1, "the" should be -- of the --.

Column 29, Line 14, Claim 8, "the" should be -- of the --.

Column 29, Line 32, Claim 11, " $f(y_i \mid x_i, \Theta) = \sum_{(l_1 \ldots l_s) \in T} \pi_{(l_1 \ldots l_s)} f(y_i \mid x_i, B_{l_1}, \ldots, B_{l_s}, \Sigma)$ ." should be -- $f(y_i \mid x_i, \Theta) = \sum_{(l_1 \ldots l_s) \in T} \pi_{(l_1 \ldots l_s)} f(y_i \mid x_i, B_{l_1}, \ldots, B_{l_s}, \Sigma)$ --.

Column 30, Line 1, Claim 11, "multivarite" should be -- multivariate --.

Column 30, Line 5, Claim 11, "cluster," should be -- cluster $l_1, \ldots l_s$, --.

Signed and Sealed this
Third Day of December, 2024

Katherine Kelly Vidal
*Director of the United States Patent and Trademark Office*